(12) United States Patent
Shuttleworth et al.

(10) Patent No.: US 10,442,815 B2
(45) Date of Patent: Oct. 15, 2019

(54) TRICYCLIC HETEROCYCLIC COMPOUNDS AS PHOSPHOINOSITIDE 3-KINASE INHIBITORS

(71) Applicant: Karus Therapeutics Limited, Oxfordshire (GB)

(72) Inventors: Stephen J. Shuttleworth, Oxfordshire (GB); Franck A. Silva, Oxfordshire (GB); Alexander R. L. Cecil, Oxfordshire (GB); Rikki P. Alexander, Oxfordshire (GB); Alice E. Gatland, Oxfordshire (GB); Daniel J. Finnemore, Oxfordshire (GB)

(73) Assignee: Karus Therapeutics Limited, Oxfordshire (GB)

( * ) Notice: Subject to any disclaimer, the term of this patent is extended or adjusted under 35 U.S.C. 154(b) by 0 days.

(21) Appl. No.: 15/753,358

(22) PCT Filed: Aug. 19, 2016

(86) PCT No.: PCT/GB2016/052581
§ 371 (c)(1),
(2) Date: Feb. 19, 2018

(87) PCT Pub. No.: WO2017/029521
PCT Pub. Date: Feb. 23, 2017

(65) Prior Publication Data
US 2018/0244685 A1    Aug. 30, 2018

(30) Foreign Application Priority Data
Aug. 19, 2015  (GB) .................................. 1514754.9

(51) Int. Cl.
*C07D 491/147*  (2006.01)
*C07D 495/14*   (2006.01)
*C07D 519/00*   (2006.01)

(52) U.S. Cl.
CPC ....... *C07D 491/147* (2013.01); *C07D 495/14* (2013.01); *C07D 519/00* (2013.01)

(58) Field of Classification Search
CPC . C07D 491/147; C07D 495/14; C07D 519/00
See application file for complete search history.

(56) References Cited

U.S. PATENT DOCUMENTS

| | | | |
|---|---|---|---|
| 3,491,092 A | 1/1970 | Grigat et al. | |
| 4,017,500 A | 4/1977 | Mayer et al. | |
| 5,703,075 A | 12/1997 | Gammill et al. | |
| 7,361,662 B2 | 4/2008 | Rault et al. | |
| 8,242,116 B2 * | 8/2012 | Alexander | C07D 513/04 514/234.2 |
| 8,338,592 B2 * | 12/2012 | Alexander | C07D 513/04 544/127 |
| 8,710,054 B2 * | 4/2014 | Alexander | C07D 513/04 514/234.2 |
| 8,921,361 B2 * | 12/2014 | Cmiljanovic | C07D 251/18 514/232.2 |
| 8,981,087 B2 | 3/2015 | Shuttleworth et al. | |
| 9,200,007 B2 * | 12/2015 | Shuttleworth | C07D 491/147 |
| 9,266,879 B2 | 2/2016 | Shuttleworth et al. | |
| 9,580,442 B2 * | 2/2017 | Shuttleworth | C07D 491/147 |
| 9,663,487 B2 | 5/2017 | Shuttleworth et al. | |
| 9,868,749 B2 * | 1/2018 | Alexander | C07D 471/04 |
| 9,890,174 B2 * | 2/2018 | Alexander | C07D 491/147 |
| 9,932,343 B2 * | 4/2018 | Alexander | C07D 471/04 |
| 9,938,290 B2 * | 4/2018 | Shuttleworth | C07D 491/147 |
| 9,981,987 B2 * | 5/2018 | Shuttleworth | C07D 519/00 |
| 10,035,785 B2 | 7/2018 | Shuttleworth et al. | |
| 10,087,179 B2 * | 10/2018 | Alexander | C07D 471/04 |
| 2002/0151544 A1 | 10/2002 | Hayakawa et al. | |
| 2007/0135466 A1 | 6/2007 | Ledeboer et al. | |
| 2010/0137302 A1 * | 6/2010 | Alexander | C07D 513/04 514/234.2 |

(Continued)

FOREIGN PATENT DOCUMENTS

EP  1277738 A1   1/2003
EP  1724267 A1  11/2006

(Continued)

OTHER PUBLICATIONS

U.S. Appl. No. 13/384,310, Benzo [E] [1,3] Oxazin-4-One Derivatives as Phosphoinositide 3-Kinase Inhibitors, filed Feb. 6, 2012, Patented, U.S. Pat. No. 8,981,087.

(Continued)

*Primary Examiner* — Alexander R Pagano
(74) *Attorney, Agent, or Firm* — Goodwin Procter LLP

(57) ABSTRACT

The invention relates to a compound of formula I:

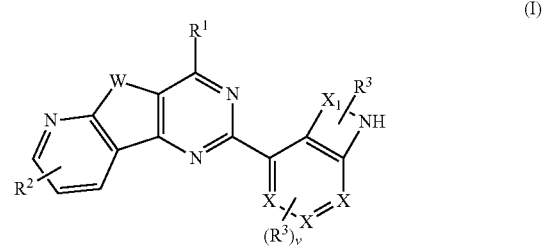

or a pharmaceutically acceptable salt thereof and/or stereoisomers thereof. The compounds of the invention are useful in therapy.

20 Claims, No Drawings

(56) References Cited

U.S. PATENT DOCUMENTS

| | | | | |
|---|---|---|---|---|
| 2011/0003785 | A1* | 1/2011 | Alexander | C07D 513/04 514/210.18 |
| 2011/0201608 | A1 | 8/2011 | Hoffmann et al. | |
| 2012/0178737 | A1* | 7/2012 | Shuttleworth | C07D 491/147 514/210.21 |
| 2013/0079330 | A1* | 3/2013 | Alexander | C07D 513/04 514/210.21 |
| 2013/0109688 | A1 | 5/2013 | Shuttleworth et al. | |
| 2015/0080395 | A1 | 3/2015 | Shuttleworth et al. | |
| 2016/0108057 | A1* | 4/2016 | Shuttleworth | C07D 491/147 514/210.21 |
| 2016/0113932 | A1 | 4/2016 | Stern et al. | |
| 2016/0297837 | A1* | 10/2016 | Alexander | C07D 471/04 |
| 2016/0304523 | A1* | 10/2016 | Alexander | C07D 471/04 |
| 2016/0304530 | A1* | 10/2016 | Alexander | C07D 491/147 |
| 2016/0347771 | A1* | 12/2016 | Shuttleworth | C07D 519/00 |
| 2016/0376268 | A1* | 12/2016 | Alexander | C07D 471/04 514/210.18 |
| 2018/0009826 | A1* | 1/2018 | Shuttleworth | C07D 491/147 |
| 2018/0235974 | A1 | 8/2018 | Shuttleworth et al. | |
| 2018/0243313 | A1 | 8/2018 | Shuttleworth et al. | |
| 2018/0243317 | A1 | 8/2018 | Shuttleworth et al. | |
| 2018/0244686 | A1* | 8/2018 | Shuttleworth | C07D 491/147 |
| 2019/0040079 | A1 | 2/2019 | Shuttleworth et al. | |
| 2019/0092790 | A1 | 3/2019 | Shuttleworth et al. | |

FOREIGN PATENT DOCUMENTS

| | | |
|---|---|---|
| WO | WO-01/83456 A1 | 11/2001 |
| WO | WO-02/02551 A1 | 1/2002 |
| WO | WO-02/085400 A1 | 10/2002 |
| WO | WO-2004/006846 A2 | 1/2004 |
| WO | WO-2004/043956 A1 | 5/2004 |
| WO | WO-2006/046035 A1 | 5/2006 |
| WO | WO-2006/127587 A1 | 11/2006 |
| WO | WO-2007/084667 A2 | 7/2007 |
| WO | WO-2007/122410 A1 | 11/2007 |
| WO | WO-2007/127183 A1 | 11/2007 |
| WO | WO-2008/064018 A1 | 5/2008 |
| WO | WO-2008/094992 A2 | 8/2008 |
| WO | WO-2008/121257 A1 | 10/2008 |
| WO | WO-2008/145688 A2 | 12/2008 |
| WO | WO-2008/150827 A1 | 12/2008 |
| WO | WO-2010/015520 A1 | 2/2010 |
| WO | WO-2010/037765 A2 | 4/2010 |
| WO | WO-2010/052569 A2 | 5/2010 |
| WO | WO-2011/012883 A1 | 2/2011 |
| WO | WO-2011/021038 A1 | 2/2011 |
| WO | WO-2011/079231 A1 | 6/2011 |
| WO | WO-2011/135351 A1 | 11/2011 |
| WO | WO-2013/014448 A1 | 1/2013 |
| WO | WO-2013/017480 A1 | 2/2013 |
| WO | WO-2013/132270 A1 | 9/2013 |
| WO | WO-2014/081718 A1 | 5/2014 |
| WO | WO-2014/181137 A1 | 11/2014 |
| WO | WO-2014/210354 A1 | 12/2014 |
| WO | WO-2015/054355 A1 | 4/2015 |
| WO | WO-2015/121657 A1 | 8/2015 |
| WO | WO-2017/029514 A1 | 2/2017 |
| WO | WO-2017/029517 A1 | 2/2017 |
| WO | WO-2017/029518 A1 | 2/2017 |
| WO | WO-2017/029519 A1 | 2/2017 |
| WO | WO-2017/029521 A1 | 2/2017 |

OTHER PUBLICATIONS

U.S. Appl. No. 13/388,164, Tricyclic Heterocyclic Compounds as Phosphoinositide 3-Kinase Inhibitors, filed Mar. 27, 2012, Patented, U.S. Pat. No. 9,200,007.
U.S. Appl. No. 14/920,410, Tricyclic Heterocyclic Compounds as Phosphoinositide 3-Kinase Inhibitors, filed Oct. 22, 2015, Patented, U.S. Pat. No. 9,580,442.
U.S. Appl. No. 15/410,114, Tricyclic Heterocyclic Compounds as Phosphoinositide 3-Kinase Inhibitors, filed Jan. 19, 2017, Patented, U.S. Pat. No. 9,938,290.
U.S. Appl. No. 15/909,011, Tricyclic Heterocyclic Compounds as Phosphoinositide 3-Kinase Inhibitors, filed Mar. 1, 2018, Pending, N/A.
U.S. Appl. No. 13/643,210, Naphthridine Derivatives as PI3K Inhibitors for the Treatment of Cancer and Immune-Inflammatory Disease, filed Jan. 7, 2013, Patented, U.S. Pat. No. 9,266,879.
U.S. Appl. No. 14/382,196, Phosphoinositide 3-Kinase Inhibitors, filed Aug. 29, 2014, Patented, U.S. Pat. No. 9,663,487.
U.S. Appl. No. 15/496,511, Phosphoinositide 3-Kinase Inhibitors, filed Apr. 25, 2017, Patented, U.S. Pat. No. 10,035,785.
U.S. Appl. No. 15/117,606, Tricyclic heterocyclic compounds as phosphoinositide 3-kinase inhibitors, filed Aug. 9, 2016, Patented, U.S. Pat. No. 9,981,987.
U.S. Appl. No. 15/961,404, Tricyclic heterocyclic compounds as phosphoinositide 3-kinase inhibitors, filed Apr. 24, 2018, Pending, N/A.
U.S. Appl. No. 15/753,361, Tricyclic heterocyclic compounds as phosphoinositide 3-kinase inhibitors, filed Feb. 19, 2018, Pending, US 2018-0244686 A1.
U.S. Appl. No. 15/753,359, Compositions comprising tricyclic heterocyclic compounds, filed Feb. 19, 2018, Pending, US 2018-0235974 A1.
U.S. Appl. No. 15/753,356, Compositions comprising a PI3K inhibitor and an HDAC inhibitor, filed Feb. 19, 2018, Pending, US 2018-0243317 A1.
U.S. Appl. No. 15/753,353, Compositions comprising PI3K inhibitors and a second antiproliferative agent, filed Feb 19, 2018, Pending, US 2018-0243313 A1.
Alvarez-Rua et al., "Multiple Hydrogen Bonds and Tautomerism in Naphthyridine Derivatives", New J. Chem. 28, 700-707 (2004).
Ameriks et al., Small Molecule Inhibitors of Phosphoinositide 3-Kinase (PI3K) δ and γ, Current Topics in Medicinal Chemistry, 2009, vol. 9, No. 8, pp. 738-753.
Baldev Singh et al., "Novel cAMP PDE III Inhibitors: 1,6-Naphthyridin-2(18)-ones", Journal of Medicinal Chemistry, American Chemical Society, 35(26): 5858-4865, Jan. 1, 1992, New York.
CAS Registry Nos. 1214438-02-4 and 1214393-37-9 (Mar. 25, 2010).
D.A. Kovalskiy et al., "Synthesis of 7-(3-piperidyl)[1,6]naphthyridine and 7-(4-piperidyl)[1,6]naphthyridine", Chemistry of Heterocyclic Compounds, 45(9): 1053-1057, Nov. 24, 2009.
Database Chemcats [Online], Chemical Abstracts Service, Apr. 22, 2011, Columbus, Ohio.
Erik L. Meredith et al., "Identification of Orally Available Naphthyridine Protein Kinase D Inhibitors", Journal of Medicinal Chemistry, 53(15): 5400-5421, Aug. 12, 2010.
Fabbro et al. Pharmacology & therapeutics 93, 79-98, 2002.
Golub et al., Science, 286, 531-537, 1999.
Hayakawa, et al., "Synthesis and Biological Evaluation of Pyrido[3',2':4,5]furo[3,2-d]pyrimidine Derivatives as Novel PI3 Kinase p110α Inhibitors" Bioorganic & Medicinal Chemistry Letters, 2007, vol. 17, pp. 2438-2442.
Hollebecque A et al., (2014), 'A Phase 1b Trial of LY2584702 Tosylate, a p70 S6 Inhibitor, in Combination with Erlotinib or Everolimus in Patients with Solid Tumours,' Eur J Cancer, 50(5):876-884.
International Preliminary Report on Patentability and Written Opinion of the International Searching Authority for PCT/GB2010/051221 dated Jan. 31, 2012 (7 pages).
International Preliminary Report on Patentability and Written Opinion of the International Searching Authority for PCT/GB2010/051370 dated Feb. 21, 2012 (6 pages).
International Preliminary Report on Patentability and Written Opinion of the International Searching Authority for PCT/GB2011/050824 dated Nov. 6, 2012 (7 pages).
International Preliminary Report on Patentability and Written Opinion of the International Searching Authority for PCT/GB2013/050583 dated Sep. 9, 2014 (6 pages).
International Search Report of the International Searching Authority for PCT/GB2010/051221 dated Oct. 7, 2010 (4 pages).

(56) References Cited

OTHER PUBLICATIONS

International Search Report of the International Searching Authority for PCT/GB2010/051370 dated Nov. 9, 2010 (4 pages).
International Search Report of the International Searching Authority for PCT/GB2011/050824 dated Jul. 12, 2011 (5 pages).
International Search Report of the International Searching Authority for PCT/GB2013/050583 dated May 6, 2013 (4 pages).
Lin L et al., (2014), 'Dual Targeting of Glioblastoma Multiforme with a Proteasome Inhibitor (Velcade) and a Phosphatidylinositol 3-Kinase Inhibitor (ZSTK474),' Int J Oncol, 44(2):557-562.
Mass, R. D., Int. J. Radiation Oncology Bio. Phys. vol. 58 (3): 932-940, 2004.
Notification of the Transmittal of the International Search Report and the Written Opinion of the International Searching Authority, or the Declaration, (form ISA/220), International Application No. PCT/GB2016/052575 , dated Nov. 9, 2016 (13 pages).
Notification of the Transmittal of the International Search Report and the Written Opinion of the International Searching Authority, or the Declaration, (form ISA/220), International Application No. PCT/GB2016/052577 , dated Nov. 9, 2016 (10 pages).
Notification of the Transmittal of the International Search Report and the Written Opinion of the International Searching Authority, or the Declaration, (form ISA/220), International Application No. PCT/GB2016/052578 , dated Oct. 25, 2016 (12 pages).
Notification of the Transmittal of the International Search Report and the Written Opinion of the International Searching Authority, or the Declaration, (form ISA/220), International Application No. PCT/GB2016/052581 , dated Oct. 24, 2016 (13 pages).
Schröder E et al., 'Arzneimittel Chemie Passage,' *Arzneimittelchemie Grundlagen Nerven, Muskeln and Gewebe [Pharmaceutical Chemistry I: Basic, Nerves, Muscles and Tissues]*, (1ST Ed, 1976), Thieme Georg Verla, Stuttgart DE (Publ) pp. 30-33 and Table 8 XP002186820.
Tao J et al., (2013), 'Combined Treatment of BTK and PI3K Inhibitors Synergistically Disrupts BCR-Signaling, Overcomes Microenvironment-Mediated Survival and Drug Resistance in Mantle Cell Lymphoma,' Proceedings of the 104th Annual Meeting of the American Association for Cancer Research, Apr. 6-10, 2013, Washington, D.C. Philadelphia PA, AACR Abstract #4944, OASIS, Chicago, IL (Publ) (2 pages) [retrieved on Jul. 16, 2014 at <http://www.abstractsonline.com/Plan/ViewAbstract.aspx?Key=605> . . . ] (Abstract).

Verheijen et al., "Phosphatidylinositol 3-kinase (PI3K) inhibitors as anticancer drugs", Drugs of the Future, 2007, vol. 32, No. 6, pp. 537-547.
Yamada T et al., (2013) 'A Novel HDAC Inhibitor OBP-801 and a PI3K Inhibitor LY294002 Synergistically Induce Apoptosis via the Suppression of Survivin and XIAP in Renal Cell Carcinoma,' Int J Oncol, 43(4):1080-6.
Zhong H et al., (2013) 'Synergistic Effects of Concurrent Blockade of PI3K and MEK Pathways in Pancreatic Cancer Preclinical Models,' PLoS One, 8(10):e77243.
Zhou W et al., (2009) Novel Mutant-Selective EGFR Kinase Inhibitors Against EGFR T790M, Nature, 462(7276):1070-4 [NIH Public Access Version].
Cohen et al., Current Opinion in Chemical Biology, 3, 459-465, 1999.
International Preliminary Report on Patentability and Written Opinion of the International Searching Authority for PCT/GB2015/050396 dated Aug. 16, 2016 (6 pages).
International Search Report of the International Searching Authority for PCT/GB2015/050396 dated Mar. 25, 2015 (3 pages).
Somei et al., "Boronation-Thallation, A New Approach to the Synthesis of Indoles Having Aryl and/or a Heteroaryl Substituent at the 4-Position." Chem. Pharm. Bull. 1986, 34, 3971-3.
Annex to Form PCT/ISA/206 Communication relating to the results of the partial international search for International Application No. PCT/GB2016/052571 dated Nov. 9, 2016 (4 pages).
Saifuddin, M. et al., "Water-Accelerated Cationic pi-(7-endo) cyclisation: Application to Indole-Based Peri-Annulated Polyheterocycles." European Journal of Organic Chemistry, 2010, 26, 5108-5117.
Written Opinion of the International Searching Authority for PCT/GB2016/052571 dated Feb. 23, 2017 (9 pages).
International Search Report of the International Searching Authority for PCT/GB2016/052571 dated Feb. 23, 2017 (6 pages).
Zhao, X. et al. Discovery of novel Bruton's tyrosine kinase (BTK) inhibitors bearing a pyrrolo[2,3-d]pyrimidine scaffold. Bioorganic and Medicinal Chemistry, 23, 2015, 891-901.
Shuttleworth, S. J. et al. Progress in the Preclinical Discovery and Clinical Development of Class I and Dual Class I/IV Phosphoinositide 3-Kinase (PI3K) Inhibitors. Current Medicinal Chemistry, 2011, 18, 2686-2714.
Brachmann, S. et al. PI3K and mTOR inhibitors—a new generation of targeted anticancer agents. Current Opinion in Cell Biology. 2009, 21, 194-198.
Liu, Q. et al. mTOR mediated anti-cancer drug discovery. Drug Discovery Today: Therapeutic Strategies. 2009, 6 (2), 47-55.

* cited by examiner

TRICYCLIC HETEROCYCLIC COMPOUNDS AS PHOSPHOINOSITIDE 3-KINASE INHIBITORS

CROSS-REFERENCE TO RELATED APPLICATIONS

This application is the national stage application of International Patent Application No. PCT/GB2016/052581, filed Aug. 19, 2016, which claims the benefit of and priority to Great Britain Patent Application No. 1514754.9, filed Aug. 19, 2015, the contents of each of which are hereby incorporated by reference in their entirety.

FIELD OF THE INVENTION

The present invention relates to novel compounds which act as inhibitors of the class IA phosphoinositide 3-kinase enzymes, PI3K-p110β and PI3K-p110δ, for the treatment of cancer, immune and inflammatory diseases.

BACKGROUND OF THE INVENTION

The phosphoinositide 3-kinases (PI3Ks) constitute a family of lipid kinases involved in the regulation of a network of signal transduction pathways that control a range of cellular processes. PI3Ks are classified into three distinct subfamilies, named class I, II, and III based upon their substrate specificities. Class IA PI3Ks possess a p110α, p110β, or p110δ catalytic subunit complexed with one of three regulatory subunits, p85α, p85β or p55δ. Class IA PI3Ks are activated by receptor tyrosine kinases, antigen receptors, G-protein coupled receptors (GPCRs), and cytokine receptors. The class IA PI3Ks primarily generate phosphatidylinositol-3,4,5-triphosphate (PI(3,4,5)P$_3$), a second messenger that activates the downstream target AKT. The consequences of biological activation of AKT include tumour cell progression, proliferation, survival and growth, and there is significant evidence suggesting that the PI3K/AKT pathway is dysregulated in many human cancers. Additionally, PI3K activity has been implicated in endocrinology, cardiovascular disease, immune disorders and inflammation. It has been established that PI3K-p110δ plays a critical role in the recruitment and activation of immune and inflammatory cells. PI3K-p110δ is also upregulated in a number of human tumours and plays a key role in tumour cell proliferation and survival.

Compounds which are able to modulate p110β and p110δ activity have important therapeutic potential in cancer and immune and inflammatory disorders.

WO 2011/021038 describes compounds which act as inhibitors of PI3K-p110δ.

SUMMARY OF THE INVENTION

The present invention relates at least in part to PI3K-p110β/δ modulating compounds having surprisingly significant activity and/or bioavailability. even as compared to certain known PI3K-p110β/δ modulating compounds.

Therefore, the invention is directed at least in part to a compound of formula I:

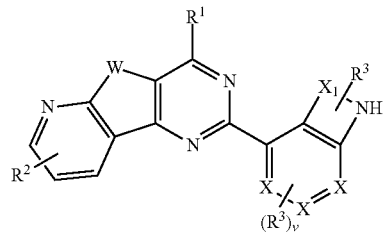

or a pharmaceutically acceptable salt and/or stereoisomers thereof, wherein:

W is selected from the group consisting of O, N—H, N—(C$_1$-C$_{10}$ alkyl) and S (O)$_{ww}$ wherein ww is 0, 1, or 2 each X is independently selected from CH or N;

X$_1$ is —CH$_2$—CH$_2$—, —CH=CH— or —CH$_2$—C(O)— wherein C(O) is attached to NH;

v is selected from 0, 1, 2 and 3;

R$^1$ is a 5 to 7-membered heterocycle containing at least 1 heteroatom selected from N or O;

R$^2$ is -L-Y;

L is selected from the group consisting of a direct bond, C$_1$-C$_{10}$ alkylene, C$_2$-C$_{10}$ alkenylene or C$_2$-C$_{10}$ alkynylene;

Y is an optionally substituted 4- to 8-membered heterocycle containing at least one nitrogen atom and at least one sulfur atom, or —N(R$^5$)-A-S(O$_q$)R$^6$;

R$^5$ is independently selected from H, C$_1$-C$_{10}$ alkyl, C$_2$-C$_{10}$ alkenyl or C$_3$-C$_{10}$ alkynyl;

R$^6$ is independently selected from C$_1$-C$_{10}$ alkyl, C$_2$-C$_{10}$ alkenyl or C$_3$-C$_{10}$ alkynyl, fluoro C$_1$-C$_{10}$ alkyl, —O—C$_1$-C$_{10}$ alkyl, —NH—C$_1$-C$_{10}$ alkyl, —O-fluoro C$_1$-C$_{10}$ alkyl, —NH-acyl, —NH—C(O)—NH—C$_1$-C$_{10}$ alkyl, —C(O)—NH—C$_1$-C$_{10}$ alkyl, aryl or heteroaryl;

A is selected from the group consisting of optionally substituted C$_1$-C$_{10}$ alkylene, C$_2$-C$_{10}$ alkenylene or C$_3$-C$_{10}$ alkynylene;

q is selected from 0, 1 and 2; and each R$^3$ is independently selected from the group consisting of H, C$_1$-C$_{10}$ alkyl, halogen, —CN, —CO$_2$H, fluoro C$_1$-C$_{10}$ alkyl, —O—C$_1$-C$_{10}$ alkyl, —NH—C$_1$-C$_{10}$ alkyl, —NH$_2$, —S—C$_1$-C$_{10}$ alkyl, —O-fluoro C$_1$-C$_{10}$ alkyl, —NH-acyl, —NH—C(O)—NH-C$_1$-C$_{10}$ alkyl, —C(O)—NH—C$_1$-C$_{10}$ alkyl, aryl or heteroaryl; and each alkyl, alkenyl, alkylene, alkenylene, acyl, heterocycle or heteroaryl may be optionally substituted by C$_1$-C$_6$ alkyl, hydroxy, C$_1$-C$_3$ hydroxyalkyl, C$_1$-C$_3$ alkoxy, C$_1$-C$_3$ haloalkoxy, fluoro C$_1$-C$_3$ alkyl, amino, C$_1$-C$_3$ mono alkylamino, C$_1$-C$_3$ bis alkylamino, C$_1$-C$_3$ acylamino, C$_1$-C$_3$ aminoalkyl, mono (C$_1$-C$_3$ alkyl) amino C$_1$-C$_3$ alkyl, bis (C$_1$-C$_3$ alkyl) amino C$_1$-C$_3$ alkyl, C$_1$-C$_3$-acylamino, C$_1$-C$_3$ alkyl sulfonylamino, acyl, halo, nitro, cyano, carboxy, C$_1$-C$_3$ alkoxycarbonyl, aminocarbonyl, mono C$_1$-C$_3$ alkyl aminocarbonyl, bis C$_1$-C$_3$ alkyl aminocarbonyl, —SO$_3$H, C$_1$-C$_3$ alkylsulfonyl, aminosulfonyl, mono C$_1$-C$_3$ alkyl aminosulfonyl or bis C$_1$-C$_3$-alkyl aminosulfonyl.

The invention may also be directed at least in part to a compound of formula II:

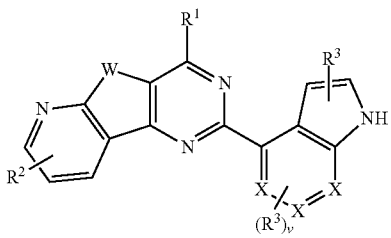

(II)

or a pharmaceutically acceptable salt thereof, wherein:

W is selected from the group consisting of O, N—H, N—($C_1$-$C_{10}$ alkyl) and S;

each X is independently selected from CH or N;

v is selected from 0, 1, 2 and 3;

$R^1$ is a 5 to 7-membered heterocycle containing at least 1 heteroatom selected from N or O;

$R^2$ is -L-Y;

L is selected from the group consisting of a direct bond, $C_1$-$C_{10}$ alkylene, $C_2$-$C_{10}$ alkenylene or $C_2$-$C_{10}$ alkynylene;

Y is an optionally substituted 4- to 7-membered heterocycle containing at least one nitrogen atom and at least one sulfur atom, or —N($R^5$)-A-S($O_q$)$R^6$;

$R^5$ is independently selected from H, $C_1$-$C_{10}$ alkyl, $C_2$-$C_{10}$ alkenyl or $C_3$-$C_{10}$ alkynyl;

$R^6$ is independently selected from $C_1$-$C_{10}$ alkyl, $C_2$-$C_{10}$ alkenyl or $C_3$-$C_{10}$ alkynyl, fluoro $C_1$-$C_{10}$ alkyl, —O—$C_1$-$C_{10}$ alkyl, —NH-$C_1$-$C_{10}$ alkyl, —O-fluoro $C_1$-$C_{10}$ alkyl, —NH-acyl, —NH—C(O)—NH—$C_1$-$C_{10}$ alkyl, —C(O)—NH—$C_1$-$C_{10}$ alkyl, aryl or heteroaryl;

A is selected from the group consisting of optionally substituted $C_1$-$C_{10}$ alkylene, $C_2$-$C_{10}$ alkenylene or $C_3$-$C_{10}$ alkynylene;

q is selected from 0, 1 and 2; and each $R^3$ is independently selected from the group consisting of H, $C_1$-$C_{10}$ alkyl, halogen, fluoro $C_1$-$C_{10}$ alkyl, —O—$C_1$-$C_{10}$ alkyl, —NH—$C_1$-$C_{10}$ alkyl, —$NH_2$, —S—$C_1$-$C_{10}$ alkyl, —O-flouro $C_1$-$C_{10}$ alkyl, —NH-acyl, —NH—C(O)—NH—$C_1$-$C_{10}$ alkyl, —C(O)—NH—$C_1$-$C_{10}$ alkyl, aryl or heteroaryl; and each alkyl, alkenyl, alkylene, alkenylene, acyl, heterocycle or heteroaryl may be optionally substituted by $C_1$-$C_6$ alkyl, hydroxy, $C_1$-$C_3$ hydroxyalkyl, $C_1$-$C_3$ alkoxy, $C_1$-$C_3$ haloalkoxy, fluoro $C_1$-$C_3$ alkyl, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, acyl, halo, nitro, cyano, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl or bis $C_1$-$C_3$-alkyl aminosulfonyl.

DESCRIPTION OF THE PREFERRED EMBODIMENTS

Definitions

As used herein, "alkyl" means a $C_1$-$C_{10}$ alkyl group, which can be linear or branched. Preferably, it is a $C_1$-$C_6$ alkyl moiety. More preferably, it is a $C_1$-$C_4$ alkyl moiety. Examples include methyl, ethyl, n-propyl and t-butyl. It may be divalent, e.g. propylene.

As used herein, "alkenyl" means a $C_2$-$C_{10}$ alkenyl group. Preferably, it is a $C_2$-$C_6$ alkenyl group. More preferably, it is a $C_2$-$C_4$ alkenyl group. The alkenyl radicals may be mono- or di-saturated, more preferably monosaturated. Examples include vinyl, allyl, 1-propenyl, isopropenyl and 1-butenyl. It may be divalent, e.g. propenylene.

As used herein, "alkynyl" is a $C_2$-$C_{10}$ alkynyl group which can be linear or branched. Preferably, it is a $C_3$-$C_{10}$ alkynyl group or $C_2$-$C_4$ alkynyl group or moiety. It may be divalent.

Each of the $C_1$-$C_{10}$ alkyl, $C_2$-$C_{10}$ alkenyl and $C_2$-$C_{10}$ alkynyl groups may be optionally substituted with each other, i.e. $C_1$-$C_{10}$ alkyl optionally substituted with $C_2$-$C_{10}$ alkenyl. They may also be optionally substituted with aryl, cycloalkyl (preferably $C_3$-$C_{10}$), aryl or heteroaryl. They may also be substituted with halogen (e.g. F, Cl), $NH_2$, $NO_2$ or hydroxyl. Preferably, they may be substituted with up to 10 halogen atoms or more preferably up to 5 halogens. For example, they may be substituted by 1, 2, 3, 4 or 5 halogen atoms. Preferably, the halogen is fluorine. For example, they may be, or be substituted with, $CF_3$, $CHF_2$, $CH_2CF_3$, $CH_2CHF_2$ or $CF_2CF_3$.

As used herein, the term "fluoro $C_1$-$C_{10}$ alkyl" means a $C_1$-$C_{10}$ alkyl substituted with one or more fluorine atoms. Preferably, one, two, three, four or five fluorine atoms. Examples of "fluoro $C_1$-$C_{10}$ alkyl" are $CF_3$, $CHF_2$, $CH_2F$, $CH_2CF_3$, $CH_2CHF_2$ or $CF_2CF_3$.

As used herein, "aryl" means a monocyclic, bicyclic, or tricyclic monovalent or divalent (as appropriate) aromatic radical, such as phenyl, biphenyl, naphthyl, anthracenyl, which can be optionally substituted with up to five substituents preferably selected from the group consisting of $C_1$-$C_6$ alkyl, hydroxy, $C_1$-$C_3$ hydroxyalkyl, $C_1$-$C_3$ alkoxy, $C_1$-$C_3$ haloalkoxy, fluoro $C_1$-$C_3$ alkyl amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, "heteroaryl" means a monocyclic, bicyclic or tricyclic monovalent or divalent (as appropriate) aromatic radical containing up to four heteroatoms selected from oxygen, nitrogen and sulfur, such as thiazolyl, isothiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, triazolyl, thiadiazolyl, oxadiazolyl, said radical being optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, fluoro $C_1$-$C_3$ alkyl, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, the term "heterocycle" a mono- or divalent carbocyclic radical containing up to 4 heteroatoms selected from oxygen, nitrogen and sulfur. A heterocycle can refer to, for example, a saturated or partially unsaturated 4- to 12, 4-10 or 4-7-membered ring structure, including bridged (e.g., bridged bicyclic), spirocyclic, or fused rings, and whose ring structures include one to three heteroatoms, such as nitrogen, oxygen, and sulfur. Where possible, heterocyclic rings may be linked to the adjacent radical through carbon or nitrogen. Preferably, it contains one or two heteroatoms. Preferably, at least one of the heteroatoms is nitrogen. It may be monocyclic or bicyclic. For the avoidance of doubt, the term "heterocycle" covers "heteroaryl" and "heterocycloalkyl".

As used herein, "heterocycloalkyl" is a carbocyclic radical where the bonds between the atoms in the ring are single bonds. Examples of heterocycloalkyls are piperidine, piperazine, thiomorpholine, morpholine, azetidine or oxetane. More preferably, the heterocycloalkyl is morpholine or its 7-membered homologue.

The heterocycle or heterocycloalkyl ring may be mono- or di-unsaturated. The radical may be optionally substituted with up to three substituents independently selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo (e.g. F), nitro, cyano, carboxy, $C_1$-$C_3$-haloalkyl (e.g. $CF_3$), $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

In summary, each of the groups defined above, i.e., alkyl, alkenyl, alkynyl, aryl, heteroaryl, heterocycle, heterocycloalkyl, may be optionally substituted with up to three substituents (preferably one) preferably selected from the group consisting of $C_1$-$C_6$ alkyl, hydroxy, $C_1$-$C_3$ hydroxyalkyl, $C_1$-$C_3$ alkoxy, $C_1$-$C_3$ haloalkoxy, fluoro $C_1$-$C_3$ alkyl, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, acyl, halo (e.g. fluoro), nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

Alternatively, each of the groups defined above, i.e., alkyl, alkenyl, alkynyl, aryl, heteroaryl, heterocycle, heterocycloalkyl, may be optionally substituted by $R_x$, wherein $R_x$ is selected from the group consisting of $C_1$-$C_6$ alkyl, hydroxy, $C_1$-$C_3$ hydroxyalkyl, $C_1$-$C_3$ alkoxy, $C_1$-$C_3$ haloalkoxy, fluoro $C_1$-$C_3$ alkyl, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, acyl, halo (e.g. fluoro), nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, the above groups can be followed by the suffix -ene. This means that the group is divalent, i.e. a linker group.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomers with R or S stereochemistry at each chiral axis. The invention includes all such enantiomers and diastereoisomers and mixtures thereof.

Preferred Groups of the Invention

Preferably, when the invention is defined according to Formula I, $R^2$ is -L-Y;

L is selected from the group consisting of a direct bond, $C_1$-$C_{10}$ alkylene, $C_2$-$C_{10}$ alkenylene or $C_2$-$C_{10}$ alkynylene; and Y is an optionally substituted 4- to 7-membered heterocycle containing at least one nitrogen atom and at least one sulfur atom, or —$N(R^5)$-A-$S(O_q)R^6$.

Preferably, when the invention is defined according to Formula I, $X_1$ is —CH=CH—. In this case, it is preferred that X is N. In other words, the right hand side ring (as drawn) of Formula (I) is, preferably, indole, as depicted below:

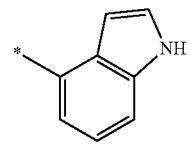

Preferably, when the invention is defined according to Formula I, $R^3$ is independently selected from the group consisting of H, $C_1$-$C_{10}$ alkyl, halogen, fluoro $C_1$-$C_{10}$ alkyl, —O—$C_1$-$C_{10}$ alkyl, —NH—$C_1$-$C_{10}$ alkyl, —$NH_2$, —S—$C_1$-$C_{10}$ alkyl, —O-fluoro $C_1$-$C_{10}$ alkyl, —NH-acyl, —NH—C(O)—NH—$C_1$-$C_{10}$ alkyl, —C(O)—NH—$C_1$-$C_{10}$ alkyl, aryl or heteroaryl.

Preferably, when the invention is defined according to Formula I, $R^3$ is independently selected from H, $C_1$-$C_{10}$ alkyl, CN, $CO_2H$, halogen, —O—$C_1$-$C_{10}$ alkyl, —O-flouro $C_1$-$C_{10}$ alkyl and fluoro $C_1$-$C_{10}$ alkyl.

The following description of the preferred groups of the invention is applicable to the invention as defined by either Formula I or Formula II.

Preferably, $R^1$ is represented by any of the following structures:

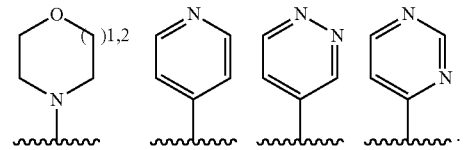

More preferably, $R^1$ is a heterocycloalkyl. More preferably still, it is

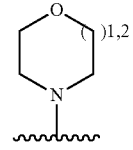

Most preferably, $R^1$ is morpholine.

In a preferred embodiment of the invention, W is oxygen or sulfur, preferably oxygen.

Preferably X is CH.

Preferably $R^3$ is H, $C_1$-$C_{10}$ alkyl, halogen (preferably fluoro) or fluoro $C_1$-$C_{10}$ alkyl. More preferably $R^3$ is H or halogen or $CF_3$. Most preferably $R^3$, for each occurrence is H.

It is alternatively preferred that, $R^3$ on the right hand side (RHS) of the indole (as drawn) is H, and $R^3$ on the left hand side (LHS) of the indole (as drawn) is H, F or $CF_3$.

It is preferred that v is 0 or 1. In other words, it is preferred that the LHS of the indole (as drawn) has no substitution or has only one substituent.

Preferably, the 6,5-ring system in Formula I or Formula II is an indole. In other words, $R^3$ is hydrogen and X is CH.

$R^2$ may be attached to any suitable atom on the aryl group, as depicted in general formula I or II. However, it is preferred that $R^2$ is attached to the meta-position of the pyridine ring. For example, if the nitrogen atom of the pyridine is labelled as atom number 1, then $R^2$ is attached in the 3-position.

$R^2$ is LY. Preferably, L is $C_1$-$C_{10}$ alkylene, preferably methylene.

Preferably, q is 2, such that a sulfonyl (i.e. $SO_2$) is present.
Preferably, $R^5$ is $C_1$-$C_{10}$ alkyl, preferably $C_1$-$C_4$ alkyl.
Preferably, A is $C_1$-$C_{10}$ alkylene, preferably $C_1$-$C_4$ alkylene.
Preferably, $R^6$ is independently selected from $C_1$-$C_{10}$ alkyl, fluoro $C_1$-$C_{10}$ alkyl, —O—$C_1$-$C_{10}$ alkyl, —NH—$C_1$-$C_{10}$ alkyl, aryl or heteroaryl.

Where Y is a 4- to 7-membered heterocycle containing at least one nitrogen atom and at least one sulfur atom, it is preferably a heterocycloalkyl group. Preferably, where Y is a 4- to 7-membered nitrogen- and sulfur-containing heterocycle, it is bound to L through the nitrogen atom.

Preferably, where Y is a 4- to 7-membered heterocycle containing at least one nitrogen atom and at least one sulfur atom, it contains only one nitrogen atom and only one sulfur atom and can be represented by:

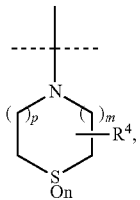

wherein
m is selected from 0, 1 and 2,
n is selected from 0, 1 and 2,
p is selected from 0 and 1, and
$R^4$ is independently selected from H, $C_1$-$C_{10}$ alkyl, halogen, fluoro $C_1$-$C_{10}$ alkyl, —O—$C_1$-$C_{10}$ alkyl, —NH—$C_1$-$C_{10}$ alkyl, —NH$_2$, —S—$C_1$-$C_{10}$ alkyl, —O-flouro $C_1$-$C_{10}$ alkyl, —NH-acyl, —NH—C(O)—NH—$C_1$-$C_{10}$ alkyl, —C(O)—NH—$C_1$-$C_{10}$ alkyl, aryl or heteroaryl.

Preferably, p and m are 1, such that Y is preferably a 6-membered heterocycloalkyl containing one nitrogen and one sulfur atom.

Preferably, n is 1 or 2, more preferably 1.
Preferably, $R^4$ is H.

Alternatively, Y may be defined according to Formula (III) or Formula (IV), preferably according to Formula (III):

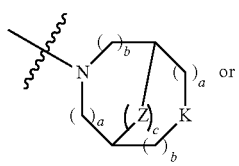  (III)

or

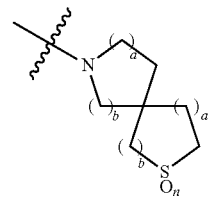  (IV)

wherein:
Z is selected from O, S and $CH_2$;
K is selected from —S—, —S═O (sulfoxide), —SO$_2$ (sulfone) and

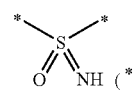

represents the position(s) of attachment;
each a is independently selected from 1, 2 and 3;
each b is independently selected from 0, 1 and 2;
n is 0, 1 or 2; and
c is 0 or 1.

It is preferred that Z is methylene, i.e. $CH_2$ and c is 1.

When Y is defined according to Formula (III), it is preferred that a is 1 and b is 0. It is also preferred that n is 1 or 2, more preferably n is 1.

When Y is defined according to Formula (IV), it is preferred that n is 1 or 2, more preferably 2. It is also preferred that a is 0 and b is 1 when Y is Formula (IV).

Preferably, Y is selected from:

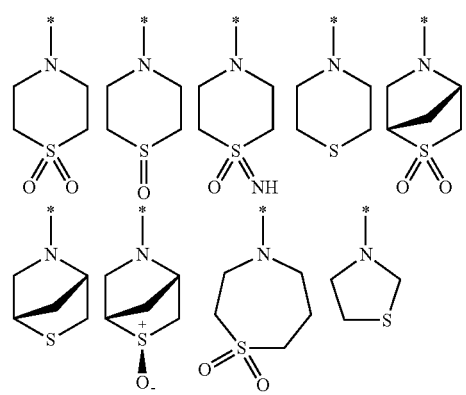

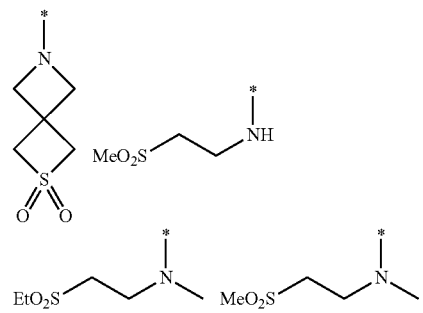

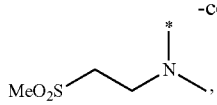

wherein * represents the position of attachment to L.

Preferably, L is methylene and Y is attached to L through a nitrogen atom of the 4- to 7-membered heterocycle. This is depicted in all of the examples of the invention.

Y may also be —NR$^{11}$R$^{12}$, wherein R$^{11}$ and R$^{12}$ together with the nitrogen to which they are attached form a 5- to 6-membered heterocyclic ring having an (SO)$_q$ moiety in the ring, or wherein R$^{11}$ and R$^{12}$ are independently selected from H, C$_{1-4}$ alkyl and -ethylene-S(O)$_q$-R$^{66}$.

For example, provided herein are disclosed compounds having a sulfur-containing heterocyclic ring is represented by the following formula:

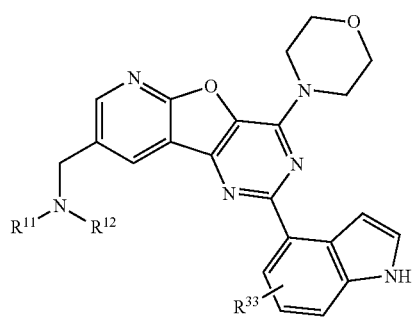

and pharmaceutically acceptable salts thereof; wherein

R$^{11}$ and R$^{12}$ together with the nitrogen to which they are attached form a 5-6 or 5-7 membered monocyclic, bridged bicyclic, or spirocyclicheterocyclic ring having an S(O)$_q$ or S(O)(NR') moiety in the ring, wherein q is 0, 1 or 2; or R$^{11}$ is -ethylene-S(O)$_q$-R$^{66}$ wherein q is 0, 1, or 2 and R$^{12}$ is selected from H and C$_{1-6}$alkyl;

R$^{66}$ is selected from the group consisting of H, C$_{1-3}$alkyl, and —NHC$_{1-3}$alkyl;

R' is H or C$_{1-3}$alkyl and

R$^{33}$ is selected from the group consisting of H, halogen, cyano, C$_{1-4}$alkyl (optionally substituted by one, two, or three halogens); C$_{1-4}$alkoxy (optionally substituted by one, two, or three halogens), and —C(O)—OR$^{34}$, where R$^{34}$ is H or C$_{1-4}$alkyl Examples of structures embodying the invention are:

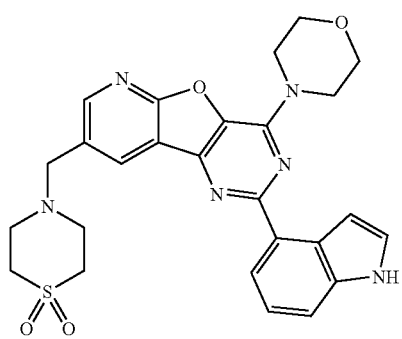

A

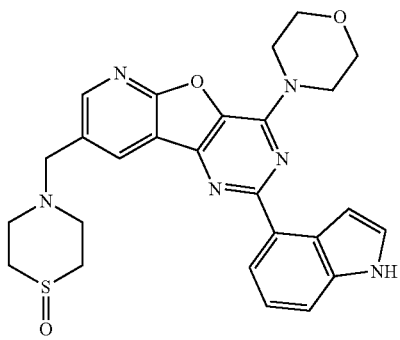

B

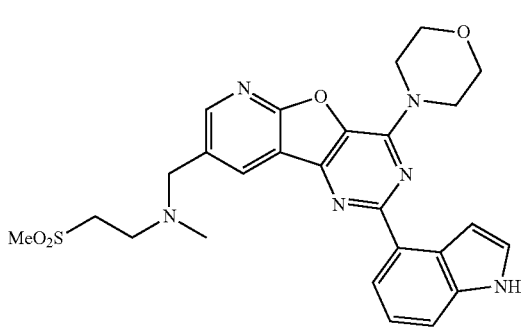

C

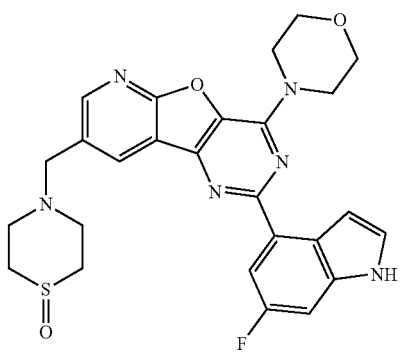

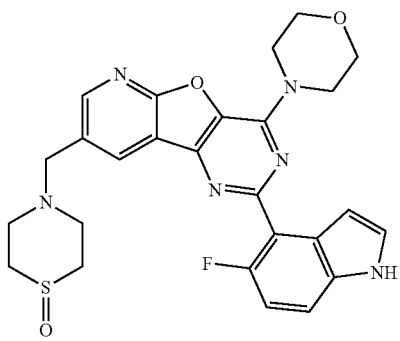

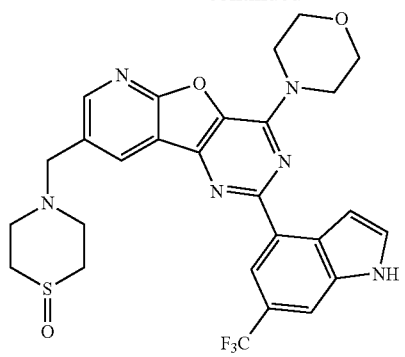
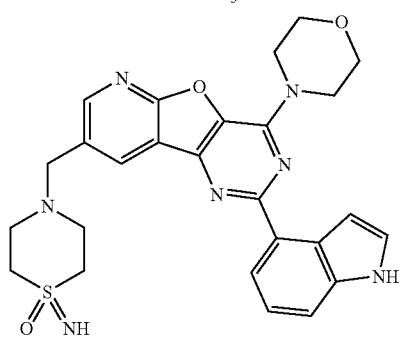
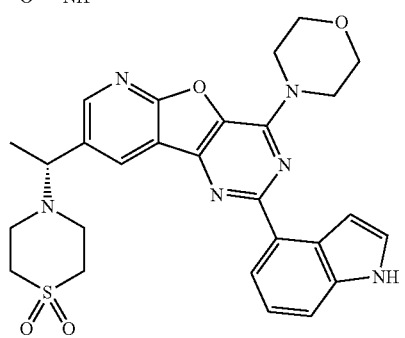
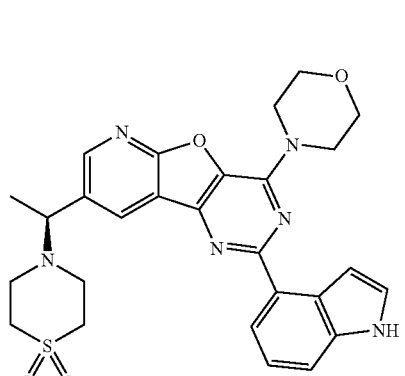
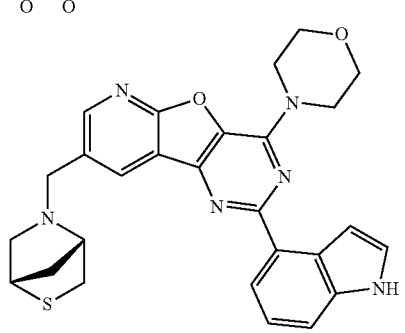
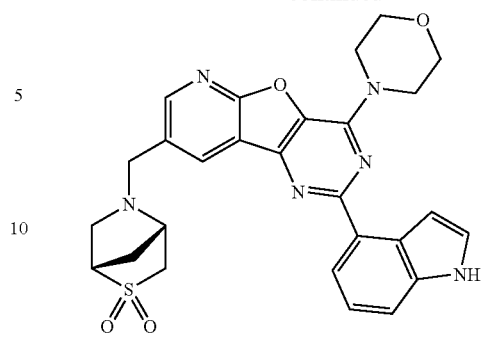
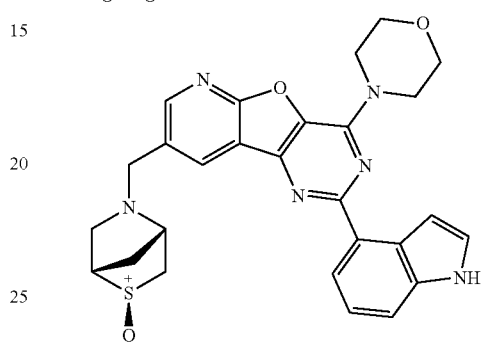
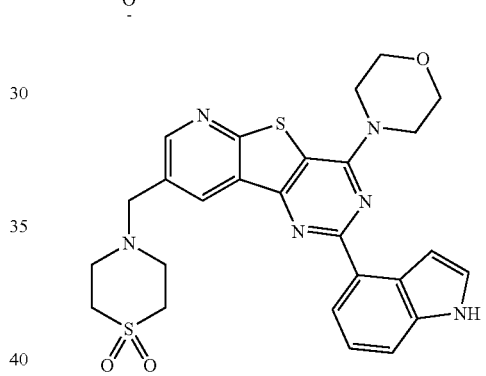
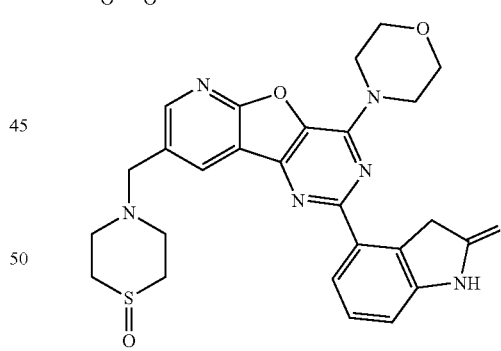
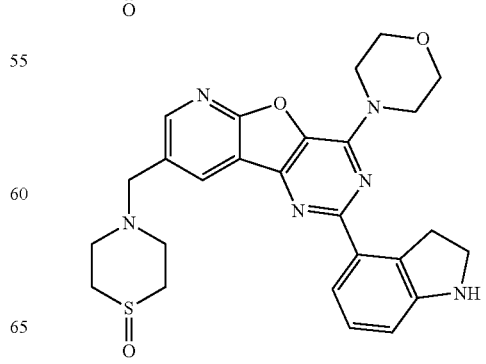

-continued
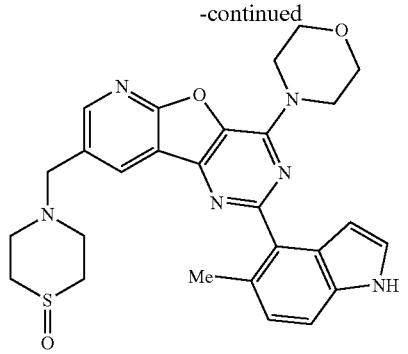
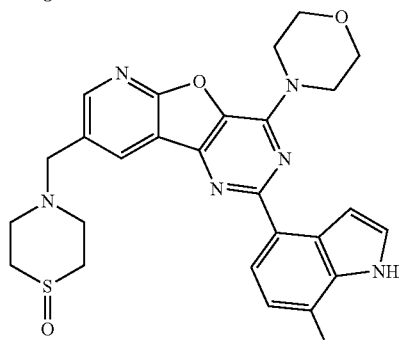
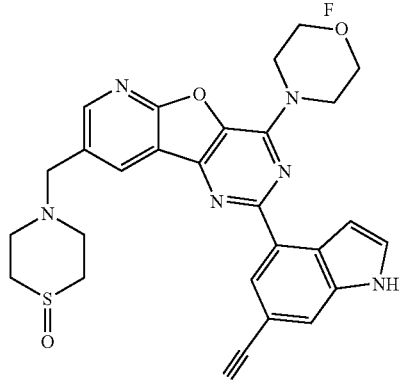
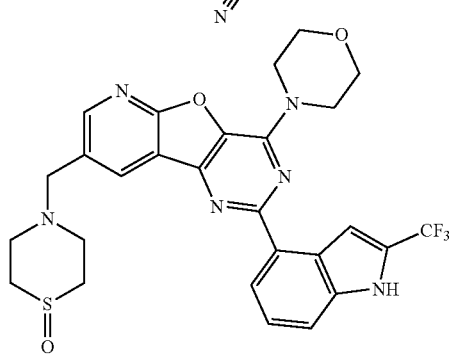
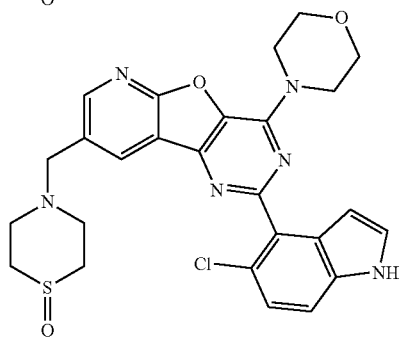
-continued
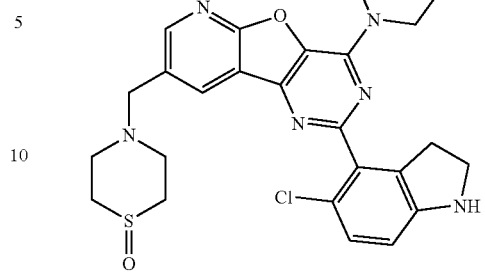
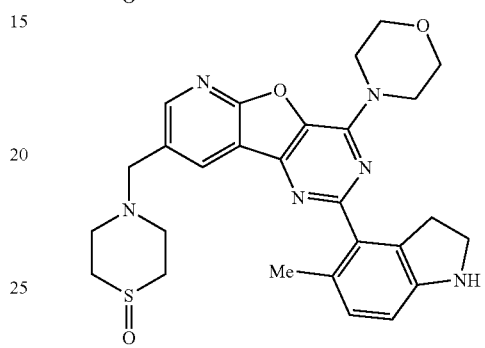
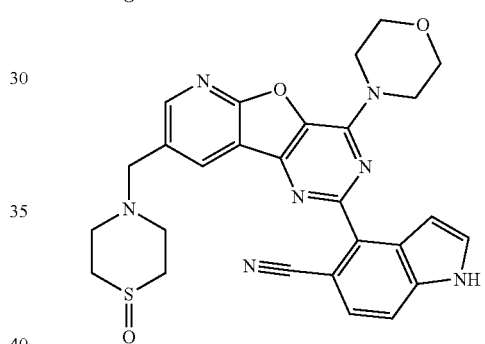
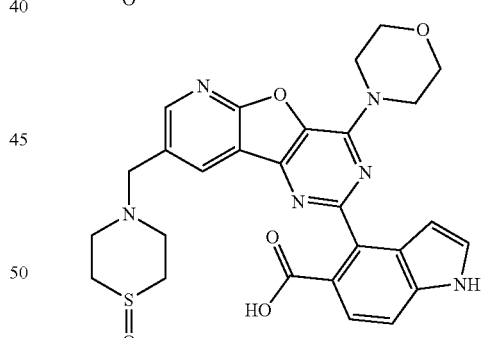
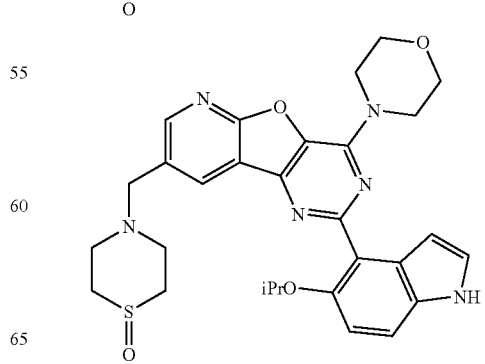

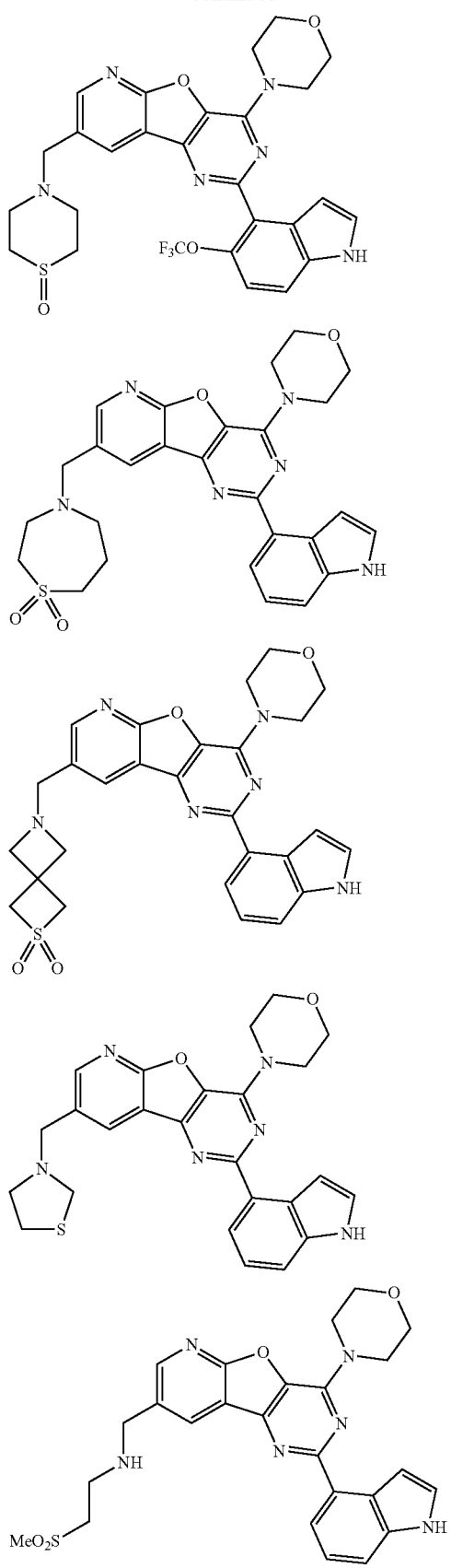
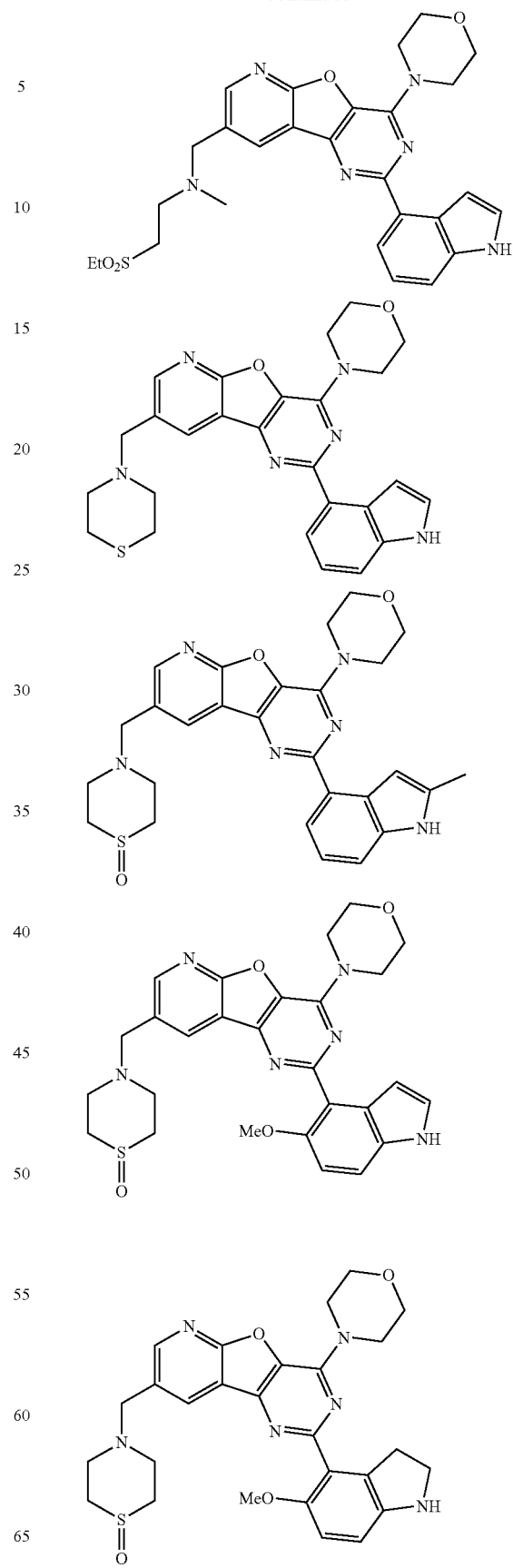

-continued

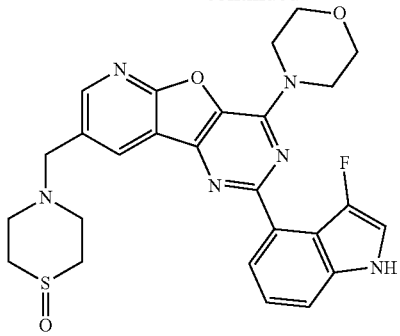

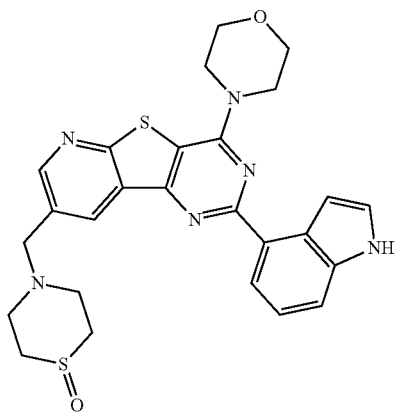

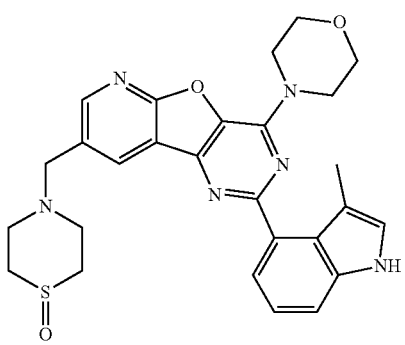

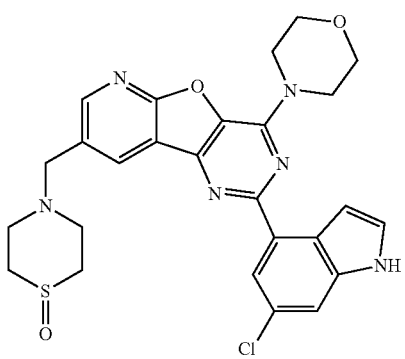

-continued

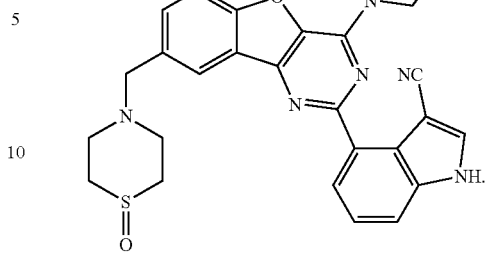

A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention. For example, contemplated herein is a pharmaceutically acceptable composition comprising a disclosed compound and a pharmaceutically acceptable excipient.

As used herein, a pharmaceutically acceptable salt is a salt with a pharmaceutically acceptable acid or base. Pharmaceutically acceptable acids include both inorganic acids such as hydrochloric, sulfuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

For the avoidance of doubt, the present invention also embraces prodrugs which react in vivo to give a compound of the present invention.

The compounds of the invention may be prepared by synthetic routes that will be apparent to those skilled in the art, e.g. based on the Examples.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation.

An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by coadministration with another chemotherapeutic or antineoplastic agent. The compound of the invention and the said other agent may be administrated in any order. In both these cases the compound of the invention and the other agent may be administered together or, if separately, in any order as determined by a physician.

The PI3K inhibitors of the present invention may also be used to treat abnormal cell proliferation due to insults to body tissue during surgery in a human patient. These insults may arise as a result of a variety of surgical procedures such as joint surgery, bowel surgery, and cheloid scarring. Diseases that produce fibrotic tissue that may be treated using the PI3K inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using PI3K inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Osler-Weber-Rendu syndrome.

Examples of diseases associated with uncontrolled angiogenesis that may be treated according to the present invention include, but are not limited to retinal/choroidal neovascularisation and corneal neovascularisation. Examples of diseases which include some component of retinal/choroidal neovascularisation include, but are not limited to, Best's diseases, myopia, optic pits, Stargart's diseases, Paget's disease, vein occlusion, artery occlusion, sickle cell anaemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularisation of the angle) and diseases caused by the abnormal proliferation of fibrovascular or fibrous tissue including all forms of proliferative vitreoretinopathy. Examples of corneal neovascularisation include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using PI3K inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a PI3K inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterised by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterised by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by PI3K inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using PI3K inhibitors according to the present invention to inhibit angiogenesis, such granulomas formation can be inhibited. Psoriasis, also a chronic and recurrent inflammatory disease, is characterised by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterised by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using PI3K inhibitors according to the present invention alone or in conjunction with other anti-RA agents may prevent the formation of new blood vessels necessary to maintain the chronic inflammation.

Preferably, the condition is cancer, notably leukaemias including chronic myelogenous leukaemia and acute myeloid leukaemia, lymphomas, solid tumours, and PTEN-negative tumours including PTEN-negative haematological, breast, lung, endometrial, skin, brain and prostate cancers (where PTEN refers to "phosphatise and tensin homolog deleted on chromosome 10"). More preferably, the condition to be treated in a patient in need thereof by administering an effective amount of a disclosed compound is a disorder selected from rheumatoid arthritis, asthma, chronic obstructive pulmonary disease (COPD), multiple sclerosis, psoriasis and other inflammatory skin disorders, systemic lupus erythematosus, inflammatory bowel disease, and organ transplant rejection. For example, provided herein is a method of treating a patient suffering a disorder selected from the group consisting leukaemias (including e.g., chronic myelogenous leukaemia and acute myeloid leukaemia), lymphoma, a solid tumour cancer such as breast, lung, or prostate cancer, PTEN-negative tumours including PTEN-negative haematological, breast, lung, endometrial, skin, brain and prostate cancers (where PTEN refers to "phosphatise and tensin homolog deleted on chromosome 10") comprising administering an effective amount of a disclosed compound.

The invention will now be illustrated by the following Examples.

EXAMPLES

Nomenclature: Compounds were named using Marvin-sketch 6.3.0 or higher

Analytical conditions: All $^1$H NMR were obtained at 300 or 400 MHz; $^{19}$F NMR NMR were obtained at 282 MHz.

Abbreviations:

| | | |
|---|---|---|
| rt room temperature | h hour | |
| s singlet | d doublet | |
| t triplet | q quartet | |
| br broad | m multiplet | |
| eq equivalent | min minute | |
| ES$^+$ electrospray positive ionisation | MS mass spectrometry | |
| ES$^-$ electrospray negative ionisation | | |

INTERMEDIATES AND EXAMPLES

Intermediate 1

Ethyl-3-amino-5-bromofuro[2,3-b]pyridine-2-carboxylate

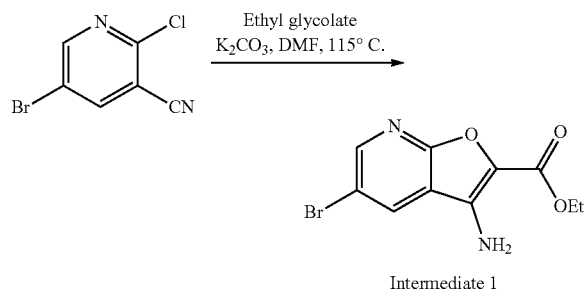

Intermediate 1

To a 10 L flask under N$_2$(g) was added 5-bromo-2-chloropyridine-3-carbonitrile (435 g, 2.0 mol, 1 eq), DMF (2.8 L) and potassium carbonate (553 g, 4.0 mol, 2 eq). This was followed by the addition of ethyl glycolate (208.2 mL, 2.2 mol, 1.1 eq). The reaction mixture was heated to 115° C. overnight. Upon completion, the reaction mixture was cooled to rt and water (13.1 L) was added, this led to the formation of a precipitate. The mixture was stirred for 20 mins, then filtered. The resulting brown solid was dried at 50° C., slurried in Et$_2$O/heptane (9:1, 2.8 L) and filtered to give 405.6 g. Further purification via soxhlet extraction using TBME (4.5 L) yielded Intermediate 1 as a yellow solid (186 g, 34%). This procedure was repeated twice.

$^1$H NMR (400 MHz, CDCl$_3$) $\delta_H$: 8.53 (d, J=2.0 Hz, 1H), 8.07 (d, J=2.0 Hz, 1H), 5.00 (br s, 2H), 4.44 (q, J=7.0 Hz, 2H), 1.44 (t, J=7.0 Hz, 3H).

MS (ES$^+$) 309 (100%, [M+Na]$^+$), 307 (100%, [M+Na]$^+$).

Intermediate 2

12-Bromo-8-oxa-3,5,10-triazatricyclo[7.4.0.0$^{2,7}$]trideca-1(9),2(7),10,12-tetraene-4,6-dione

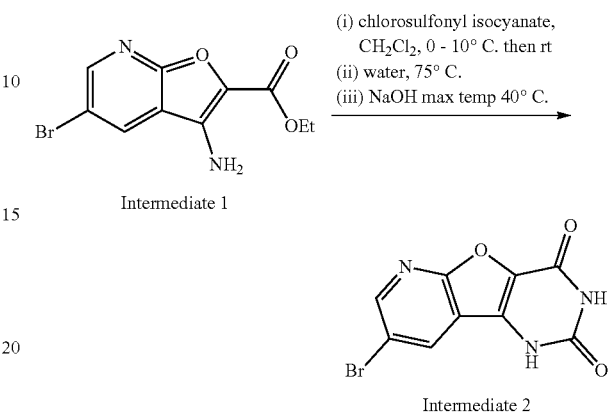

Intermediate 2

To Intermediate 1 (239.0 g, 0.84 mol, 1 eq) dissolved in CH$_2$Cl$_2$ (5.5 L) was added chlorosulfonyl isocyanate (87.6 mL, 1.0 mol, 1.2 eq) dropwise at 0-10° C. The resulting reaction mixture was stirred for 30 min, stripped to dryness and the resulting solid ground to a fine powder. Water (5.5 L) was added to the solid and the suspension was heated at 75° C. for 1 h. After cooling to rt, solid NaOH (335 g, 8.4 mol, 10 eq) was added allowing the reaction mixture to exotherm (maximum temperature 40° C.). The reaction was cooled to 0-10° C. and the pH adjusted to 5-6 using 5M HCl (~1 L). The reaction mixture was stirred for 30 mins, then filtered. The solid was washed with water (2.3 L) and pulled dry. Further drying in a vacuum oven at 40° C. yielded Intermediate 2 as a brown solid (193 g, 76%). This procedure was repeated twice.

$^1$H NMR (400 MHz, DMSO-d$_6$) $\delta_H$: 12.01 (br s, 1H), 11.58 (br s, 1H), 8.72 (d, J=2.0 Hz, 1H), 8.59 (d, J=2.0 Hz, 1H).

MS (ES$^-$) 282 (100%, [M+H]$^+$).

Intermediate 3

12-Bromo-4,6-dichloro-8-oxa-3,5,10-triazatricyclo[7.4.0.0$^{2,7}$]trideca-1(9),2(7),3,5,10,12-hexaene

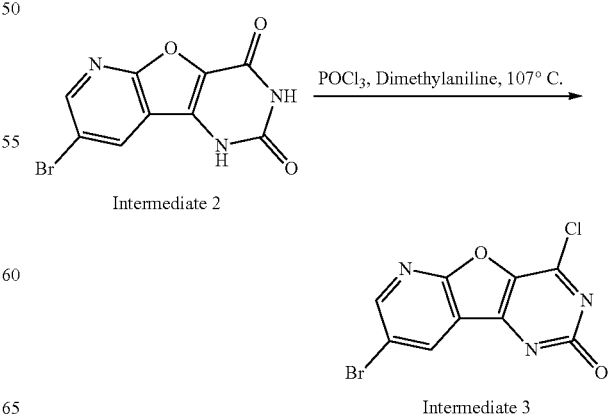

Intermediate 3

To Intermediate 2 (387 g, 1.27 mol, 1 eq) was added POCl₃ (6.07 L) and N,N-dimethylaniline (348 mL, 2.8 mol, 2.2 eq). The reaction mixture was heated at 107° C. for 10 h. Once cooled to rt, solvent was removed in vacuo azeotroping with toluene (3×3.9 L). The resulting residue was partitioned between CH₂Cl₂ (12.8 L) and water (3.9 L) and the phases separated. The organic phase was washed with water (2×3.9 L). The combined aqueous phase was back-extracted with CH₂Cl₂ (7.7 L) and the combined organics dried over MgSO₄, filtered and stripped to yield Intermediate 3 as brown solid (429 g, ~quant.).

$^1$H NMR (400 MHz, CDCl₃) δ$_H$: 8.78 (d, J=2.5 Hz, 1H), 8.72 (d, J=2.5 Hz, 1H).

Intermediate 4

12-Bromo-4-chloro-6-(morpholin-4-yl)-8-oxa-3,5,10-triazatricyclo[7.4.0.0$^{2,7}$]trideca-1(9),2(7),3,5,10,12-hexaene

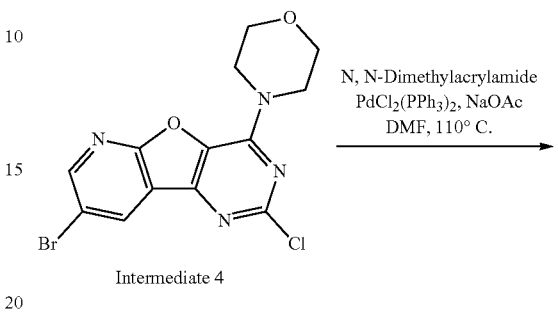

Intermediate 3

To Intermediate 3 (419.3 g, 1.32 mol, 1 eq) in MeOH (8.6 L) was added morpholine (259 mL, 2.90 mol, 2.2 eq) at rt. After stirring the reaction mixture for 2 h, water (0.8 L) was added. It was then cooled to 0-5° C. and stirred for an additional 30 mins. The resulting solid was filtered, washed with water (5.2 L) and pulled dry. Further purification by silica gel column chromatography with CH₂Cl₂/EtOAc (1:0-9:1) yielded Intermediate 4 (419 g, 84%).

$^1$H NMR (400 MHz, CDCl₃) δ$_H$: 8.66 (d, J=2.0 Hz, 1H), 8.62 (d, J=2.0 Hz, 1H), 4.07-4.21 (m, 4H), 3.85-3.91 (m, 4H).

MS (ES⁺) 393 (100%, [M+Na]⁺), 391 (80%, [M+Na]⁺).

Intermediate 5

(2E)-3-[4-Chloro-6-(morpholin-4-yl)-8-oxa-3,5,10-triazatricyclo[7.4.0.0$^{2,7}$]trideca-1(9),2(7),3,5,10,12-hexaen-12-yl]-N,N-dimethylprop-2-enamide

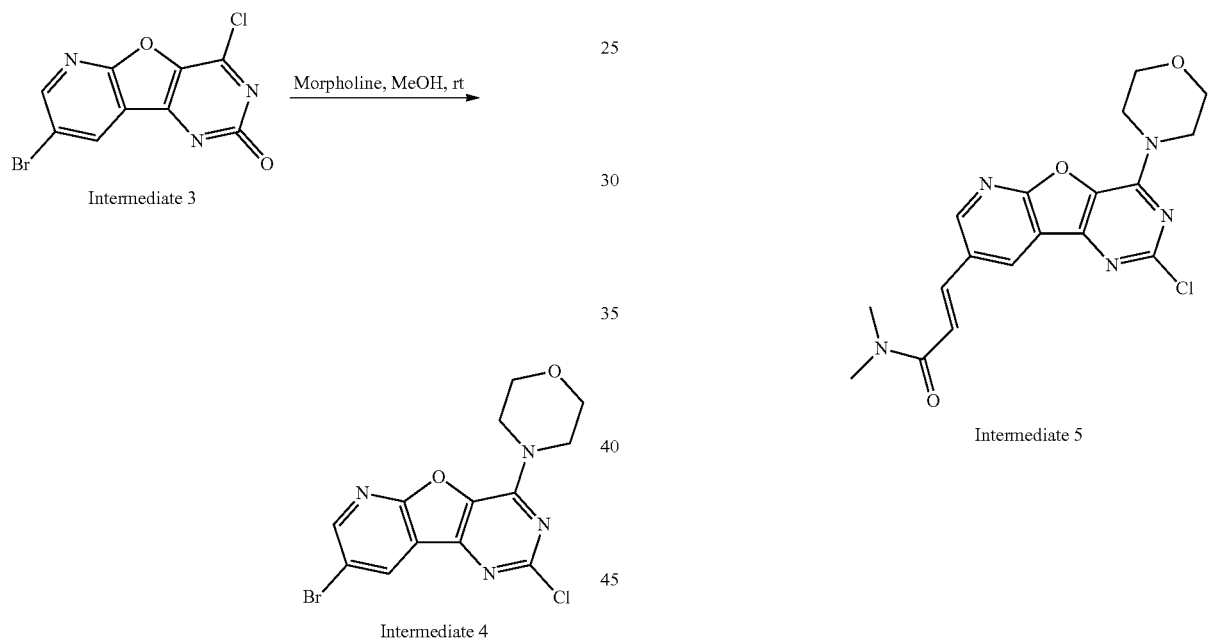

To Intermediate 4 (60 g, 0.15 mol, 1 eq) was added N,N-dimethylacrylamide (16.7 mL, 0.15 mol, 1 eq), PdCl₂(PPh₃)₂ (3.4 g, 4.5 mmol, 0.03 eq) and NaOAc (40 g, 0.45 mol, 3 eq) in DMF (1.2 L). The reaction mixture was heated at 110° C. for 7 h. This process was repeated 3 times and batches combined. Once cooled down to rt, solvent was removed in vacuo and the resulting residue was partitioned between CH₂Cl₂ (6.5 L) and water (5.5 L). The phases were separated and the aqueous phase was extracted with CH₂Cl₂ (2×4 L). The combined organics were washed with brine (2×4 L), dried over MgSO₄, filtered and stripped. The resulting solid was slurried in EtOAc/heptane (1:1, 0.8 L) for 30 mins, filtered, and washed with EtOAc/heptane (1:1, 2×450 mL). Further drying in a vacuum oven at 40° C. yielded the Intermediate 5 as an orange solid (203.0 g, 86%).

$^1$H NMR (400 MHz, CDCl₃) δ$_H$: 8.70 (s, 2H), 7.82 (d, J=15.6 Hz, 1H), 7.07 (d, J=15.6 Hz, 1H), 4.11-4.19 (m, 4H), 3.85-3.93 (m, 4H), 3.22 (s, 3H), 3.11 (s, 3H).

MS (ES⁺) 388 (100%, [M+H]⁺).

Intermediate 6

4-Chloro-6-(morpholin-4-yl)-8-oxa-3,5,10-triazatricyclo[7.4.0.0²,⁷]trideca-1(9),2(7),3,5,10,12-hexaene-12-carbaldehyde

Intermediate 7

4-(1H-Indol-4-yl)-6-(morpholin-4-yl)-8-oxa-3,5,10-triazatricyclo[7.4.0.0²,⁷]trideca-1(9),2,4,6,10,12-hexaene-12-carbaldehyde

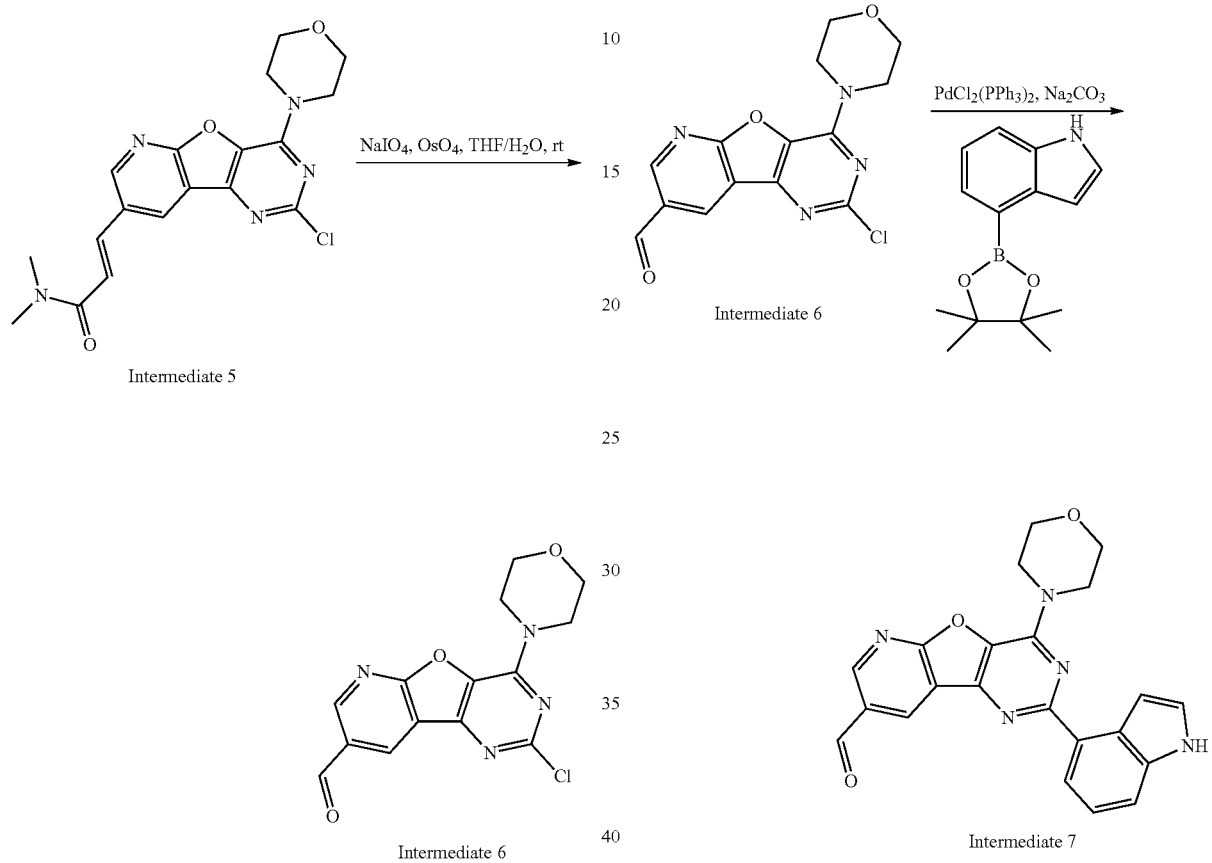

Intermediate 5 (124.0 g, 0.39 mol, 1 eq) was dissolved in THF (12.4 L) at 65° C. Once cooled to 35° C., water (4.1 L), NaIO₄ (205.4 g, 1.17 mol, 3 eq) and OsO₄ (2.5 wt % in ᵗBuOH, 80.3 mL, 2%) were added. The reaction mixture was stirred at rt for 60 h. The reaction mixture was cooled to 0-5° C., stirred for 30 mins then filtered. The solid was washed with water (545 mL) and pulled dry. The crude product was combined with two further batches (2×118.3 g scale) and slurried in water (6.3 L) for 30 mins at rt. The solids were filtered, washed with water (1.6 L) and pulled dry. Further drying in a vacuum oven yielded Intermediate 6 as a pink solid (260 g, 88%)

¹H NMR (400 MHz, CDCl₃/MeOD, 9:1) $\delta_H$: 10.13 (s, 1H), 9.04 (d, J=2.0 Hz, 1H), 8.91 (d, J=2.0 Hz, 1H), 3.99-4.13 (m, 4H), 3.73-3.84 (m, 4H).

MS (ES⁺) 351 (100%, [M+MeOH+H]⁺).

To Intermediate 6 (164.4 g, 0.52 mol, 1 eq) was added indole-4-boronic acid pinacol ester (376.0 g, 1.55 mol, 3 eq), PdCl₂(PPh₃)₂ (72.0 g, 0.10 mol, 0.2 eq) and sodium carbonate (110.2 g, 1.04 mol, 2 eq) in dioxane (16.4 L)/water (5.8 L). The reaction mixture was refluxed for 1 h. It was then cooled to 60-70° C. Water (9.8 L), brine (4.9 L) and EtOAc (9.5 L) were added. The phases were separated and the aqueous phase extracted with EtOAc (3×9.5 L) at 60-65° C. The combined organics were dried over MgSO₄, filtered and stripped. The resulting solid was slurried in CH₂Cl₂ (4.8 L) for 30 mins, filtered, washed with CH₂Cl₂ (3×238 mL) and pulled dry. Further drying in a vacuum oven at 40° C. yielded Intermediate 7 as a yellow solid (135.7 g, 66%).

¹H NMR (300 MHz, CDCl₃) $\delta_H$: 11.27 (br s, 1H), 10.26 (s, 1H), 9.16 (d, J=2.3 Hz, 1H), 9.11 (d, J=2.3 Hz, 1H), 8.18 (d, J=7.5 Hz, 1H), 7.58-7.67 (m, 2H), 7.49 (t, J=2.8 Hz, 1H), 7.23 (t, J=7.7 Hz, 1H), 4.08-4.16 (m, 4H), 3.83-3.90 (m, 4H).

MS (ES⁺) 432.0 (100%, [M+MeOH+H]⁺).

Intermediate 8

4-{[4-chloro-6-(morpholin-4-yl)-8-oxa-3,5,10-triaza-tricyclo[7.4.0.0²,⁷]trideca-1(13),2(7),3,5,9,11-hexaen-12-yl]methyl}-1λ⁴-thiomorpholin-1-one

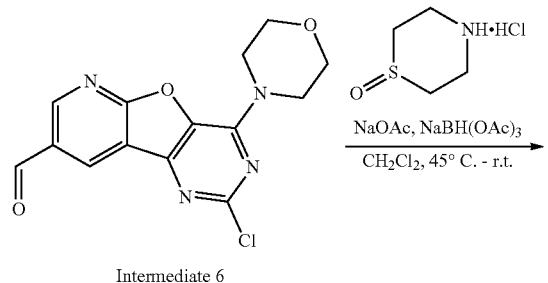

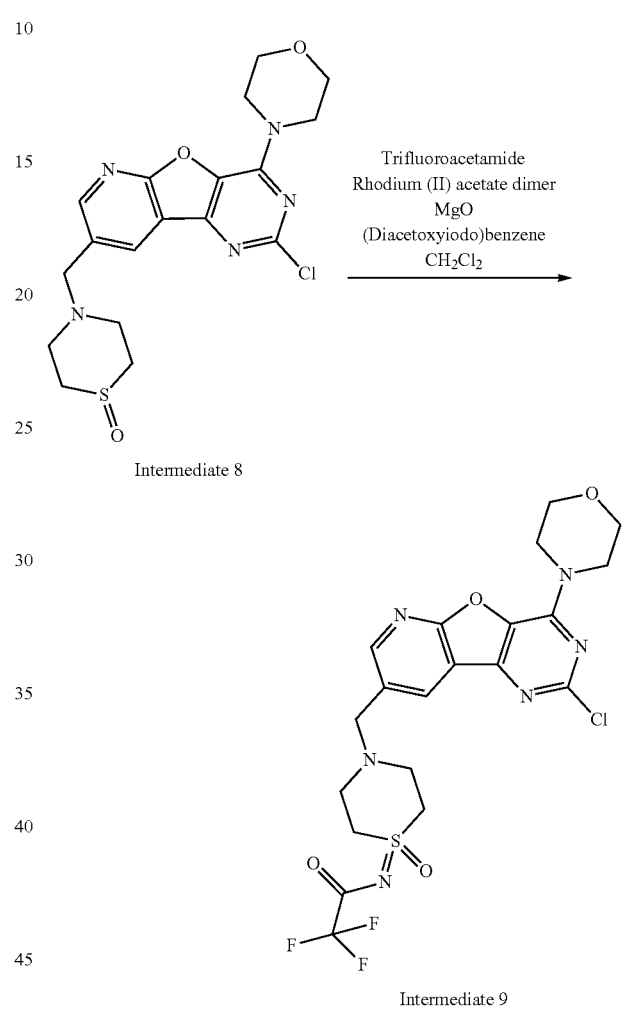

Intermediate 9

N-(4-{[4-Chloro-6-(morpholin-4-yl)-8-oxa-3,5,10-triazatricyclo[7.4.0.0²,⁷]trideca-1(13),2,4,6,9,11-hexaen-12-yl]methyl}-1-oxo-1λ⁶-thiomorpholin-1-ylidene)-2,2,2-trifluoroacetamide To Intermediate 6 (2.77 g, 8.7 mmol, 1 eq), 1λI-thiomorpholin-1-one hydrochloride (1.62 g, 10.4 mmol, 1.2 eq) and NaOAc (853 mg, 10.4 mmol, 1.2 eq) in anhydrous $CH_2Cl_2$ (200 mL) was added $NaBH(OAc)_3$ (2.94 g, 13.9 mmol, 1.6 eq). The reaction mixture was stirred at rt overnight. Then, it was partitioned with 1N NaOH (50 mL) and $H_2O$ (50 mL), and extracted with $CH_2Cl_2$ (3×20 mL). The combined organic extracts were dried over $MgSO_4$, filtered and the solvent was removed in vacuo. Purification by silica gel column chromatography with EtOAc/MeOH (1:0-9:1), then $CH_2Cl_2$/MeOH (1:0-4:1) yielded Intermediate 8 as a white solid (2.48 g, 68%).

¹H NMR (300 MHz, DMSO-d₆) δ$_H$: 8.62 (d, J=2.1 Hz, 1H), 8.51 (d, J=2.3 Hz, 1H), 4.00 (m, 4H), 3.74-3.84 (m, 6H), 2.83-3.00 (m, 4H), 2.61-2.81 (m, 4H).

MS (ES⁺) 422.1 (100%, [M+H]⁺).

To a stirred solution of Intermediate 8 (0.155 g, 0.37 mmol) in $CH_2Cl_2$ (20 mL) at rt were added in single portions, trifluoroacetamide (0.084 g, 0.74 mmol), MgO (0.137 g, 3.4 mmol), and rhodium (II) acetate dimer (0.018 g, 0.04 mmol). (Diacetoxyiodo)benzene (0.179 g, 0.555 mmol) was added in a single portion. The reaction mixture was heated to 40° C. for 6.5 h. The reaction mixture was allowed to stand overnight, and then charged with fresh reagents and stirred for 6 h. The solvent was removed by evaporation in vacuo and the reaction mixture loaded on to a silica column and eluted with 5% MeOH/$CH_2Cl_2$ to give Intermediate 9 (0.06 g, 30% yield).

¹H NMR (300 MHz, DMSO-d₆) δ$_H$: 8.64 (d, J=1.9 Hz, 1H), 8.59 (d, J=1.9 Hz, 1H), 3.96-4.02 (m, 4H), 3.94 (s, 2H), 3.73-3.88 (m, 8H), 3.05-3.20 (m, 2H), 2.83-2.97 (m, 2H)

MS (ES⁺) 533.1 (54%, [M+H]⁺)

Intermediate 10

4-{[4-Chloro-6-(morpholin-4-yl)-8-oxa-3,5,10-triazatricyclo[7.4.0.0$^{2,7}$]trideca-1(13),2,4,6,9,11-hexaen-12-yl]methyl}-1-imino-1λ$^6$-thiomorpholin-1-one

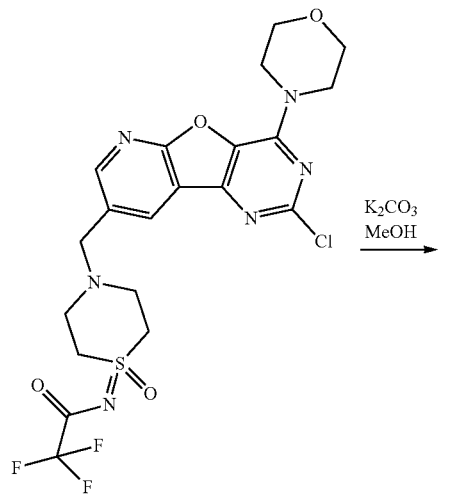

Intermediate 10

To a stirred solution of Intermediate 9 (0.10 g, 0.19 mmol) in MeOH (5 mL) at room temperature was added K$_2$CO$_3$ (0.138 g, 1 mmol) in a single portion. The reaction mixture was stirred for 1 h and then poured into saturated NaCl solution (20 mL) and extracted twice with CH$_2$Cl$_2$ (25 mL). The combined organic fractions were dried over MgSO$_4$, filtered and the solvent removed by evaporation in vacuo. Purification by flash silica column chromatography, 5% MeOH/CH$_2$Cl$_2$ elution, gave Intermediate 10 (0.076 g, 92%)

$^1$H NMR (300 MHz, DMSO-d$_6$) δ$_H$: 8.64 (d, J=1.9 Hz, 1H), 8.54 (d, J=2.1 Hz, 1H), 3.96-4.08 (m, 4H), 3.94 (s, 2H), 3.75-3.84 (m, 4H), 3.62 (br s, 1H), 2.78-3.10 (m, 8H)

MS (ES$^+$) 437.1 (100%, [M+H]$^+$)

Intermediate 11

(S)—N—[(1E)-[4-Chloro-6-(morpholin-4-yl)-8-oxa-3,5,10-triazatricyclo[7.4.0.0$^{2,7}$]trideca-1(13),2,4,6,9,11-hexaen-12-yl]methylidene]-2-methylpropane-2-sulfinamide

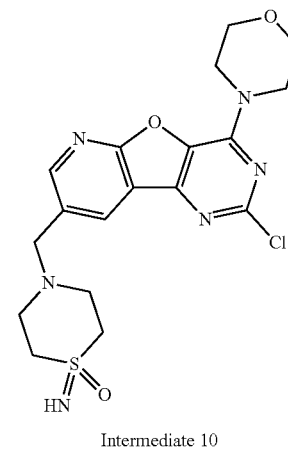

Intermediate 11

To a stirred suspension/solution of Intermediate 6 (0.319 g, 1 mmol) and (S)-2-methylpropane-2-sulfinamide (0.163 g, 1.35 mmol) in CH$_2$Cl$_2$ (50 mL) under an argon atmosphere at rt was added Ti(OiPr)$_4$ (0.59 mL, 2 mmol) dropwise. The reaction mixture was heated at reflux for 2 h and then Ti(OiPr)$_4$ (0.59 mL, 2 mmol) was added and heated for a further 2 h, where upon Ti(OiPr)$_4$ (0.59 mL, 2 mmol) was added and heated for a further 2 h. Upon cooling H$_2$O (2 mL) was added and the reaction mixture stirred for 10 min. The reaction mixture was filtered, dried over MgSO$_4$, filtered and the solvent removed by evaporation in vacuo. Purification by column chromatography (2% MeOH/CH$_2$Cl$_2$) followed by re-dissolving in CH$_2$Cl$_2$ and treatment with activated charcoal, filtration and removal of solvent by evaporation in vacuo gave Intermediate 11 as a white solid (0.268 g, 64% yield).

$^1$H NMR (300 MHz, DMSO-d$_6$) δ$_H$: 9.24 (d, J=2.1 Hz, 1H), 9.07 (d, J=2.1 Hz, 1H), 8.66 (s, 1H), 3.95-4.10 (m, 4H), 3.78-3.85 (m, 4H), 1.24 (s, 9H)

MS (ES$^+$) 422.0 (100%, [M+H]$^+$)

Intermediate 12

(S)—N—[(1R)-1-[4-Chloro-6-(morpholin-4-yl)-8-oxa-3,5,10-triazatricyclo[7.4.0.0$^{2,7}$]trideca-1(13),2,4,6,9,11-hexaen-12-yl]ethyl]-2-methylpropane-2-sulfinamide

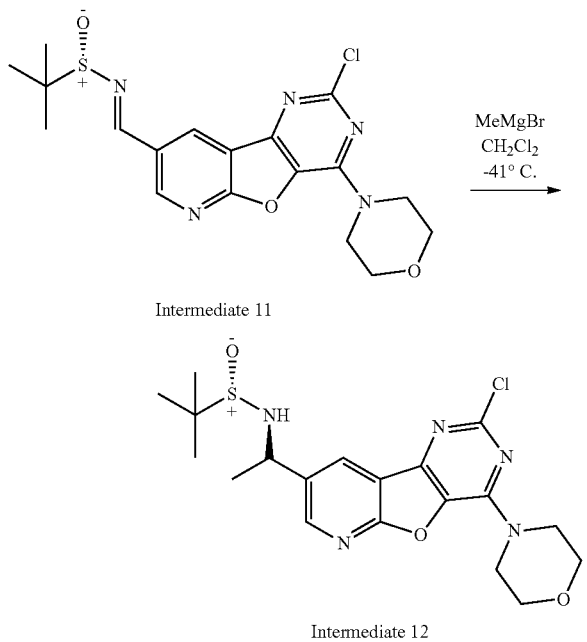

To a stirred solution of Intermediate 11 (0.262 g, 0.62 mmol) in CH$_2$Cl$_2$ (10 mL) at −41° C. under an argon atmosphere was added MeMgBr (3M, Et$_2$O, 0.45 mL, 1.364 mmol) dropwise. The reaction mixture was stirred at −41° C. for 3 hours and then allowed to warm to rt and stirred for 16 h. The reaction mixture was poured into saturated NH$_4$Cl solution (15 mL) and extracted twice with CH$_2$Cl$_2$ (15 mL). The combined organic fractions were dried over MgSO$_4$, filtered and the solvent removed by evaporation in vacuo. Purification by column chromatography first by 5% MeOH/CH$_2$Cl$_2$ elution and then a second column, EtOAc elution gave Intermediate 12 (0.105 g, 37% yield).

$^1$H NMR (300 MHz, DMSO-d$_6$) δ$_H$: 8.86 (m, 1H), 8.58 (d, J=2.1 Hz, 1H), 5.67 (d, J=6.0 Hz, 1H), 4.74 (br t, J=6.5 Hz, 1H), 3.95-4.07 (m, 4H), 3.74-3.84 (m, 4H), 1.59 (d, J=6.6 Hz, 3H), 1.11 (s, 9H)

MS (ES$^+$) 438.0 (100%, [M+H]$^+$)

Intermediate 13

(1R)-1-[4-Chloro-6-(morpholin-4-yl)-8-oxa-3,5,10-triazatricyclo[7.4.0.0$^{2,7}$]trideca-1(13),2,4,6,9,11-hexaen-12-yl]ethan-1-amine

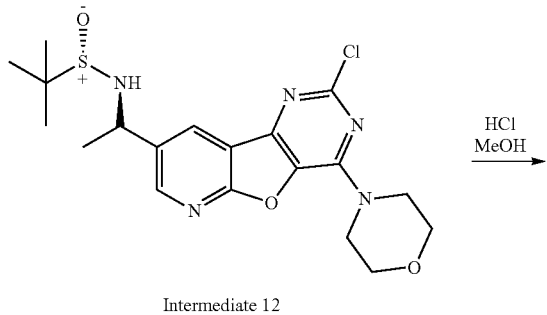

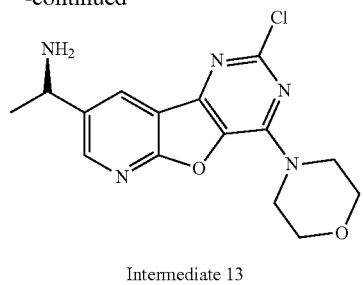

To a stirred solution of Intermediate 12 (0.10 g, 0.23 mmol) in MeOH (3 mL) at rt was added HCl (4M dioxane, 1 mL, 4 mmol) dropwise. The reaction mixture was stirred for 1 h and then poured into 10% NaOH solution (10 mL) and extracted twice with CH$_2$Cl$_2$ (10 mL). The combined organic fractions were dried over MgSO$_4$, filtered and the solvent removed by evaporation in vacuo. Purification by column chromatography, 10% MeOH/CH$_2$Cl$_2$ elution gave Intermediate 13 (0.60 g, 78%).

$^1$H NMR (300 MHz, DMSO-d$_6$) δ$_H$: 8.67 (d, J=2.1 Hz, 1H), 8.60 (d, J=2.1 Hz, 1H), 4.28 (q, J=6.6 Hz, 1H), 3.90-4.10 (m, 4H), 3.75-3.85 (m, 4H), 2.92 (br s, 2H), 1.38 (d, J=6.6 Hz, 3H)

MS (ES$^+$) 334.1 (100%, [M+H]$^+$)

Intermediate 14

4-[(1 R)-1-[4-Chloro-6-(morpholin-4-yl)-8-oxa-3,5,10-triazatricyclo[7.4.0.0$^{2,7}$]trideca-1(13),2,4,6,9,11-hexaen-12-yl]ethyl]-1λ$^6$-thiomorpholine-1,1-dione

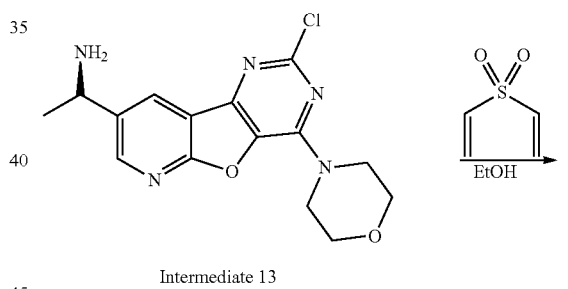

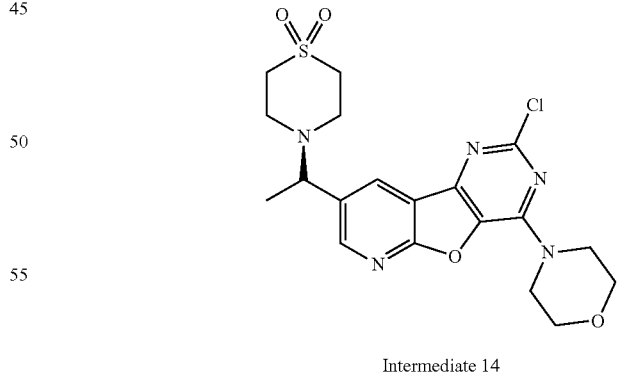

To a stirred solution of Intermediate 13 (0.066 g, 0.2 mmol) in EtOH (2 mL) at rt was added divinyl sulfone (0.024 g, 0.2 mmol) as a solution in EtOH (0.5 mL). The reaction mixture was heated to 80° C. for 3 h. The reaction mixture was allowed to cool to rt and left to stand for 16 h. The product was isolated by filtration, EtOH washed and dried in vacuo, to give Intermediate 14 (0.065 g, 72%).

¹H NMR (300 MHz, DMSO-d₆) δ_H: 8.70 (d, J=2.3 Hz, 1H), 8.59 (m, 1H), 4.21 (q, J=6.8 Hz, 1H), 3.97-4.06 (m, 4H), 3.75-3.83 (m, 4H), 3.05-3.15 (m, 4H), 2.69-2.99 (m, 4H), 1.47 (d, J=6.8 Hz, 3H)

MS (ES⁺) 452.1 (100%, [M+H]⁺)

Intermediate 15

(R)—N—[(1E)-[4-Chloro-6-(morpholin-4-yl)-8-oxa-3,5,10-triazatricyclo[7.4.0.0²,⁷]trideca-1(13),2,4,6,9,11-hexaen-12-yl]methylidene]-2-methylpropane-2-sulfinamide

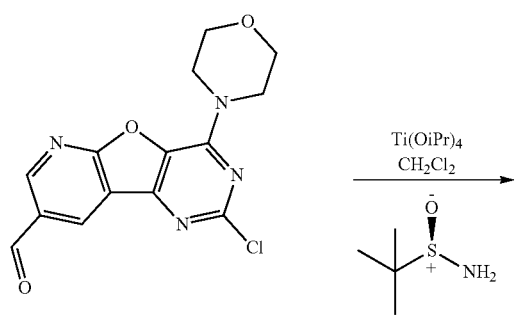

Intermediate 6

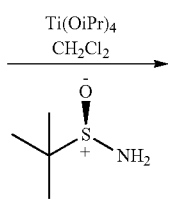

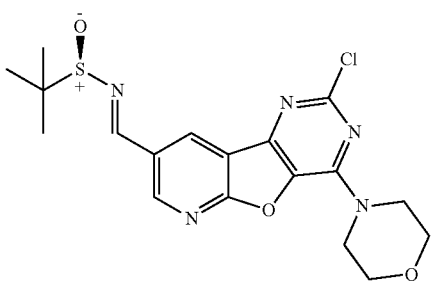

Intermediate 15

Intermediate 16

(R)-N-[(1S)-1-[4-Chloro-6-(morpholin-4-yl)-8-oxa-3,5,10-triazatricyclo[7.4.0.0²,⁷]trideca-1(13),2,4,6,9,11-hexaen-12-yl]ethyl]-2-methylpropane-2-sulfinamide

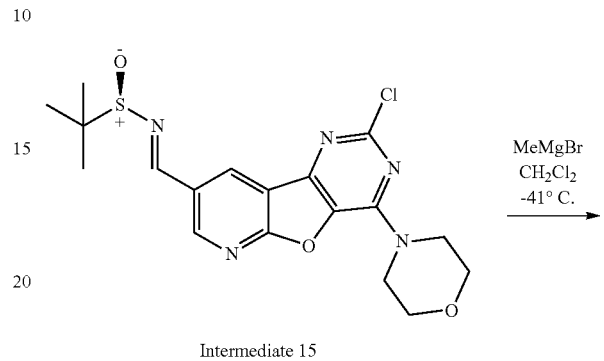

Intermediate 15

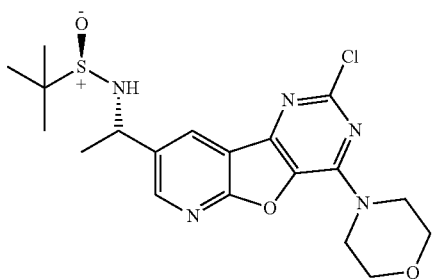

Intermediate 16

To a stirred suspension/solution of Intermediate 6 (0.319 g, 1 mmol) and (R)-2-methylpropane-2-sulfinamide (0.163 g, 1.35 mmol) in CH₂Cl₂ (50 mL) under an argon atmosphere at rt was added Ti(OiPr)₄ (0.59 mL, 2 mmol) dropwise. The reaction mixture was heated at reflux for 2 h and then Ti(OiPr)₄ (0.59 mL, 2 mmol) was added and heated for a further 2 h, where upon Ti(OiPr)₄ (0.59 mL, 2 mmol) was added and heated for a further 2 h. Upon cooling, H₂O (2 mL) was added and the reaction mixture stirred for 10 min. The reaction mixture was filtered, dried over MgSO₄, filtered and the solvent removed by evaporation in vacuo. Purification by column chromatography (2% MeOH/CH₂Cl₂) then redissolving in CH₂Cl₂ and treatment with activated charcoal, filtration and removal of solvent by evaporation in vacuo and then recrystalisation from MeOH gave Intermediate 15 as a white solid (0.242 g, 58%).

¹H NMR (300 MHz, DMSO-d₆) δ_H: 9.25 (m, 1H), 9.06 (m, 1H), 8.86 (s, 1H), 3.98-4.07 (m, 4H), 3.75-3.85 (m, 4H), 1.24 (s, 9H).

To a stirred solution of Intermediate 15 (0.203 g, 0.48 mmol), in CH₂Cl₂ (10 mL) under an argon atmosphere at −48° C. was added MeMgBr (3M Et₂O, 0.4 mL, 1.2 mmol) dropwise. The reaction mixture was stirred at −48° C. for 6 h and then allowed to warm to rt and stirred for a further 16 h. The reaction mixture was poured into saturated NH₄Cl solution (20 mL) and extracted twice with CH₂Cl₂ (20 mL). The combined organic fractions were dried over MgSO₄, filtered and the solvent removed by evaporation in vacuo. Purification by flash silica column chromatography, 5% MeOH/CH₂Cl₂ elution, gave Intermediate 16 (0.053 g, 25%).

¹H NMR (300 MHz, DMSO-d₆) δ_H: 8.68 (d, J=2.3 Hz, 1H), 8.58 (d, J=2.1 Hz, 1H), 5.67 (d, J=6.0 Hz, 1H), 4.74 (br t, J=6.2 Hz, 1H), 3.97-4.07 (m, 4H), 3.75-3.83 (m, 4H), 1.59 (d, J=6.8 Hz, 3H), 1.11 (s, 9H).

Intermediate 17

(1S)-1-[4-Chloro-6-(morpholin-4-yl)-8-oxa-3,5,10-triazatricyclo[7.4.0.0²,⁷]trideca-1(13),2,4,6,9,11-hexaen-12-yl]ethan-1-amine

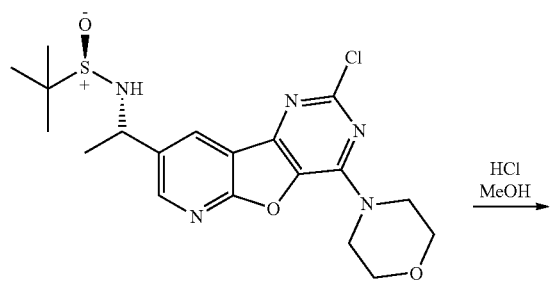

Intermediate 16

HCl
MeOH

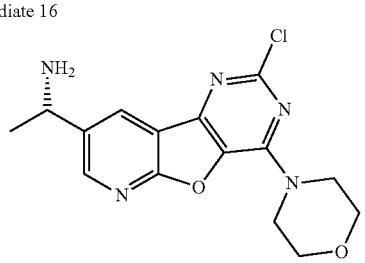

Intermediate 17

To a stirred solution of Intermediate 16 (0.05 g, 0.12 mmol) in MeOH (2 mL) at rt was added HCl (4M dioxane, 1 mL, 4 mmol) dropwise. The reaction mixture was stirred for 1 h and then poured into 10% NaOH solution (10 mL) and extracted twice with CH$_2$Cl$_2$ (10 mL). The combined organic fractions were dried over MgSO$_4$, filtered and the solvent removed by evaporation in vacuo. Purification by column chromatography, 10% MeOH/CH$_2$Cl$_2$ elution gave Intermediate 17 (0.38 g, 100%).

$^1$H NMR (300 MHz, DMSO-d$_6$) δ$_H$: 8.67 (d, J=2.1 Hz, 1H), 8.60 (d, J=2.1 Hz, 1H), 4.28 (q, J=6.6 Hz, 1H), 3.90-4.10 (m, 4H), 3.75-3.85 (m, 4H), 2.92 (br s, 2H), 1.38 (d, J=6.6 Hz, 3H).

MS (ES$^+$) 334.1 (100%, [M+H]$^+$)

Intermediate 18

4-[(1S)-1-[4-Chloro-6-(morpholin-4-yl)-8-oxa-3,5,10-triazatricyclo[7.4.0.0²,⁷]trideca-1(13),2,4,6,9,11-hexaen-12-yl]ethyl]-1λ⁶-thiomorpholine-1,1-dione

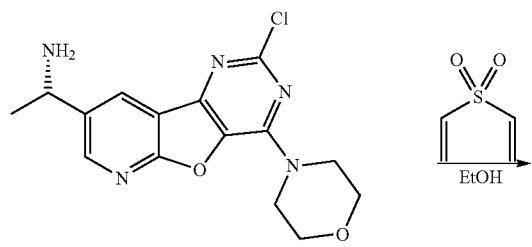

Intermediate 17

EtOH

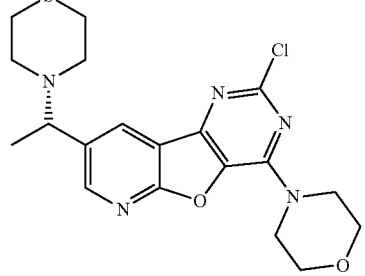

Intermediate 18

To a stirred solution Intermediate 17 (0.38 g, 0.114 mmol) in MeOH (5 mL), was added divinyl sulfone (0.013 g, 0.114 mmol) as a solution in MeOH (0.5 mL). The reaction mixture was heated to 60° C. for 8 h. Upon cooling the solvent was removed by evaporation in vacuo. Purification by column chromatography, 5% MeOH/CH$_2$Cl$_2$ gave Intermediate 18 (0.048 g, 92%).

$^1$H NMR (300 MHz, DMSO-d$_6$) δ$_H$: 8.70 (d, J=2.3 Hz, 1H), 8.59 (m, 1H), 4.21 (q, J=6.8 Hz, 1H), 3.93-4.05 (m, 4H), 3.74-3.83 (m, 4H), 3.03-3.15 (m, 4H), 2.74.2.98 (m, 4H), 1.48 (d, J=6.8 Hz, 3H).

MS (ES$^+$) 452.1 (100%, [M+H]$^+$)

Intermediate 19 tert-Butyl (2S,4R)-4-hydroxy-2-(hydroxymethyl)pyrrolidine-1-carboxylate

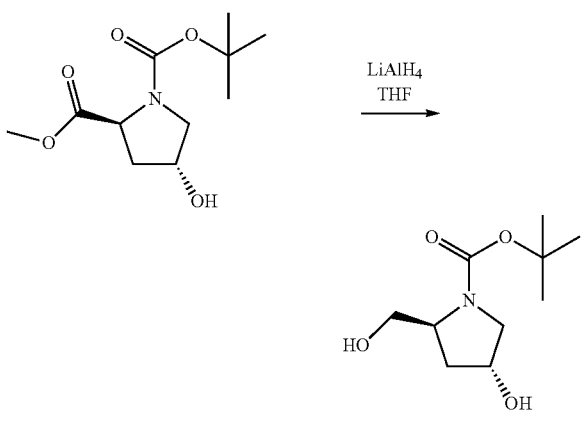

Intermediate 19

To a stirred solution of 1-tert-butyl 2-methyl (2S,4R)-4-hydroxypyrrolidine-1,2-dicarboxylate (5.0 g, 20.41 mmol) in THF (100 mL) under an argon atmosphere at −16° C. was added LiAlH$_4$ (1 M in THF, 21 mL, 21 mmol) dropwise over 5 min. A precipitate was formed that was broken up by the addition of THF (50 mL). The reaction mixture was stirred for 3.5 h, during which time the temperature was allowed to warm to 0° C. The reaction was quenched by the addition of EtOAc (5 mL), and stirred for 30 min. Excess Rochelles salt solution (100 mL) was carefully added and the reaction mixture allowed to warm to rt and stirred for a further 1 h. The product was isolate by extraction twice with CH$_2$Cl$_2$ (100 mL) and the combined organic fractions dried over MgSO$_4$, filtered and the solvent removed by evaporation in vacuo. Purification by column chromatography, 10% MeOH/CH$_2$Cl$_2$, gave Intermediate 19 in quantitative yield.

$^1$H NMR (300 MHz, DMSO-d$_6$) δ$_H$: 4.82 (br s, 1H), 4.64 (br d, J=5.5 Hz, 1H), 4.20 (sxt, J=4.2 Hz, 1H), 3.75 (br s, 1H), 3.16-3.50 (m, 4H), 1.85-2.02 (m, 1H), 1.80 (br s, 1H), 1.39 (s, 9H).

Intermediate 20 tert-Butyl(2S,4R)-4-(methanesulfonyloxy)-2-(methanesulfonyloxy)methyl]pyrrolidine-1-carboxylate

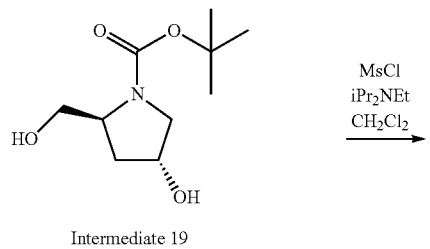

Intermediate 19

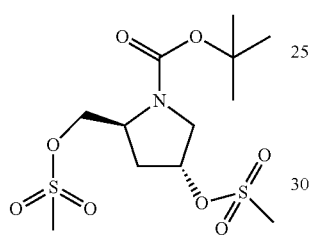

Intermediate 20

To a stirred solution of Intermediate 19 (4.663 g, 21 mmol) in CH$_2$Cl$_2$ (50 mL) at 0° C. was added iPr$_2$NEt (10 mL, 57.5 mmol) followed by dropwise addition of methanesulfonyl chloride (3.9 mL, 50.5 mmol). The reaction mixture was allowed to warm to rt and stirred for a further 4 h. More iPr$_2$NEt (10 mL, 57.5 mmol) followed by dropwise addition of methanesulfonyl chloride (3.9 mL, 50.5 mmol) were added and the reaction mixture stirred for a further 2 h. The reaction was quenched by careful addition of NaHCO$_3$ solution (50 mL). The product was isolated by extraction, twice, with CH$_2$Cl$_2$ (50 mL). The combined organic fractions were dried over MgSO$_4$, filtered and the solvent removed by evaporation in vacuo. Intermediate 20 was used without further purification in the next step.

Intermediate 21 tert-Butyl (1S,4S)-2-thia-5-azabicyclo[2.2.1]heptane-5-carboxylate

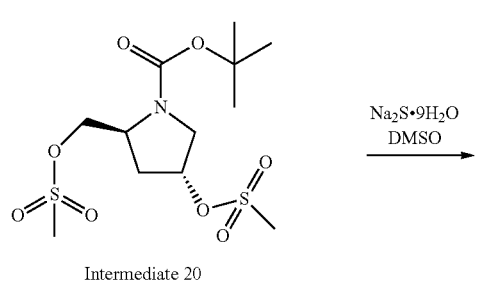

Intermediate 20

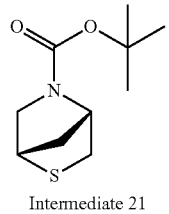

Intermediate 21

To a stirred solution of Intermediate 20 (7.83 g, 21 mmol) in DMSO (20 mL), was added sodium sulfide nonahydrate (5.04 g, 21 mmol), and the reaction mixture heated to 110° C. for 2 h. Upon cooling the reaction mixture was diluted with H$_2$O (120 mL), and EtOAc (120 mL). The organic layer was separated and the aqueous fraction further extracted with EtOAc (50 mL). The combined organic fractions were dried over MgSO$_4$, filtered and the solvent removed by evaporation in vacuo. Purification by column chromatography, 3:1 hexane/EtOAc, gave Intermediate 21 in 61% yield (2 steps), 2.734 g.

$^1$H NMR (300 MHz, DMSO-d$_6$) δ$_H$: 4.48 (br d, J=15.5 Hz, 1H), 3.68 (d, J=2.3 Hz, 1H), 3.42-3.53 (m, 1H), 2.88-3.01 (m, 2 H), 2.12 (br t, J=11.1 Hz, 1H), 1.73 (br d, J=10.2 Hz, 1H), 1.38 and 1.41 (s, 9H, amide rotamers).

Intermediate 22

(1S,4S)-2-Thia-5-azabicyclo[2.2.1]heptan-5-ium trifluoroacetate

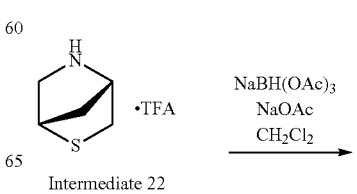

To a stirred solution of Intermediate 21 (0.108 g, 0.5 mmol) in CH$_2$Cl$_2$ (5 mL) at rt was added 1 ml TFA. The reaction mixture was stirred for 5 h and then the volatiles were removed by evaporation in vacuo. Intermediate 22 was used without further purification.

Intermediate 23

4-Chloro-6-(morpholin-4-yl)-12-[(1S,4S)-2-thia-5-azabicyclo[2.2.1]heptan-5-ylmethyl]-8-oxa-3,5,10-triazatricyclo[7.4.0.0$^{2,7}$]trideca-1(13),2,4,6,9,11-hexaene

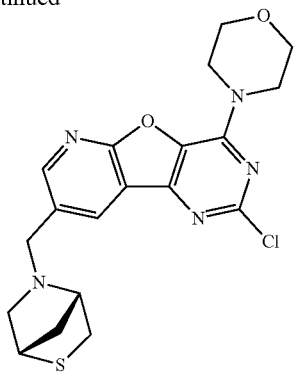

Intermediate 23

To a mixture of Intermediate 22 (0.115 g, 0.5 mmol), Intermediate 6 (0.160 g, 0.5 mmol), NaOAc (0.088 g, 1 mmol) and excess MgSO$_4$ was added CH$_2$Cl$_2$ (20 mL). The reaction mixture was stirred at rt for 5 h and then NaHB(OAc)$_3$ (1.5 mmol, 0.318 g) was added portion wise over 1 h. The reaction mixture was stirred for a further 2 h and then poured into H$_2$O (20 mL). The product was extracted twice with CH$_2$Cl$_2$ (20 mL). The combined organic fractions were dried over MgSO$_4$, filtered and the solvent removed by evaporation in vacuo. Purification by column chromatography, 5% MeOH/CH$_2$Cl$_2$, gave Intermediate 23 (0.086 g, 41%).

$^1$H NMR (300 MHz, DMSO-d$_6$) $\delta_H$: 8.62 (d, J=2.3 Hz, 1 H), 8.47 (d, J=2.1 Hz, 1 H), 3.91-4.07 (m, 6 H), 3.73-3.84 (m, 5 H), 3.50 (br s, 1 H), 3.07-3.14 (m, 2 H), 2.74-2.87 (m, 2 H), 2.18 (br d, J=10.0 Hz, 1 H), 1.71 (br d, J=10.2 Hz, 1 H)

MS (ES$^+$) 418.1 (100%, [M+H]$^+$)

Intermediate 24 tert-Butyl (1S,4S)-2,2-dioxo-2λ$^6$-thia-5-azabicyclo[2.2.1]heptane-5-carboxylate

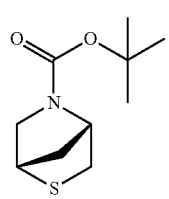

Intermediate 21

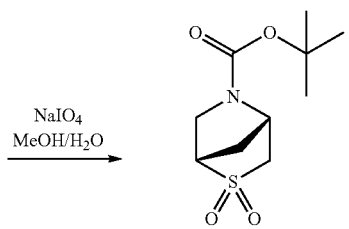

Intermediate 24

To a stirred solution of Intermediate 21 (0.215 g, 1 mmol) in MeOH (2 mL) at room temperature was added NaIO$_4$ (0.235 g, 1.1 mmol) as a solution in H$_2$O (2 mL) (exotherm). The reaction mixture was stirred for 1 h at rt, and then filtered and the solvent removed by evaporation in vacuo. The reaction mixture was dissolved in CH$_2$Cl$_2$ (10 mL) and poured into H$_2$O (10 mL). the product was extracted with CH$_2$Cl$_2$ (10 mL), EtOAc (10 mL) and CH$_2$Cl$_2$ (10 mL). The combined organic fractions were dried over MgSO$_4$, filtered and the solvent removed by evaporation in vacuo. Purification by flash silica column chromatography, 5% MeOH/ CH$_2$Cl$_2$ elution gave a mixture of sulfoxide isomers, 0.236 g. This mixture was re-dissolved in a mixture of MeOH (10 mL) and H$_2$O (10 mL). NaIO$_4$ (1.1 mmol, 0.235 g) was added and the reaction mixture heated to 60° C. for 16 h. The solvent was removed by evaporation in vacuo, and the reaction mixture re-dissolved in H$_2$O (10 mL) and CH$_2$Cl$_2$ (10 mL). The product was extracted twice with CH$_2$Cl$_2$ (10 mL), the combined organic fractions were dried over MgSO$_4$, filtered and the solvent removed by evaporation in vacuo. Purification by flash silica column chromatography, EtOAc elution, gave Intermediate 24 in 55% yield, 0.137 g.

MS (ES$^+$) 270.1 (100%, [M+Na]$^+$), 192.1 (40%, [M+H-tBu]$^+$)

Intermediate 25

(1S,4S)-2λ$^6$-Thia-5-azabicyclo[2.2.1]heptane-2,2-dione hydrochloride

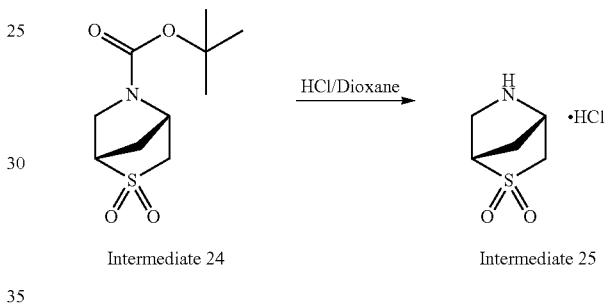

To a stirred solution of Intermediate 24 (0.137 g, 0.55 mmol) in dioxane (3mL) at rt was added HCl (2M dioxane, 3 mL, 6 mmol). The reaction mixture was stirred for 2.5 h and then the solvent removed by evaporation in vacuo. Intermediate 25 was used without further purification.

MS (ES$^+$) 148.1 (100%, [M+H]$^+$).

Intermediate 26

(1S,4S)-5-{[4-Chloro-6-(morpholin-4-yl)-8-oxa-3,5,10-triazatricyclo[7.4.0.0$^{2,7}$]trideca-1(13),2,4,6,9,11-hexaen-12-yl]methyl}-2λ$^6$-thia-5-azabicyclo[2.2.1]heptane-2,2-dione

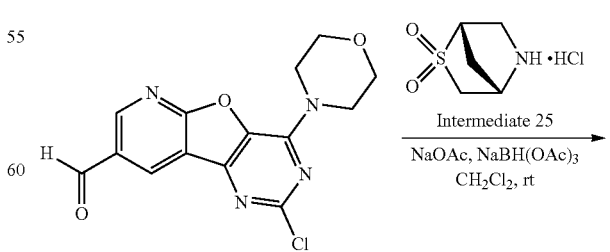

43

-continued

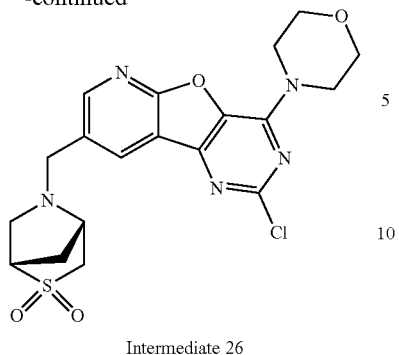

Intermediate 26

To a stirred solution of Intermediate 6 (0.21 g, 0.66 mmol) in CH$_2$Cl$_2$ (15 mL) was added excess MgSO$_4$, Intermediate 25 (0.112 g, 0.657 mmol) and NaOAc (0.108 g, 1.3 mmol). The reaction mixture was stirred for 2 h. NaHB(OAc)$_3$ (0.415 g, 1.959 mmol) was added in a single portion. The reaction mixture was stirred for 4 h at rt. The reaction mixture was poured into saturated NH$_4$Cl solution (20 mL) and extracted twice with CH$_2$Cl$_2$ (20 mL). The combined organic fractions were dried over MgSO$_4$, filtered and the solvent removed by evaporation in vacuo. Purification by flash silica column chromatography, 5% MeOH/CH$_2$Cl$_2$ elution, gave Intermediate 26 (0.184 g, 62%).

$^1$H NMR (300 MHz, DMSO-d$_6$) $\delta_H$: 8.64 (d, J=2.1 Hz, 1H), 8.51 (d, J=1.9 Hz, 1H), 4.01 (m, 6H), 3.78 (m, 6H), 3.38 (dd, J=2.3, 1.3 Hz, 1H), 3.14 (m, 1H), 3.02 (m, 2H), 2.35 (m, 2H)

Intermediate 27

(1S,2R,4S)-5-[(tert-Butoxy)carbonyl]-2-thia-5-azabi-cyclo[2.2.1]heptan-2-ium-2-olate

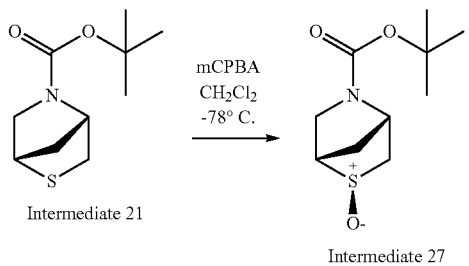

To a stirred solution of Intermediate 21 (0.645 g, 3 mmol) in CH$_2$Cl$_2$ (20 mL) under an argon atmosphere, at −78° C. was added mCPBA (77%, 0.759 g, 4.4 mmol) as a solution in CH$_2$Cl$_2$ (10 mL) dropwise. The reaction mixture was stirred for 2 h at −78° C. and then allowed to warm to rt and stirred for a further 2 h. The reaction mixture was poured into NaHCO$_3$ solution (20 mL) and extracted twice with CH$_2$Cl$_2$ (15 mL). The combined organic fractions were dried over MgSO$_4$, filtered and the solvent removed by evaporation in vacuo. Purification by column chromatography, 10% MeOH/EtOAc elution gave Intermediate 27 (0.455 g, 66%).

$^1$H NMR (300 MHz, DMSO-d$_6$) $\delta_H$: 4.48 (br s, 1H), 3.80 (m, 1H), 3.37 (m, 2H), 2.74 (d, J=13.2 Hz, 1H), 2.26 (m, 3H), 1.38 (s, 9H).

44

Intermediate 28

(1S,2R,4S)-2-Thia-5-azabicyclo[2.2.1]heptane-2,5-diium-2-olate trifluoroacetate

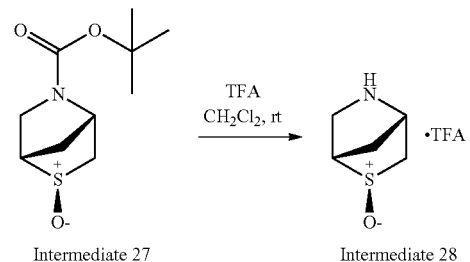

To a stirred of Intermediate 27 (0.20 g, 0.87 mmol) in CH$_2$Cl$_2$ (20 mL), at rt was added 2 mL of trfluoroacetic acid. The reaction mixture was stirred for 6 h and then the solvent and trifluoroacetic acid were removed by evaporation in vacuo to give Intermediate 28 which was used without further purification.

Intermediate 29

(1S,2R,4S)-5-{[4-Chloro-6-(morpholin-4-yl)-8-oxa-3,5,10-triazatricyclo[7.4.0.0$^{2,7}$]trideca-1(13),2,4,6,9,11-hexaen-12-yl]methyl}-2-thia-5-azabicyclo[2.2.1]heptan-2-ium-2-olate

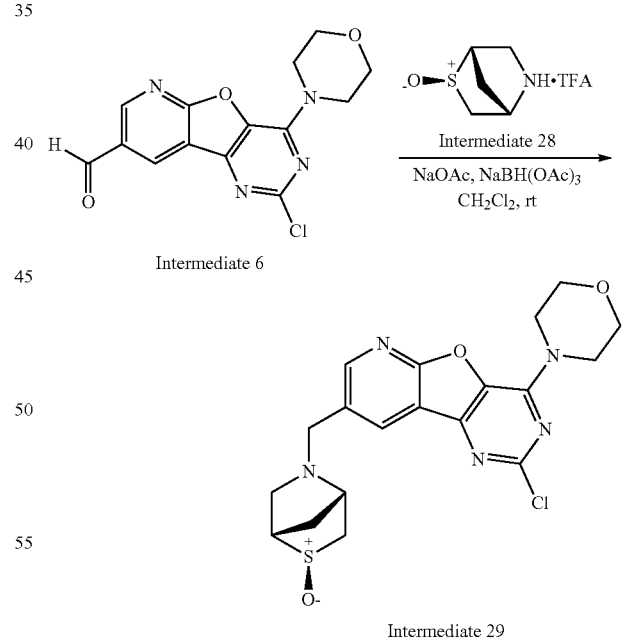

To a stirred solution of Intermediate 6 (0.159 g, 0.5 mmol) in CH$_2$Cl$_2$ (10 mL) was added excess MgSO$_4$, Intermediate 28 (0.245 g, 1 mmol) and NaOAc (0.82 g, 1 mmol). The reaction mixture was stirred for 2 h. NaHB(OAc)$_3$ (0.318 g, 1.5 mmol) was added in a single portion. The reaction mixture was stirred for 4 h at rt. The reaction mixture was poured into saturated NH$_4$Cl solution (20 mL) and extracted twice with CH$_2$Cl$_2$ (20 mL). The combined organic fractions were dried over MgSO$_4$, filtered and the solvent removed by evaporation in vacuo. Purification by flash silica column chromatography, 5% MeOH/CH$_2$Cl$_2$ elution, further purified by chromatography, 20% MeOH/EtOAc elution, followed by chromatography, 5% MeOH/CH$_2$Cl$_2$ gave Intermediate 29 (0.149 g, 69%).

$^1$H NMR (300 MHz, DMSO-d$_6$) δ$_H$: 8.58 (m, 1H), 8.44 (m, 1H), 4.02 (m, 6H), 3.7 (m, 9H), 2.98 (dd, J=4.5, 12.1 Hz, 1H), 2.19 (m, 3H), 1.99 (m, 2H), 1.72 (d, J=12.1, 1H), 1.17 (dt, J=2.1, 7.7 Hz, 2H).

Intermediate 30

Ethyl 3-amino-5-bromothieno[2,3-b]pyridine-2-carboxylate

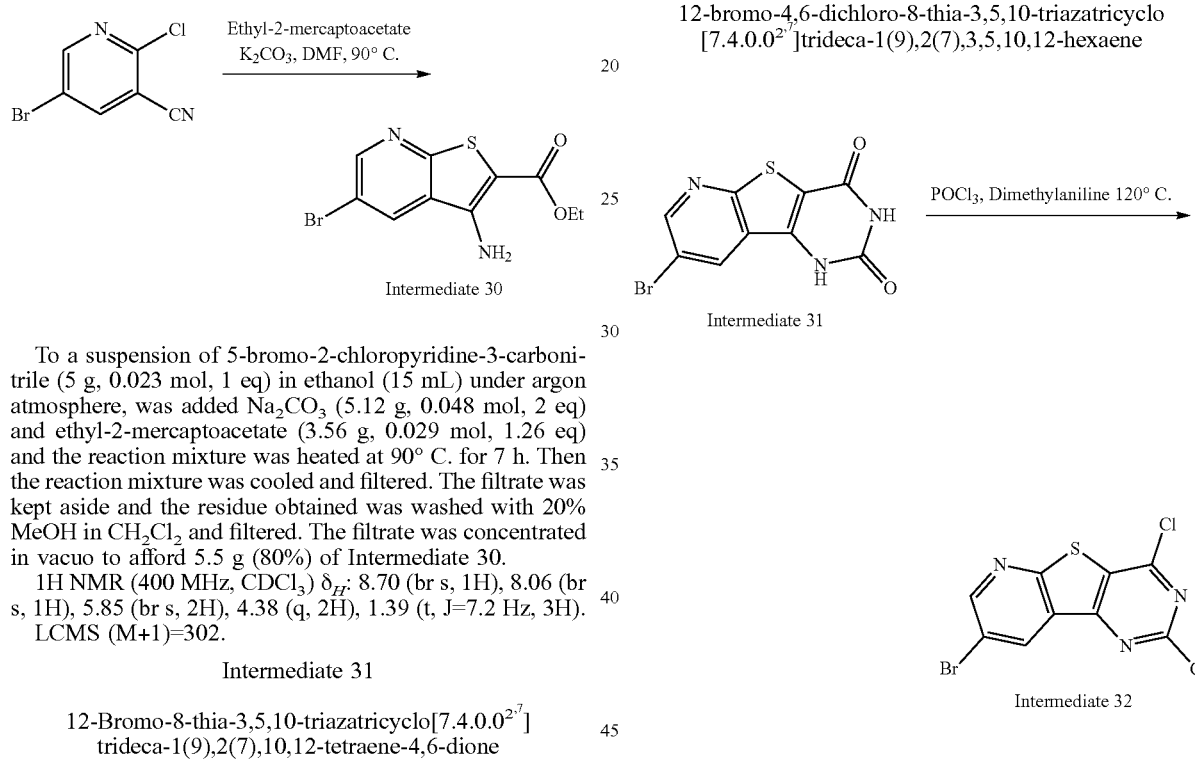

Intermediate 30

To a suspension of 5-bromo-2-chloropyridine-3-carbonitrile (5 g, 0.023 mol, 1 eq) in ethanol (15 mL) under argon atmosphere, was added Na$_2$CO$_3$ (5.12 g, 0.048 mol, 2 eq) and ethyl-2-mercaptoacetate (3.56 g, 0.029 mol, 1.26 eq) and the reaction mixture was heated at 90° C. for 7 h. Then the reaction mixture was cooled and filtered. The filtrate was kept aside and the residue obtained was washed with 20% MeOH in CH$_2$Cl$_2$ and filtered. The filtrate was concentrated in vacuo to afford 5.5 g (80%) of Intermediate 30.

1H NMR (400 MHz, CDCl$_3$) δ$_H$: 8.70 (br s, 1H), 8.06 (br s, 1H), 5.85 (br s, 2H), 4.38 (q, 2H), 1.39 (t, J=7.2 Hz, 3H). LCMS (M+1)=302.

Intermediate 31

12-Bromo-8-thia-3,5,10-triazatricyclo[7.4.0.0$^{2,7}$]trideca-1(9),2(7),10,12-tetraene-4,6-dione

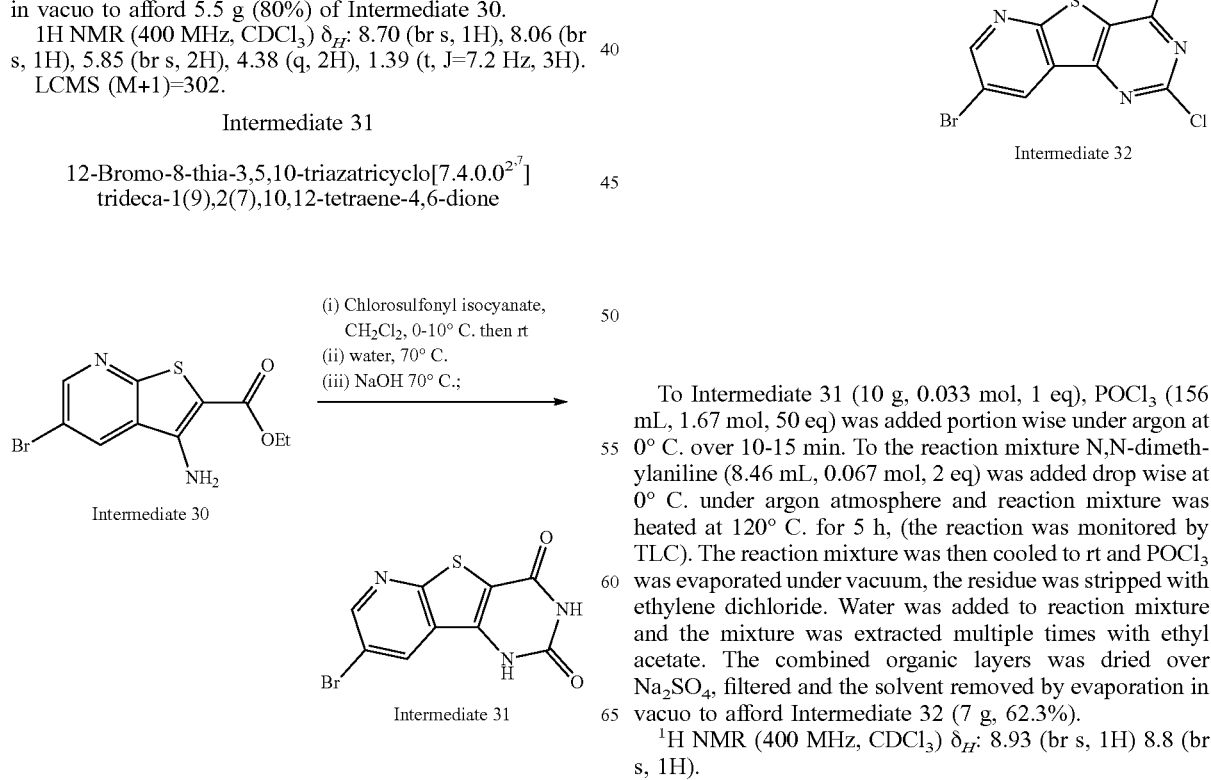

Intermediate 31

To a solution of Intermediate 30 (10 g, 0.033 mol, 1 eq) in CH$_2$Cl$_2$ (300 mL) under an argon atmosphere at 0° C. was added chlorosulfonylisocyanate (3.8 mL, 0.043 mol, 1.3 eq). The reaction mixture was allowed to warm to rt (over 2 h) and then concentrated in vacuo. To this mixture water (160 mL) was added and heated at 70° C. for 4 h. Then the reaction mixture was cooled to rt and NaOH (13 g, 0.32 mol, 20 eq) was added and reaction mixture was heated at 70° C. for 2 h. After completion of the reaction, the pH of the reaction mixture was adjusted to 6 using 1M HCl. The solid obtained were filtered through a Buchner funnel and washed with water (300 mL) and MeOH (300 mL), dried well under reduced pressure to yield 4.4 g (45%) of Intermediate 31.

1H NMR (400 MHz, CDCl3) δ$_H$: 8.97 (s, 1H) 8.90 (s, 1H).

Intermediate 32

12-bromo-4,6-dichloro-8-thia-3,5,10-triazatricyclo[7.4.0.0$^{2,7}$]trideca-1(9),2(7),3,5,10,12-hexaene Intermediate 32

To Intermediate 31 (10 g, 0.033 mol, 1 eq), POCl$_3$ (156 mL, 1.67 mol, 50 eq) was added portion wise under argon at 0° C. over 10-15 min. To the reaction mixture N,N-dimethylaniline (8.46 mL, 0.067 mol, 2 eq) was added drop wise at 0° C. under argon atmosphere and reaction mixture was heated at 120° C. for 5 h, (the reaction was monitored by TLC). The reaction mixture was then cooled to rt and POCl$_3$ was evaporated under vacuum, the residue was stripped with ethylene dichloride. Water was added to reaction mixture and the mixture was extracted multiple times with ethyl acetate. The combined organic layers was dried over Na$_2$SO$_4$, filtered and the solvent removed by evaporation in vacuo to afford Intermediate 32 (7 g, 62.3%).

$^1$H NMR (400 MHz, CDCl$_3$) δ$_H$: 8.93 (br s, 1H) 8.8 (br s, 1H).

Intermediate 33

12-Bromo-4-chloro-6-(morpholin-4-yl)-8-thia-3,5,10-triazatricyclo[7.4.0.0²,⁷]trideca-1(9),2(7),3,5,10,12-hexaene

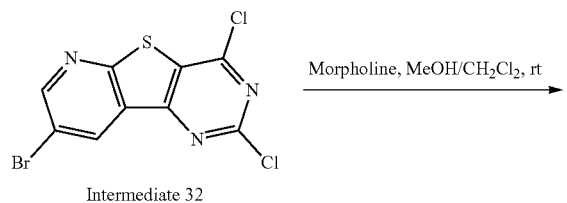

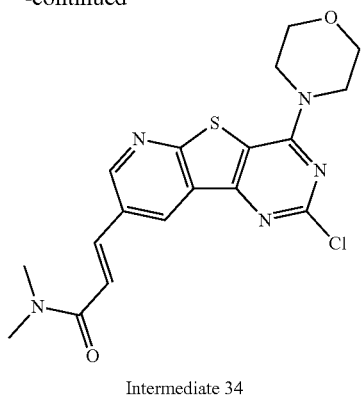

Intermediate 34

To a suspension of Intermediate 32 (8 g, 0.018 mol, 1 eq) in methanol (150 mL) and dichloromethane (150 mL) was added morpholine (5.2 mL, 0.056 mol, 2.4 eq). The reaction mixture was stirred at rt for 4 h (monitored by TLC). After completion of the reaction, dichloromethane was removed by evaporation in vacuo and the residue in methanol was diluted with ice-water and stirred for 30 min. The solid obtained was filtered, washed with water (100 mL) and dried to yield Intermediate 33 (7 g, 76%).

$^1$H NMR (400 MHz, CDCl$_3$) $\delta_H$: 8.82 (br s, 2H), 4.04 (m, 4H), 3.89 (m, 4H).

MS (ES$^+$) 387 (100%, [M+H]$^+$).

Intermediate 34

(2E)-3-[4-Chloro-6-(morpholin-4-yl)-8-thia-3,5,10-triazatricyclo[7.4.0.0²,⁷]trideca-1(9),2(7),3,5,10,12-hexaen-12-yl]-N,N-dimethylprop-2-enamide

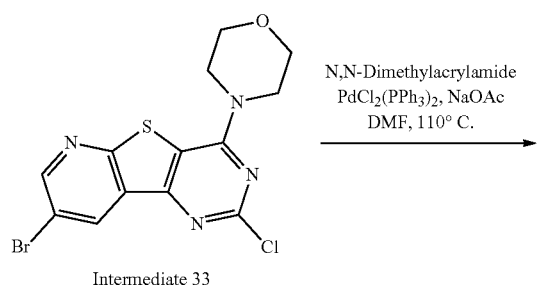

Intermediate 33 (5 g, 0.0129 mol, 1 eq) was dissolved in DMF (50 mL) and N, N-dimethylacrylamide (1.3 mL, 0.0129 mol, 1 eq) and sodium acetate (3.1 g, 0.038 mol, 3 eq) was added and the reaction mixture was degassed for 30 min using argon. Then Pd(PPh$_3$)$_2$Cl$_2$ (0.275 g, 0.0004 mol, 0.03 eq) was added and the reaction mixture was again degassed with argon for 15 min. The reaction mixture was heated at 110° C. for 5 h, (the reaction was monitored by TLC and LCMS). After completion of reaction, the reaction mixture was cooled to rt and then diluted with CH$_2$Cl$_2$ (500 mL) and washed with ice-cold water (2×125 mL). The combined organic layers was dried over Na$_2$SO$_4$ and then the solvent removed by evaporation in vacuo to yield a solid residue. The residue was triturated with ethyl acetate (50 mL) and filtered to yield 4.5 g (86%) of Intermediate 34.

1H NMR (400 MHz, CDCl$_3$) $\delta_H$: 8.86 (br s, 2H), 7.82 (d, J=15.2 Hz, 1H), 7.17 (d, J=15.2 Hz, 1H), 4.06 (m, 4H), 3.90 (m, 4H), 3.24 (s, 3H), 3.11 (s, 3H).

MS (ES$^+$) 404 (100%, [M+H]$^+$).

Intermediate 35

4-Chloro-6-(morpholin-4-yl)-8-thia-3,5,10-triazatricyclo[7.4.0.0²,⁷]trideca-1(9),2(7),3,5,10,12-hexaene-12-carbaldehyde

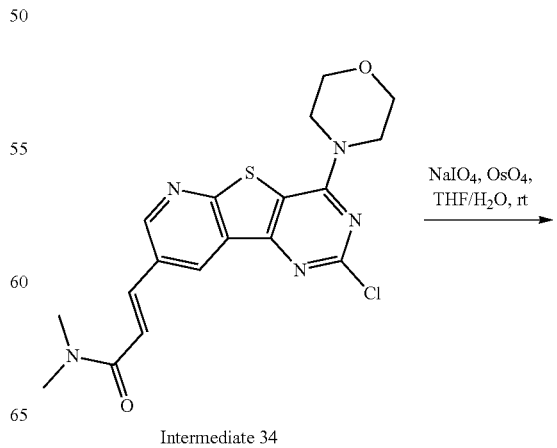

-continued

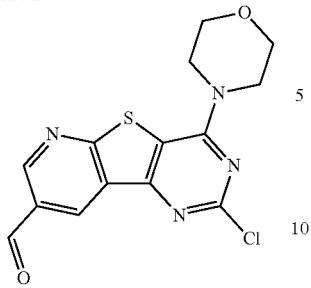

Intermediate 35

Intermediate 34 (5 g, 0.0123 mol, 1 eq) was taken up in THF: water (75 mL: 75 mL) and heated to 70° C. to dissolve the compound. To the reaction mixture were added sodium metaperiodate (8 g, 0.37 mol, 3 eq) followed by OsO$_4$ (2% solution in t-BuOH, 26 mL, 0.002 mol, 0.17 eq) and the reaction mixture was stirred at rt for 18 h. The reaction mixture was quenched with sat. sodium thiosulfate solution. THF and t-BuOH were removed by evaporation in vacuo to give a suspension of the product in water. The mixture was cooled to rt and the solid was isolated by filtration, the residue was stirred in deionised water and filtered. The solid was dried under high vacuum to yield 3.3 g (67%) of Intermediate 35.

$^1$H NMR (400 MHz, DMSO-d$_6$) δ$_H$: 10.26 (s, 1H), 9.25 (br s, 1H), 9.15 (br s, 1H), 3.96 (m, 4H), 3.82 (m, 4H).

$^1$H NMR (400 MHz, CDCl$_3$) δ$_H$: 10.26 (s, 1H), 9.25 (br s, 1H), 9.15 (br s, 1H), 4.12 (m, 4H), 3.89 (m, 4H).

MS (ES$^+$) 335 (100%, [M+H]$^+$).

Intermediate 36

4-(1H-Indol-4-yl)-6-(morpholin-4-yl)-8-thia-3,5,10-triazatricyclo[7.4.0.0$^{2,7}$]trideca-1(9),2(7),3,5,10,12-hexaene-12-carbaldehyde

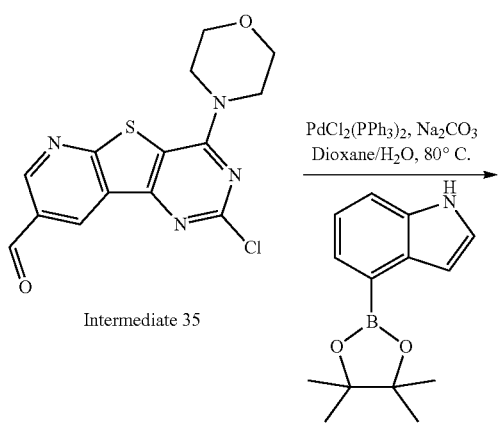

Intermediate 35

-continued

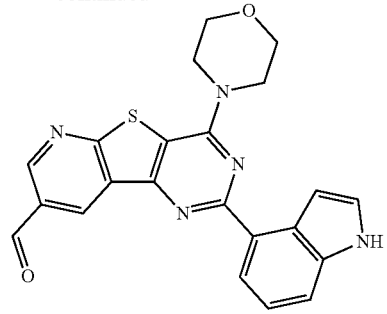

Intermediate 36

Intermediate 35 (2 g, 5.9 mmol, 1 eq.) was taken in dioxane (60 mL), toluene (20 mL) and aqueous 2M Na$_2$CO$_3$ (30 mL) and indole-4-boronic acid pinacolester (2 g, 8.2 mmol, 1.4 eq.), PdCl$_2$(PPh$_3$)$_2$ (1 g, 1.42 mmol, 0.24 eq.) were added to it. The reaction mixture was heated to 80° C. for 1 h and completion of the reaction was confirmed by TLC. The reaction mixture was cooled to 70° C. water (50 mL) and ethyl acetate (700 mL) was added. The organics were separated the aqueous re-extracted with ethyl acetate (2×700 mL) at 60° C. The combined organics were evaporated and residue was triturated with dichloromethane (50 mL) to give Intermediate 36. Some product was left suspended in the aqueous layer. The aqueous layer was filtered and the residue was washed with dichloromethane (50 mL). The solids (from ethyl acetate and water) were mixed together and triturated with dichloromethane (20 mL) to yield 1.8 g (74%) of Intermediate 36.

$^1$H NMR (400 MHz, DMSO-d$_6$) δ: 10.24 (s, 1H), 9.27 (br s, 1H), 9.12 (br s, 1H), 8.27 (d, J=7.6 Hz, 1H), 7.6-7.55 (m, 3H), 7.25 (t, J=7.6 Hz, 1H), 7.25 (t, J=7.6 Hz, 1H), 3.95-4.10 (m, 4H), 3.78-3.90 (m, 4H).

MS (ES$^+$) 416 (100%, [M+H]$^+$).

Intermediate 37

4-(4,4,5,5-tetramethyl-1,3,2-dioxaborolan-2-yl)-2,3-dihydro-1H-indole

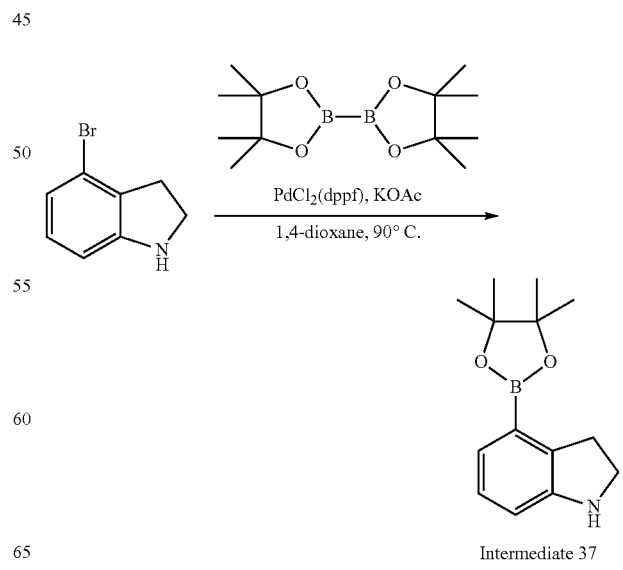

Intermediate 37

A solution of 4-bromoindoline (694 mg, 3.50 mmol, 1.0 eq) in 1,4-dioxane (10 mL) was degassed with argon for 30 min before the addition of bis(pinacolato)diboron (1.07 g, 4.20 mmol, 1.2 eq). Whilst degassing, potassium acetate (1.03 g, 10.5 mmol, 3.0 eq) and PdCl$_2$(dppf)-CH$_2$Cl$_2$ (143 mg, 0.175 mmol, 5 mol %) were added. The vessel was then sealed and stirred at 100° C. for 2 h. Upon cooling, the reaction mixture was diluted with H$_2$O (5 mL), poured into 50% brine (15 mL) and extracted with EtOAc (3×20 mL). The combined organic extracts were dried over MgSO$_4$, filtered and concentrated in vacuo. Purification by silica gel column chromatography with hexane/EtOAc (1:0-9:1) yielded Intermediate 37 as a cream solid (539 mg, 63%).

$^1$H NMR (300 MHz, CDCl$_3$) $\delta_H$: 7.17 (d, J=7.5 Hz, 1H), 7.04 (t, J=7.5 Hz, 1H), 6.77 (d, J=7.5 Hz, 1H), 3.48-3.61 (m, 2H), 3.18-3.31 (m, 2H), 1.84 (br. s., 1H), 1.33 (s, 12H).

MS (ES$^+$) 246.2 (100%, [M+H]$^+$).

Intermediate 38

5-methyl-4-(4,4,5,5-tetramethyl-1,3,2-dioxaborolan-2-yl)-1H-indole

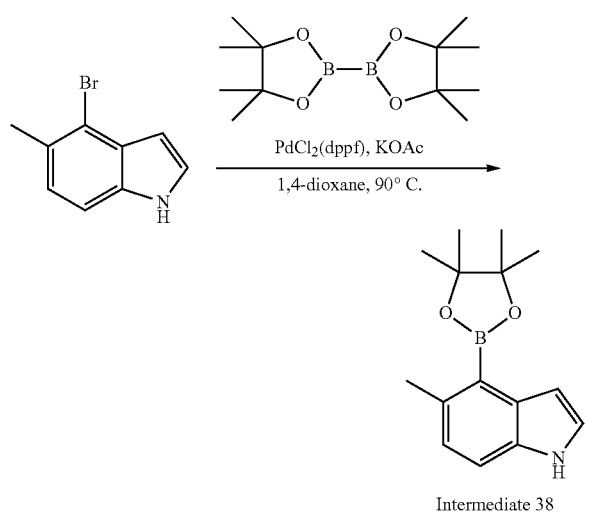

Intermediate 38

A solution of 4-bromo-5-methylindole (805 mg, 3.64 mmol, 1.0 eq) in degassed 1,4-dioxane (10 mL) was degassed with argon for a further 5 min before the addition of bis(pinacolato)diboron (1.20 g, 4.73 mmol, 1.3 eq). Whilst degassing, potassium acetate (1.07 g, 10.9 mmol, 3.0 eq) and PdCl$_2$(dppf)-CH$_2$Cl$_2$ (149 mg, 0.182 mmol, 5 mol %) were added. The vessel was then sealed and stirred at 90° C. for 2.5 h. Upon cooling, the reaction mixture was diluted with H$_2$O (10 mL), poured into 50% brine (50 mL) and extracted with EtOAc (3×50 mL). The combined organic extracts were dried over MgSO$_4$, filtered and concentrated in vacuo. Purification twice by silica gel column chromatography with hexane/EtOAc (1:0-14:1) then hexane/CH$_2$Cl$_2$ (1:0-1:1) yielded Intermediate 38 as a white solid (400 mg, 43%).

$^1$H NMR (300 MHz, CDCl$_3$) $\delta_H$: 8.05 (br s, 1H), 7.34 (d, J=8.3 Hz, 1H), 7.20 (t, J=2.7 Hz, 1H), 7.03 (d, J=8.3 Hz, 1H), 6.98 (td, J=2.0, 1.0 Hz, 1H), 2.64 (s, 3H), 1.42 (s, 12H).

MS (ES$^+$) 258.2 (100%, [M+H]$^+$), 280.1 (40%, [M+Na]$^+$).

Intermediate 39

7-fluoro-4-(4,4,5,5-tetramethyl-1,3,2-dioxaborolan-2-yl)-1H-indole

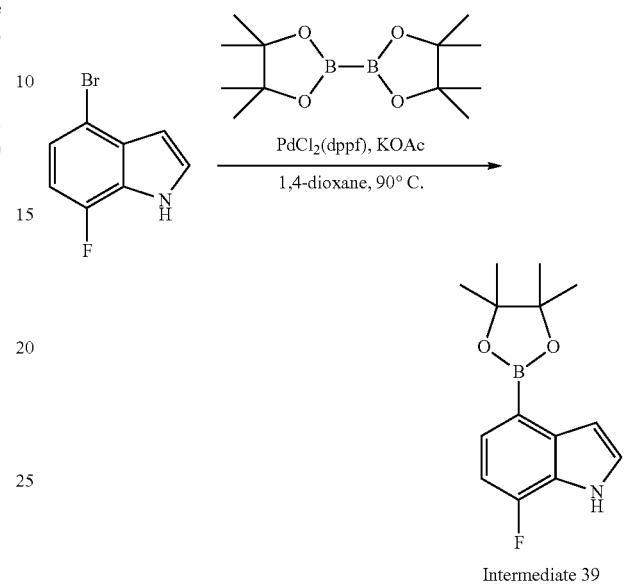

Intermediate 39

A solution of 4-bromo-7-fluoroindole (863 mg, 4.03 mmol, 1.0 eq) in 1,4-dioxane (10 mL) was degassed with argon for 5 min before the addition of bis(pinacolato)diboron (1.33 g, 5.24 mmol, 1.3 eq). Whilst degassing, potassium acetate (1.19 g, 12.1 mmol, 3.0 eq) and PdCl$_2$(dppf) (88.5 mg, 0.121 mmol, 3 mol %) were added. The vessel was then sealed and stirred at 90° C. for 2 h. Upon cooling, the reaction mixture was poured into 50% brine (50 mL) and extracted with EtOAc (3×30 mL). The combined organic extracts were dried over MgSO$_4$, filtered and concentrated in vacuo. Purification by silica gel column chromatography with hexane/CH$_2$Cl$_2$ (1:0-3:2) yielded Intermediate 39 as a cream solid (691 mg, 66%).

$^1$H NMR (300 MHz, CDCl$_3$) $\delta_H$: 8.35 (br s, 1H), 7.58 (dd, J=7.8, 5.4 Hz, 1H), 7.28-7.31 (m, 1H), 7.08 (td, J=3.4, 2.3 Hz, 1H), 6.92 (dd, J=11.2, 7.8 Hz, 1H), 1.39 (s, 12H).

$^{19}$F NMR (282 MHz, CDCl$_3$) $\delta_F$: -131.02--130.92 (m, 1F).

MS (ES$^+$) 262.1 (100%, [M+H]$^+$), 284.0 (25%, [M+Na]$^+$).

Intermediate 40

4-(4,4,5,5-tetramethyl-1,3,2-dioxaborolan-2-yl)-1H-indole-6-carbonitrile

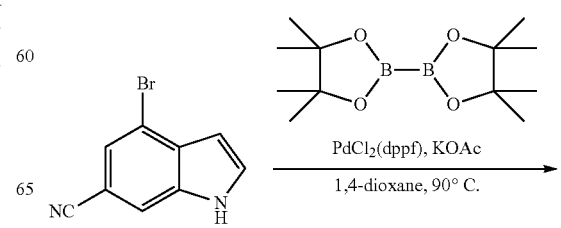

Intermediate 40

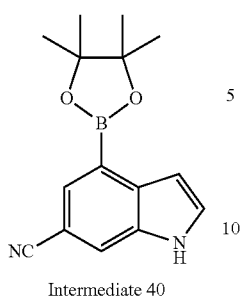

A solution of 4-bromo-6-cyanoindole (612 mg, 2.77 mmol, 1.0 eq) in 1,4-dioxane (15 mL) was degassed with argon for 10 min before the addition of bis(pinacolato)diboron (914 mg, 3.60 mmol, 1.3 eq). Whilst degassing, potassium acetate (816 mg, 8.31 mmol, 3.0 eq) and PdCl$_2$(dppf) (60.8 mg, 0.0831 mmol, 3 mol %) were added and the reaction mixture was stirred at 90° C. for 2 h. Upon cooling, the reaction mixture was poured into 50% brine (50 mL) and extracted with EtOAc (3×50 mL). The combined organic extracts were dried over MgSO$_4$, filtered and concentrated in vacuo. Purification twice by silica gel column chromatography using hexane/CH$_2$Cl$_2$ (1:0-1:4) then hexane/EtOAc (1:0-19:1) yielded Intermediate 40 as a white solid (566 mg, 76%).

$^1$H NMR (300 MHz, CDCl$_3$) δ$_H$: 8.51 (br. s., 1H), 7.88 (d, J=1.5 Hz, 1H), 7.78-7.84 (m, 1H), 7.42-7.51 (m, 1H), 7.12 (ddd, J=3.2, 2.1, 0.9 Hz, 1H), 1.41 (s, 12H).

MS (ES$^+$) 269.1 (45%, [M+H]$^+$), 291.0 (100%, [M+Na]$^+$).

Intermediate 41

6-(Morpholin-4-yl)-4-[2-(trifluoromethyl)-1H-indol-4-yl]-8-oxa-3,5,10-triazatricyclo[7.4.0.0$^{2,7}$]trideca-1(13),2(7),3,5,9,11-hexaene-12-carbaldehyde

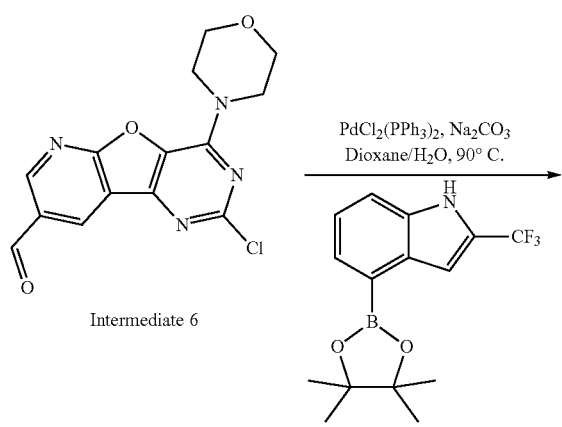

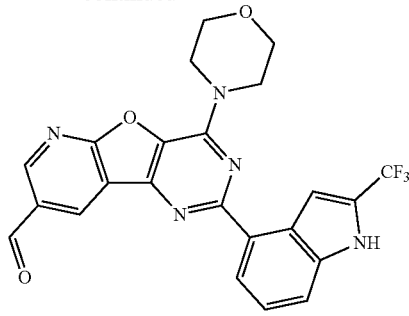

To Intermediate 6 (340 mg, 1.07 mmol, 1 eq) was added 4-(tetramethyl-1,3,2-dioxaborolan-2-yl)-2-(trifluoromethyl)-1H-indole (1.0 g, 3.20 mmol, 3 eq), PdCl$_2$(PPh$_3$)$_2$ (150 mg, 0.21 mmol, 0.2 eq) and sodium carbonate (227 mg, 2.1 mmol, 2 eq) in dioxane (30 mL)/water (10 mL). Reaction mixture was heated at 90° C. overnight. It was then cooled to 60-70° C. Water (20 mL) and EtOAc (50 mL) were added. The phases were separated and the aqueous phase extracted with EtOAc (3×50 mL) at 60-65° C. The combined organics were dried over MgSO$_4$, filtered and the solvent was removed by evaporation in vacuo. The resulting solid was triturated in CH$_2$Cl$_2$ (5 mL), filtered and washed with CH$_2$Cl$_2$ (2 ×2 mL). Following drying, Intermediate 41 was obtained as a grey solid (252 mg, 50% yield).

$^1$H NMR (300 MHz, DMSO-d$_6$) δ$_H$: 12.46 (s, 1H), 10.26 (s, 1H), 9.15 (d, J=2.1 Hz, 1H), 9.04 (d, J=2.1 Hz, 1H), 8.26 (dd, J=7.3, 0.8 Hz, 1H), 7.99 (s, 1H), 7.63 (d, J=8.3 Hz, 1H), 7.39-7.48 (m, 1H), 4.10 (m, 4H), 3.86 (m, 4H).

MS (ES$^+$) 467.8 (100%, [M+H]$^+$).

Intermediate 42 tert-Butyl 5-amino-4-bromo-1H-indole-1-carboxylate

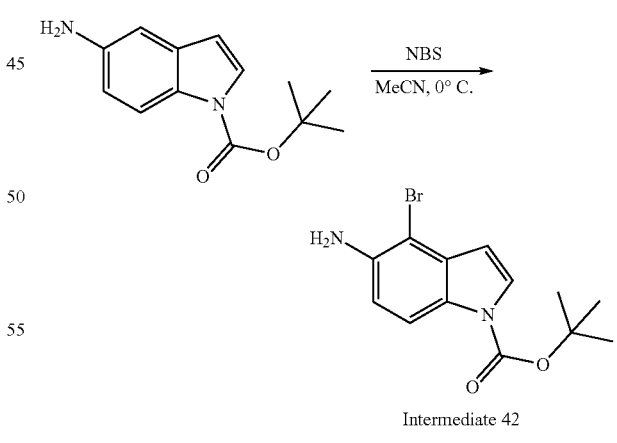

To a solution of 1-Boc-5-aminoindole (2.05 g, 8.47 mmol, 1.0 eq) in MeCN (85 mL) at 0° C. was added N-bromosuccinimide (1.51 g, 8347 mmol, 1.0 eq) and the reaction was stirred at 0° C. for 2.5 h. Upon warming to rt, the mixture was concentrated in vacuo and purified by silica gel chromatography using hexane/EtOAc (1:0-19:1) to yield Intermediate 42 as a yellow solid (2.53 g, 96%).

$^1$H NMR (300 MHz, CD$_3$OD) δ$_H$: 7.86 (d, J=8.7 Hz, 1H), 7.57 (d, J=3.8 Hz, 1H), 6.85 (d, J=8.7 Hz, 1H), 6.50 (dd, J=3.8, 0.6 Hz, 1H), 1.66 (s, 9H).

MS (ES$^+$) 311.0 (100%, [M+H]$^+$).

Intermediate 43 tert-Butyl 4-bromo-5-chloro-1H-indole-1-carboxylate

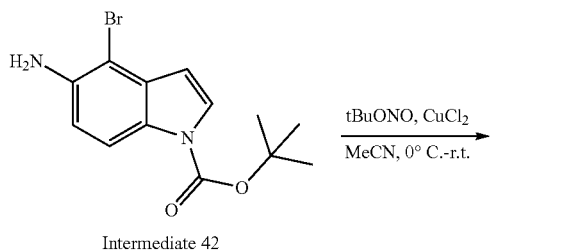

Intermediate 42

To a suspension of copper(II) chloride (274 mg, 2.04 mmol, 1.2 eq) in MeCN (17 mL) at 0° C. was added tert-butyl nitrite (337 µL, 2.55 mmol, 1.5 eq) followed by a solution of Intermediate 42 (529 mg, 1.70 mmol, 1.0 eq) in MeCN (4 mL). After stirring at 0° C. for 15 min, the reaction mixture was allowed to warm to rt and stirred for 2.5 h. The reaction was quenched by the addition of 1 M aqueous HCl (10 mL) and poured into 50% brine (20 mL). The resulting mixture was extracted with EtOAc (3×25 mL), dried over MgSO$_4$, filtered and concentrated in vacuo. Purification by silica gel chromatography using hexane/CH$_2$Cl$_2$ (1:0-13:1) yielded Intermediate 43 as a white solid (364 mg, 65%).

$^1$H NMR (300 MHz, DMSO-d$_6$) δ$_H$: 8.05 (d, J=8.7 Hz, 1H), 7.85 (d, J=3.8 Hz, 1H), 7.53 (d, J=8.7 Hz, 1H), 6.68 (d, J=3.8 Hz, 1H), 1.63 (s, 9H).

$^{13}$C NMR (75 MHz, DMSO-d$_6$) δ$_H$: 148.5, 133.0, 132.2, 128.7, 127.3, 125.5, 115.3, 113.4, 107.1, 84.9, 27.6.

Intermediate 44 tert-Butyl 5-chloro-4-(4,4,5,5-tetramethyl-1,3,2-dioxaborolan-2-yl)-1H-indole-1-carboxylate

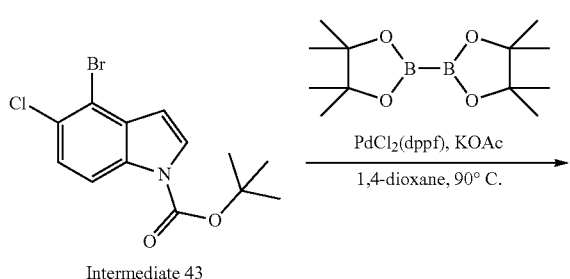

Intermediate 43

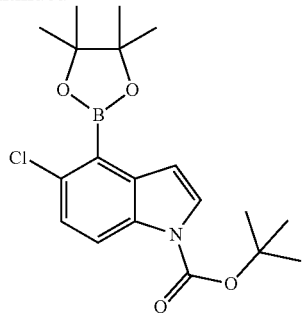

Intermediate 44

A solution of Intermediate 43 (923 mg, 2.79 mmol, 1.0 eq) in 1,4-dioxane (17 mL) was degassed with argon for 15 min before the addition of bis(pinacolato)diboron (2.13 g, 8.38 mmol, 3.0 eq). Whilst degassing, potassium acetate (822 mg, 8.38 mmol, 3.0 eq) and PdCl$_2$(dppf) (61.3 mg, 0.0838 mmol, 3 mol %) were added and the reaction mixture was stirred at 90° C. for 16 h. Upon cooling, the reaction mixture was poured into 50% brine (50 mL) and extracted with EtOAc (3×50 mL). The combined organic extracts were dried over MgSO$_4$, filtered and concentrated in vacuo. Purification three times by silica gel column chromatography using hexane/EtOAc (1:0-19:1) then hexane/EtOAc (1:0-49:1) then hexane/EtOAc (1:0-99:1) yielded Intermediate 44 as a colourless oil (279 mg, 26%).

$^1$H NMR (300 MHz, CDCl$_3$) δ$_H$: 8.11 (d, J=8.7 Hz, 1H), 7.62 (d, J=3.6 Hz, 1H), 7.28-7.32 (m, 1H), 6.85 (d, J=3.8 Hz, 1H), 1.68 (s, 9H), 1.45 (s, 12H).

MS (ES$^+$) 400.1 (100%, [M+Na]$^+$).

Intermediate 45 tert-Butyl 5-chloro-4-[6-(morpholin-4-yl)-12-[(1-oxo-1λ$^4$-thiomorpholin-4-yl)methyl]-8-oxa-3,5,10-triazatricyclo[7.4.0.0$^{2,7}$]trideca-1(13),2(7),3,5,9,11-hexaen-4-yl]-1H-indole-1-carboxylate

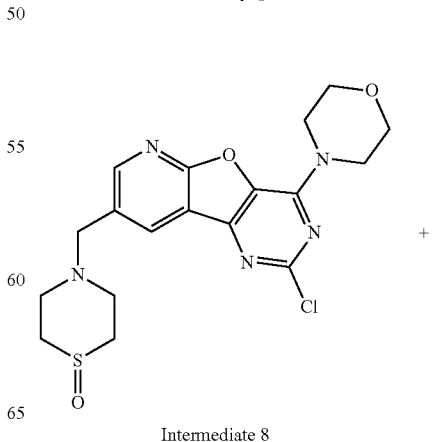

Intermediate 8

-continued

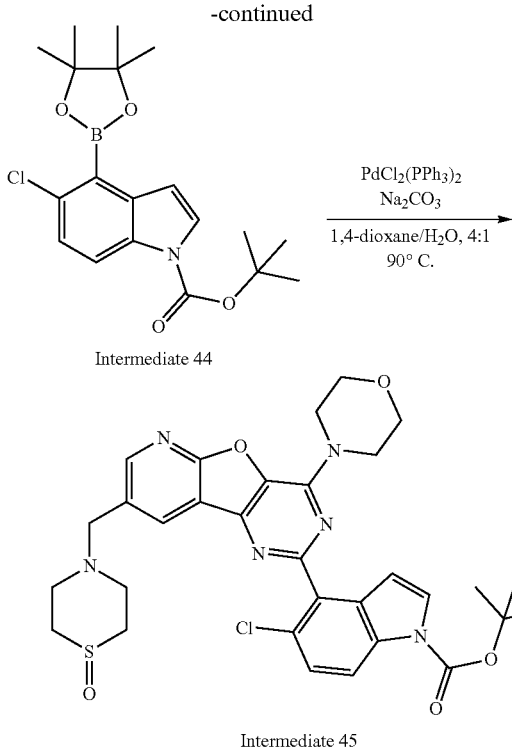

Intermediate 44

Intermediate 45

To a microwave vial containing Intermediate 8 (154 mg, 0.365 mmol, 1.0 eq), Intermediate 44 (276 mg, 0.731 mmol, 2.0 eq), sodium carbonate (85.1 mg, 0.803 mmol, 2.2 eq) and PdCl$_2$(PPh$_3$)$_2$ (51.3 mg, 0.0731 mmol, 20 mol %) was added 1,4-dioxane (3 mL) and H$_2$O (1 mL). The suspension was stirred at 90° C. for 4 h then cooled to room temperature, poured into H$_2$O (15 mL) and extracted with CH$_2$Cl$_2$ (3×15 mL). The combined organic extracts were dried over MgSO$_4$, filtered, concentrated in vacuo, re-dissolved in CH$_2$Cl$_2$/MeOH (4:1, 20 mL) and swirled with MP-TMT resin (400 mg, 0.440 mmol, 6 eq wrt Pd) at rt for 4 h. The solution was filtered and the resin washed with CH$_2$Cl$_2$/MeOH (4:1, 150 mL). The filtrate was concentrated in vacuo and purified by silica gel column chromatography using hexane/EtOAc/MeOH (1:0:0-0:9:1) to yield Intermediate 45 as an off-white solid (188 mg, 81%).

$^1$H NMR (300 MHz, DMSO-d$_6$) δ$_H$: 8.64 (s, 1H), 8.55 (s, 1H), 8.13 (d, J=8.9 Hz, 1H), 7.73 (d, J=3.8 Hz, 1H), 7.49 (d, J=8.9 Hz, 1H), 6.58 (d, J=3.8 Hz, 1H), 3.99-4.19 (m, 4H), 3.73-3.89 (m, 6H), 2.82-3.00 (m, 4H), 2.65-2.82 (m, 4H), 1.65 (s, 9H).

MS (ES$^+$) 319.2 60%, [M+2H]$^{2+}$), 637.2 (100%, [M+H]$^+$).

Intermediate 46

5-Amino-4-bromoindole

Intermediate 42

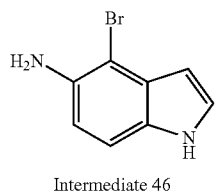

Intermediate 46

To a solution of Intermediate 42 (2.60 g, 8.36 mmol, 1.0 eq) in MeOH (50 mL) was added H$_2$O (17 mL) and potassium carbonate (3.47 g, 25.1 mmol, 3.0 eq) and the reaction was stirred at 55° C. for 2 h, then at 45° C. for 16 h. Upon cooling to rt, the suspension was filtered and the solids washed with H$_2$O (200 mL) and dried under vacuum, yielding Intermediate 46 as light brown crystals (1.23 g). The filtrate was concentrated in vacuo to remove MeOH then extracted with CH$_2$Cl$_2$ (4×50 mL) and the combined organic extracts were dried over MgSO$_4$, filtered and concentrated in vacuo. Purification by silica gel chromatography using hexane/EtOAc (1:0-2:1) yielded the remaining Intermediate 46 as an orange-brown solid (454 mg, total 95%).

$^1$H NMR (300 MHz, DMSO-d$_6$) δ$_H$: 10.97 (br s, 1H), 7.23 (t, J=2.7 Hz, 1H), 7.14 (d, J=8.5 Hz, 1H), 6.68 (d, J=8.5 Hz, 1H), 6.15 (t, J=2.1 Hz, 1H), 4.69 (br. s, 2H).

MS (ES$^+$) 211.0 (100%, [M+H]$^+$).

Intermediate 47

4-Bromo-1H-indole-5-carbonitrile

Intermediate 46

Intermediate 47

To a solution of Intermediate 46 (307 mg, 1.45 mmol, 1.0 eq) in MeCN (15 mL) at 0° C. was added 50% w/w fluoroboric acid in H$_2$O (288 μL, 2.18 mmol, 1.5 eq) followed by tert-butyl nitrite (287 μL, 2.18 mmol, 1.5 eq) and the reaction mixture was allowed to warm to rt and stirred for 45 min. After re-cooling to 0° C., a suspension of copper(I) cyanide (390 mg, 4.35 mmol, 3.0 eq) in H$_2$O (5 mL) was added and the reaction mixture was warmed to rt then stirred at 60° C. for 4 h. Upon cooling to rt, the mixture was poured into H$_2$O (30 mL) and extracted with EtOAc (4×25 mL). The combined organic extracts were dried over MgSO$_4$, filtered, concentrated in vacuo and purified by silica gel chromatography using hexane/EtOAc (1:0-5:1) to yield Intermediate 47 as a pale orange solid (147 mg, 46%).

$^1$H NMR (300 MHz, DMSO-d$_6$) δ$_H$: 12.00 (br s, 1H), 7.65-7.71 (m, 1H), 7.59 (dd, J=8.5, 0.7 Hz, 1H), 7.51 (d, J=8.5 Hz, 1H), 6.57 (dt, J=2.1, 1.2 Hz, 1H).

MS (ES+) 221.0 (50%, [M+H]+), 243.0 (100%, [M+Na]+).

Intermediate 48

4-(4,4,5,5-tetramethyl-1,3,2-dioxaborolan-2-yl)-1H-indole-5-carbonitrile

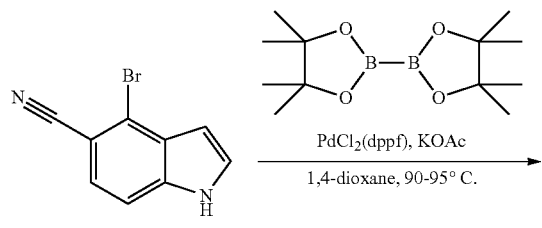

Intermediate 47

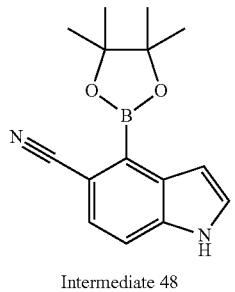

Intermediate 48

A suspension of Intermediate 47 (598 mg, 2.71 mmol, 1.0 eq) in 1,4-dioxane (16 mL) was degassed with argon for 10 min before the addition of bis(pinacolato)diboron (1.03 g, 4.06 mmol, 1.5 eq). Whilst degassing, potassium acetate (797 mg, 8.12 mmol, 3.0 eq) and PdCl₂(dppf) (59.4 mg, 0.0812 mmol, 3 mol %) were added and the reaction mixture was stirred at 90° C. for 16 h. Upon cooling, the reaction mixture was degassed with argon whilst additional portions of bis(pinacolato)diboron (688 mg, 2.71 mmol, 1.0 eq), potassium acetate (399 mg, 2.71 mmol, 1.0 eq) and PdCl₂(dppf) (99.1 mg, 0.136 mmol, 5 mol %) were added. The reaction mixture was stirred at 95° C. for 6.5 h then cooled to rt, poured into 50% brine (20 mL) and extracted with EtOAc (3×25 mL). The combined organic extracts were dried over MgSO₄, filtered and concentrated in vacuo. Purification twice by silica gel column chromatography using CH₂Cl₂/MeOH (1:0-49:1) then hexane/EtOAc (1:0-2:1) yielded Intermediate 48 as an off-white solid (405 mg, 52% containing 7 mol % bis(pinacolato)diboron as an impurity).

$^1$H NMR (300 MHz, DMSO-d₆) $\delta_H$: 11.64 (br s, 1H), 7.64 (dd, J=8.5, 0.8 Hz, 1H), 7.56-7.60 (m, 1H), 7.45 (d, J=8.3 Hz, 1H), 6.75-6.85 (m, 1H), 1.33-1.40 (m, 12H).

MS (ES+) 269.2 (65%, [M+H]+), 291.1 (100%, [M+Na]+).

Intermediate 49 tert-Butyl 5-hydroxy-1H-indole-1-carboxylate

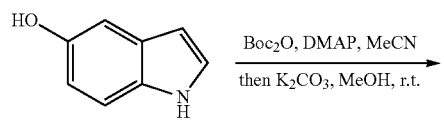

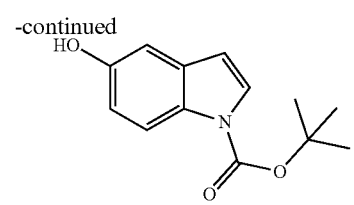

Intermediate 49

To a solution of 5-hydroxyindole (2.02 g, 15.2 mmol, 1.0 eq) in MeCN (20 mL) was added di-tert-butyl dicarbonate (9.93 g, 45.5 mmol, 3.0 eq) and DMAP (186 mg, 1.52 mmol, 10 mol %). The reaction mixture was stirred at rt for 1 h then concentrated in vacuo, re-dissolved in CH₂Cl₂ (20 mL) and washed with H₂O (20 mL). The aqueous phase was extracted with CH₂Cl₂ (20 mL) and the combined organic extracts were dried over MgSO₄, filtered and concentrated in vacuo. The residue was then dissolved in MeOH (100 mL) and cooled to 0° C. before the addition of potassium carbonate (10.5 g, 76 mmol, 5.0 eq) portionwise. The reaction was allowed to warm to rt and stirred for 1.5 h, then re-cooled to 0° C. and quenched by the dropwise addition of acetic acid to neutralise the mixture. H₂O (100 mL) was added and the resulting mixture was extracted with EtOAc (3 ×100 mL). The combined organic extracts were dried over MgSO₄, filtered and concentrated in vacuo. Purification twice by silica gel chromatography using hexane/EtOAc (1:0-6:1) then hexane/CH₂Cl₂ (1:0-1:4) yielded Intermediate 49 as a white solid (3.05 g, 86%).

$^1$H NMR (300 MHz, DMSO-d₆) $\delta_H$: 9.18 (s, 1H), 7.82 (d, J=8.9 Hz, 1H), 7.55 (d, J=3.8 Hz, 1H), 6.92 (d, J=2.4 Hz, 1H), 6.77 (dd, J=8.9, 2.4 Hz, 1H), 6.54 (d, J=3.8 Hz, 1H), 1.56-1.64 (m, 9H).

MS (ES+) 256.1 (40%, [M+Na]+).

Intermediate 50 tert-Butyl 4-bromo-5-hydroxy-1H-indole-1-carboxylate

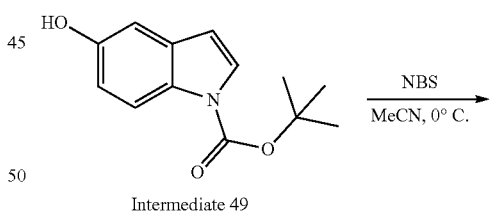

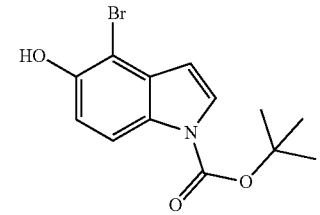

Intermediate 50

To a solution of Intermediate 49 (3.00 g, 12.9 mmol, 1.0 eq) in anhydrous MeCN (13 mL) was added a solution of N-bromosuccinimide (2.53 g, 14.2 mmol, 1.1 eq) in anhydrous MeCN (130 mL) dropwise via cannula. After 1.5 h, addition was complete and the reaction mixture was stirred for a further 1 h. The reaction mixture was concentrated in vacuo and purified twice by silica gel chromatography using hexane/CH$_2$Cl$_2$ (1:0-1.5:1) to yield Intermediate 50 as a white solid (605 mg, 15%).

$^1$H NMR (300 MHz, DMSO-d$_6$) $\delta_H$: 9.95 (s, 1H), 7.78-7.91 (m, 1H), 7.61-7.73 (m, 1H), 6.97 (d, J=8.9 Hz, 1H), 6.50-6.59 (m, 1H), 1.54-1.70 (m, 9H).

MS (ES$^-$) 311.9 (45%, [M–H]$^-$).

Intermediate 51 tert-Butyl 4-bromo-5-(propan-2-yloxy)-1H-indole-1-carboxylate

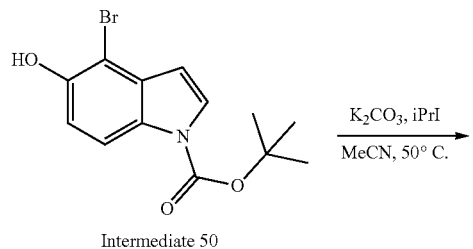

Intermediate 50

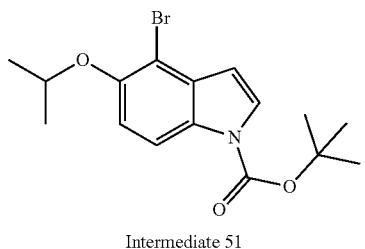

Intermediate 51

To a solution of Intermediate 50 (714 mg, 2.29 mmol, 1.0 eq) in anhydrous MeCN (40 mL) was added potassium carbonate (632 mg, 4.57 mmol, 2.0 eq) followed by 2-iodopropane (457 µL, 4.57 mmol, 2.0 eq) and the reaction mixture was stirred at 50° C. for 18 h. After cooling to rt, additional potassium carbonate (158 mg, 1.15 mmol, 0.5 eq) and 2-iodopropane (114 µL, 1.15 mmol, 0.5 eq) were added and the reaction mixture was stirred at 50° C. for a further 2 h. The reaction mixture was then cooled to rt and additional portions of potassium carbonate (316 mg, 2.29 mmol, 1.0 eq) and 2-iodopropane (229 µL, 2.29 mmol, 1.0 eq) were added. After stirring at 50° C. for 2 h, the reaction mixture was cooled to rt, poured into H$_2$O (100 mL), extracted with CH$_2$Cl$_2$ (3×50 mL) and washed with brine (100 mL). The aqueous phase was re-extracted with EtOAc (50 mL) and the combined organic extracts were dried over MgSO$_4$, filtered and concentrated in vacuo. Purification by silica gel chromatography using hexane/CH$_2$Cl$_2$ (1:0-7:3) yielded Intermediate 51 as a colourless oil (736 mg, 91%).

$^1$H NMR (300 MHz, DMSO-d$_6$) $\delta_H$: 7.97 (d, J=9.0 Hz, 1H), 7.74 (d, J=3.8 Hz, 1H), 7.17 (d, J=9.0 Hz, 1H), 6.59 (d, J=3.8 Hz, 1H), 4.61 (spt, J=6.1 Hz, 1H), 1.62 (s, 9H), 1.29 (d, J=6.0 Hz, 6H).

MS (ES$^+$) 376.0 (30%, [M+Na]$^+$).

Intermediate 52 tert-Butyl 5-(propan-2-yloxy)-4-(4,4,5,5-tetramethyl-1,3,2-dioxaborolan-2-yl)-1H-indole-1-carboxylate

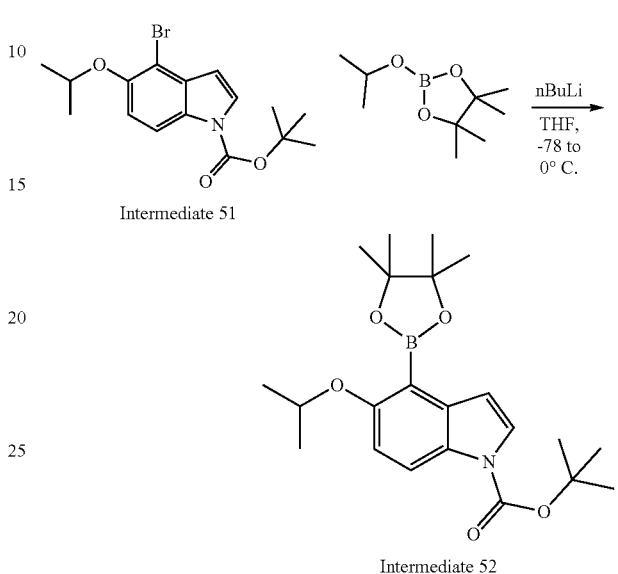

To a solution of Intermediate 51 (528 mg, 1.491 mmol, 1.0 eq) in THF (10 mL) at –78° C. was added 1.6 M nBuLi solution in hexanes (1.03 mL, 1.64 mmol, 1.1 eq) dropwise. The reaction mixture was stirred at –78° C. for 15 min then a pre-cooled solution of isopropyl pinacol borate (408 µL, 1.94 mmol, 1.3 eq) in THF (5 mL) was added dropwise at –78° C. After stirring for 1.5 h, the reaction mixture was warmed to 0° C., quenched by the dropwise addition of H$_2$O (10 mL) then warmed to rt. The mixture was poured into 50% brine (30 mL), extracted with EtOAc (3×20 mL) and the combined organic extracts were dried over MgSO$_4$, filtered and concentrated in vacuo. Purification by silica gel chromatography using hexane/EtOAc (1:0-19:1) yielded Intermediate 52 as a colourless oil (380 mg, 63%).

$^1$H NMR (300 MHz, DMSO-d$_6$) $\delta_H$: 8.02 (d, J=8.9 Hz, 1H), 7.64 (d, J=3.8 Hz, 1H), 7.00 (d, J=9.0 Hz, 1H), 6.72 (d, J=3.6 Hz, 1H), 4.43 (spt, J=6.1 Hz, 1H), 1.62 (s, 9H), 1.33 (s, 12H), 1.23 (d, J=6.0 Hz, 6H).

MS (ES$^+$) 424.2 (100%, [M+Na]$^+$).

Intermediate 53 tert-Butyl 4-bromo-5-(trifluoromethoxy)-1H-indole-1-carboxylate

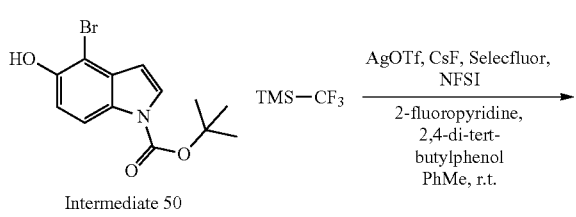

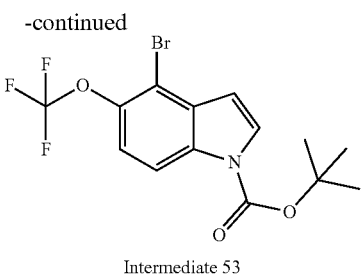

Intermediate 53

A round-bottomed flask containing cesium fluoride (876 mg, 5.77 mmol, 6.0 eq) was heated to 170° C. under vacuum, with gentle stirring, for 2 h. The vessel was backfilled with argon and cooled to rt before the addition of silver trifluoromethanesulfonate (1.24 g, 4.81 mmol, 5.0 eq), Selectfluor® (847 mg, 1.92 mmol, 2.0 eq), N-fluorobenzenesulfonimide (605 mg, 1.92 mmol, 2.0 eq) and 2,4-di-tert-butylphenol (396 mg, 1.92 mmol, 2.0 eq). To the solids were added a solution of Intermediate 50 (300 mg, 0.961 mmol, 1.0 eq) in anhydrous toluene (14 mL), followed by 2-fluoropyridine (417 μL, 4.81 mmol, 5.0 eq) and trimethyl(trifluoromethyl)silane (720 μL, 4.81 mmol, 5.0 eq). The suspension was stirred at rt for 20 h. The reaction mixture was then diluted with EtOAc (10 mL) and filtered through a pad of Celite®, eluting with EtOAc (100 mL). The solution was concentrated in vacuo and purified by silica gel chromatography using hexane/CH$_2$Cl$_2$ (1:0-7:1), yielding Intermediate 53 as a white solid (118 mg, 32%).

$^1$H NMR (300 MHz, DMSO-d$_6$) δ$_H$: 8.15 (d, J=9.0 Hz, 1H), 7.92 (d, J=3.6 Hz, 1H), 7.49 (dd, J=9.0, 1.1 Hz, 1H), 6.76 (d, J=3.8 Hz, 1H), 1.64 (s, 9H).

$^{19}$F NMR (282 MHz, DMSO-d$_6$) δ$_F$: −56.75 (s, 3F).

MS (ES$^-$) 379.0 (70%, [M−H]$^-$).

Intermediate 54 tert-Butyl 4-(4,4,5,5-tetramethyl-1,3,2-dioxaborolan-2-yl)-5-(trifluoromethoxy)-1H-indole-1-carboxylate

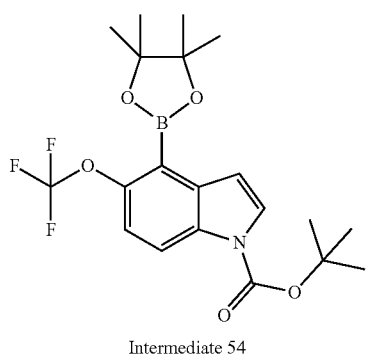

Intermediate 53

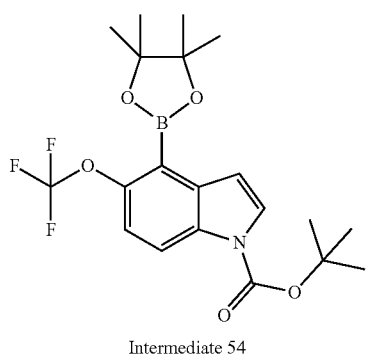

Intermediate 54

To a solution of Intermediate 53 (140 mg, 0.368 mmol, 1.0 eq) in THF (2 mL) at −78° C. was added 1.6 M nBuLi solution in hexanes (253 μL, 0.405 mmol, 1.1 eq) dropwise. The reaction mixture was stirred at −78° C. for 15 min then a pre-cooled solution of isopropyl pinacol borate (101 μL, 0.479 mmol, 1.3 eq) in THF (1 mL) was added dropwise at −78° C. After stirring at −78° C. for 3 h, additional portions of nBuLi (46 μL, 0.0736 mmol, 0.2 eq) and isopropyl pinacol borate (19 μL, 0.0920 mmol, 0.25 eq) were added and the reaction mixture was stirred at −78° C. for a further 1 h. After warming to 0° C., the reaction was quenched by the dropwise addition of H$_2$O (2mL) then warmed to rt. The mixture was poured into 50% brine (20 mL), extracted with EtOAc (3×15 mL) and the combined organic extracts were dried over MgSO$_4$, filtered and concentrated in vacuo. Purification by silica gel chromatography using hexane/CH$_2$Cl$_2$ (1:0-4:1) yielded Intermediate 54 as a colourless oil (60.0 mg, 38%).

$^1$H NMR (300 MHz, CD$_3$OD) δ$_H$: 8.28 (d, J=8.9 Hz, 1H), 7.74 (d, J=3.8 Hz, 1H), 7.21 (d, J=9.0 Hz, 1H), 7.04 (d, J=3.8 Hz, 1H), 1.68 (s, 9H), 1.40 (s, 12H).

$^{19}$F NMR (282 MHz, CD$_3$OD) δ$_F$: −59.05 (s, 3F).

MS (ES$^+$) 450.1 (100%, [M+Na]$^+$).

Intermediate 55

2-Methyl-4-(4,4,5,5-tetramethyl-1,3,2-dioxaborolan-2-yl)-1H-indole

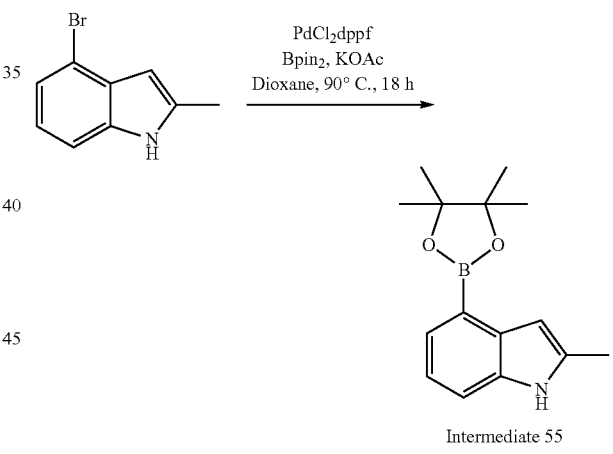

Intermediate 55

To a suspension of 2-methyl-4-bromoindole (970 mg, 4.62 mmol), bispinacolatodiboron (1.29 g, 5.08 mmol, 1.1 eq), KOAc (1.36 g, 13.9 mmol, 3 eq) in dioxane (30 mL) was added PdCl$_2$dppf (101 mg, 0.14 mmol, 0.03 eq) under Ar(g). The reaction mixture was heated up to 90° C. overnight. It was then cooled down to rt, partitioned with water (40 mL) and extracted with EtOAc (3×50 mL). The combined organics were dried over MgSO$_4$, filtered and the solvent was removed in vacuo. Purification by silica gel column chromatography with hexane/EtOAc (1:0-1:1) yielded Intermediate 55 as a pale yellow solid (850 mg, 69%).

$^1$H NMR (300 MHz, DMSO-d$_6$) δ$_H$: 10.88 (br s, 1H), 7.27-7.40 (m, 2H), 6.90-7.02 (m, 1H), 6.43 (d, J=0.9 Hz, 1H), 2.39 (s, 3H), 1.31 (s, 12H).

MS (ES$^+$) 258.2 (100%, [M+H]$^+$).

Intermediate 56

5-Methoxy-4-(4,4,5,5-tetramethyl-1,3,2-dioxaborolan-2-yl)-1H-indole

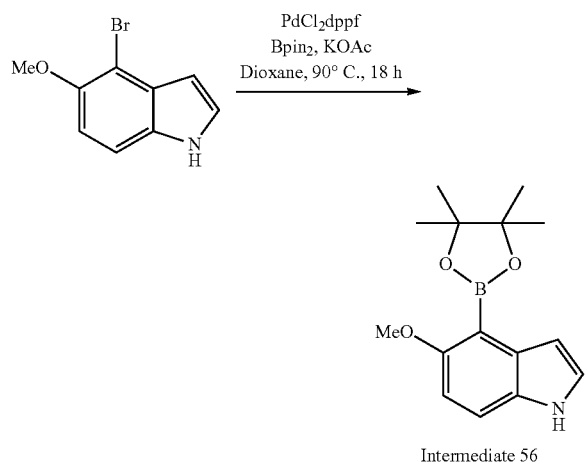

Intermediate 56

To a suspension of 4-bromo-5-methoxy-1H-indole (900 mg, 3.98 mmol), bispinacolatodiboron (5 g, 19.9 mmol, 5 eq), KOAc (1.95 g, 19.9 mmol, 5 eq) in dioxane (30 mL) was added PdCl$_2$dppf (291 mg, 0.40 mmol, 0.1 eq) under Ar(g). The reaction mixture was heated up to 90° C. overnight. It was then re-charged with bispinacolatodiboron (1 g, 4 mmol, 1 eq), KOAc (0.4 g, 4 mmol, 1 eq) and PdCl$_2$dppf (145 mg, 0.20 mmol, 0.05 eq) and heated up to 90° C. another night. It was then cooled down to rt, partitioned with water (40 mL) and extracted with EtOAc (3×50 mL). The combined organics were dried over MgSO$_4$, filtered and the solvent was removed in vacuo. Purification by silica gel column chromatography with hexane/EtOAc (1:0-1:1) yielded Intermediate 56 as a pale yellow solid (425 mg, 39%).

$^1$H NMR (300 MHz, DMSO-d$_6$) δ$_H$: 10.86 (br s, 1H), 7.39 (dd, J=8.7, 0.8 Hz, 1H), 7.29 (t, J=2.7 Hz, 1H), 6.81 (d, J=8.7 Hz, 1H), 6.55 (d, J=2.1 Hz, 1H), 3.72 (s, 3H), 1.32 (s, 12H).

Intermediate 57

3-Fluoro-4-(4,4,5,5-tetramethyl-1,3,2-dioxaborolan-2-yl)-1H-indole

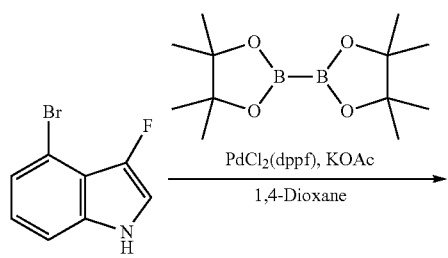

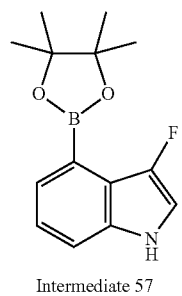

Intermediate 57

To a mixture of 4-bromo-3-fluoro-1H-indole (950 mg, 4.45 mmol, 1.0 eq.), bis(pinacolato)diboron (1.24 g, 1.1 eq.), potassium acetate (1.31 g, 3.0 eq.) and PdCl$_2$(dppf) (162 mg, 0.05 eq.) was added 1,4-dioxane (28.5 mL). The resultant suspension was degassed by sparging with argon and heated to 85° C. for 20 h. The reaction mixture was partitioned between EtOAc (200 mL), water (100 mL) and brine (100 ml). The aqueous phase was re-extracted with EtOAc (2×50 mL) and the combined organics were washed with brine (50 mL), and dried over MgSO4. The drying agent was removed by filtration and the solvent removed in vacuo to afford dark solids that were purified by flash chromatography on silica with hexane/CH$_2$Cl$_2$ (1:0-1:4) to afford Intermediate 57 as a light green solid (458 mg, 39%).

$^1$H NMR (DMSO-d$_6$) δ$_H$: 10.65-11.10 (m, 1H), 7.46 (ddd, J=8.1, 2.7, 1.0 Hz, 1H), 7.37 (dd, J=7.0, 0.9 Hz, 1H), 7.32 (t, J=2.6 Hz, 1H), 7.12 (dd, J=8.2, 7.1 Hz, 1H), 1.21-1.40 (m, 12H)

Intermediate 58

3-Methyl-4-(4,4,5,5-tetramethyl-1,3,2-dioxaborolan-2-yl)-1H-indole

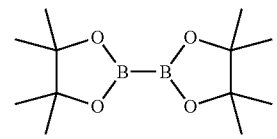

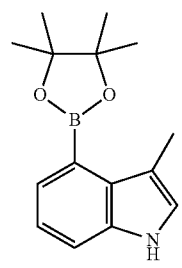

Intermediate 58

To a mixture of 4-bromo-3-methyl-1H-indole (972 mg, 4.63 mmol, 1.0 eq.), bis(pinacolato)diboron (1.29 g, 1.1 eq.), potassium acetate (1.36 g, 3.0 eq.) and PdCl$_2$(dppf) (102 mg, 0.03 eq.) was added 1,4-dioxane (30 mL). The resultant suspension was degassed by vac-purging and heated to 80° C. for 22 h. The reaction mixture was partitioned between EtOAc (50 mL), water (25 mL) and brine (25 ml). The aqueous phase was re-extracted with EtOAc (2×15 mL) and the combined organics were washed with brine (15 mL), and dried over MgSO4. The drying agent was removed by filtration and the solvent removed in vacuo to afford brown solids that were purified by flash chromatography on silica with hexane/CH$_2$Cl$_2$ (1:0-1:1) to afford Intermediate 58 as a white solid (325 mg, 27%).

$^1$H NMR (DMSO-d$_6$) $\delta_H$: 10.79 (br s, 1H), 7.43 (dd, J=8.1, 1.1 Hz, 1H), 7.30 (dd, J=7.0, 1.1 Hz, 1H), 7.09-7.18 (m, 1H), 7.03 (dd, J=8.0, 7.1 Hz, 1H), 2.36 (s, 3H), 1.33 (s, 12H)

Intermediate 59

6-Chloro-4-(4,4,5,5-tetramethyl-1,3,2-dioxaborolan-2-yl)-1H-indole

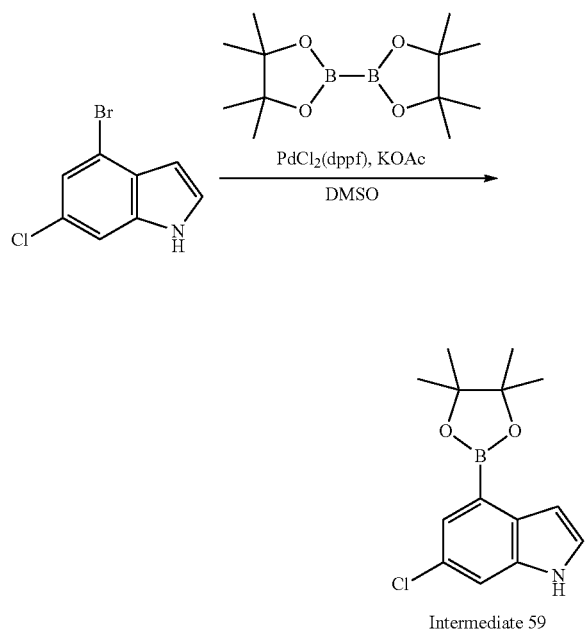

Intermediate 59

To a mixture of 4-bromo-6-chloro-1H-indole (917 mg, 3.98 mmol, 1.0 eq.), bis(pinacolato)diboron (1.11 g, 1.1 eq.), potassium acetate (1.17 g, 3.0 eq.) and PdCl$_2$(dppf) (87 mg, 0.03 eq.) was added DMSO (27.5 mL). The resultant suspension was degassed by vac-purging and heated to 70° C. for 22 h. The reaction mixture was concentrated under reduced pressure and the residue partitioned between EtOAc (150 mL), water (75 mL) and brine (75 ml). The aqueous phase was re-extracted with EtOAc (50 mL) and the combined organics were washed with a mixture of water (25 mL) and brine (25 mL) followed by brine (50 mL), and dried over MgSO4. The drying agent was removed by filtration and the solvent removed in vacuo to afford dark solids that were purified by flash chromatography on silica with hexane/CH$_2$Cl$_2$ (1:0-1:1) to afford Intermediate 59 as white solids (291 mg, 26%).

$^1$H NMR (DMSO-d$_6$) $\delta_H$: 11.24 (br s, 1H), 7.55 (dd, J=2.0, 0.8 Hz, 1H), 7.37-7.47 (m, 1H), 7.30 (d, J=2.1 Hz, 1H), 6.73 (ddd, J=3.0, 2.0, 0.8 Hz, 1H), 1.33 (s, 12H).

Intermediate 60

4-(4,4,5,5-Tetramethyl-1,3,2-dioxaborolan-2-yl)-1H-indole-3-carbonitrile

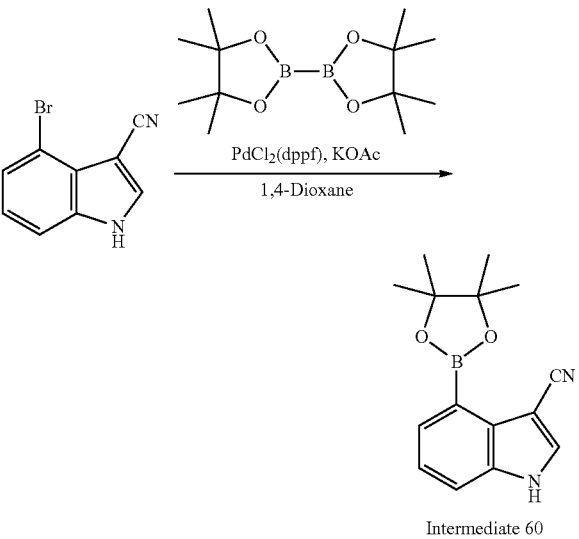

Intermediate 60

To a mixture of 4-bromo-1 H-indole-3-carbonitrile (905 mg, 4.09 mmol, 1.0 eq.), bis(pinacolato)diboron (1.14 g, 1.1 eq.), potassium acetate (1.21 g, 3.0 eq.) and PdCl$_2$(dppf) (300 mg, 0.1 eq.) was added 1,4-dioxane (30 mL). The resultant suspension was degassed by vac-purging and heated to 90° C. for 19 h. The reaction mixture was partitioned between EtOAc (100 mL), water (30 mL) and brine (30 ml). The aqueous phase was re-extracted with EtOAc (3×25 mL) and the combined organics were dried over MgSO4. The drying agent was removed by filtration and the solvent removed in vacuo to afford a viscous brown oil that was purified by flash chromatography on silica with CH$_2$Cl$_2$/EtOAc (1:0-9:1) to afford orange solids (616 mg). Material dissolved in EtOAc (24 mL) and treated with activated carbon (180 mg) at 85° C. for 4 h before filtering and removal of solvent in vacuo to afford Intermediate 60 as a pale orange solid (555 mg, 50%).

$^1$H NMR (DMSO-d$_6$) $\delta_H$: 12.22 (br s, 1H), 8.28 (d, J=3.0 Hz, 1H), 7.64 (dd, J=8.1, 1.1 Hz, 1H), 7.49 (dd, J=7.1, 1.0 Hz, 1H), 7.26 (dd, J=8.2, 7.1 Hz, 1H), 1.35 (s, 12H).

Example A

4-{[4-(1H-Indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}-1λ$^6$-thiomorpholine-1,1-dione

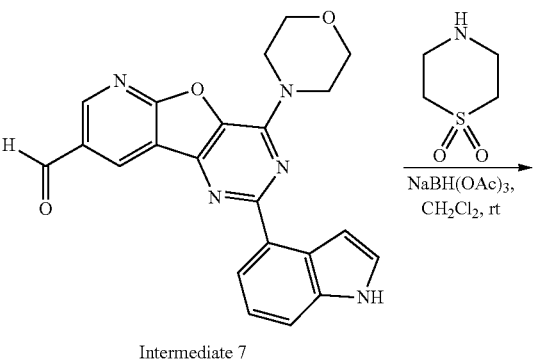

Intermediate 7

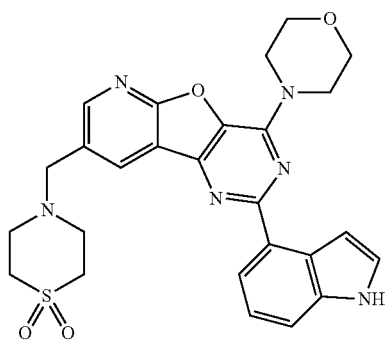

Example A

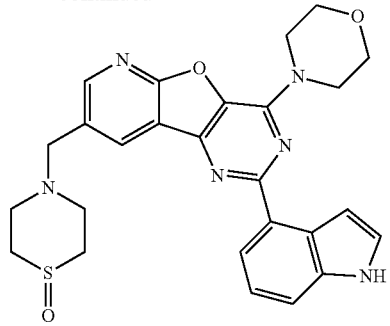

Example B

To a suspension of MP-TMT Pd-scavenged Intermediate 7 (30 mg, 0.075 mmol, 1 eq) and thiomorpholine 1,1-dioxide (20 mg, 0.15 mmol, 2 eq) in anhydrous $CH_2Cl_2$ (7 mL) was added $NaBH(OAc)_3$ (32 mg, 0.15 mmol, 2 eq). The reaction mixture was stirred at rt overnight. Then, it was partitioned with 1N NaOH (10 mL), extracted with $CH_2Cl_2$ (2×10 mL). The combined organic extracts were washed with brine (10 mL) then dried over $MgSO_4$ and the solvent was removed in vacuo. Purification by silica gel column chromatography with $CH_2Cl_2$/MeOH (1:0-49:1 modified with 3 drops 7M $NH_3$ in MeOH per 200 mL of eluent) yielded Example A as a white solid (23 mg, 59%).

$^1$H NMR (300 MHz, $CDCl_3$) $\delta_H$: 8.61 (d, J=2.0 Hz, 1H), 8.54 (d, J=2.1 Hz, 1H), 8.39 (br s, 1H), 8.24 (d, J=7.3 Hz, 1H), 7.58-7.64 (m, 1H), 7.54 (d, J=8.0 Hz, 1H), 7.40 (t, J=2.8 Hz, 1H), 7.34 (t, J=7.8 Hz, 1H), 4.23-4.30 (m, 4H), 3.91-3.98 (m, 4H), 3.87 (s, 2H), 3.03-3.15 (m, 8H).

MS (ES$^+$) 518.9 (100%, [M+H]$^+$).

Example B

4-{[4-(1H-Indol-4-yl)-6-(morpholin-4-yl)-8-oxa-3,5, 10-triazatricyclo[7.4.0.0$^{2,7}$]trideca-1(13),2(7),3,5,9, 11-hexaen-12-yl]methyl}-1λ$^4$-thiomorpholin-1-one

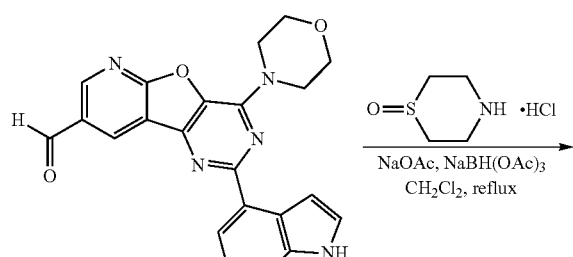

Intermediate 7

Intermediate 7 (17.86 g, 44.7 mmol), 1-oxide thiomorpholine hydrochloride (10.5 g, 67.1 mmol, 1.5 eq) and NaOAc (5.87 g, 71.5 mmol, 1.6 eq) were suspended in anhydrous $CH_2Cl_2$ (450 mL) under Ar(g). The reaction mixture was then refluxed for 6 h, then cooled down to rt and $NaBH(OAc)_3$ (16.1 g, 76 mmol, 1.7 eq) was slowly added over 15 mins. The mixture was left to stir at rt for 18 h. The mixture was then re-charged with 1-oxide thiomorpholine hydrochloride (10.5 g, 67.1 mmol, 1.5 eq), NaOAc (5.87 g, 71.5 mmol, 1.6 eq) and $NaBH(OAc)_3$ (16.1 g, 76 mmol, 1.7 eq). After 6 h stirring, the mixture was quenched with $H_2O$ (300 mL) and extracted with $CH_2Cl_2$ (2×300 mL). The combined organic extracts were washed with 50% brine (50 mL) then dried over $MgSO_4$ and the solvent was removed in vacuo. Pd-scavenge was carried out in $CH_2Cl_2$/MeOH (1:1, 100 mL) using MP-TMT resin (18 g, 0.68 mmol/g) over 18 h. The next day, the resin was filtered off, washed with $CH_2Cl_2$/MeOH (1:1, 20 mL) and the solvent was removed in vacuo. Purification by silica gel column chromatography with EtOAc/MeOH (1:0-4:1) followed by $CH_2Cl_2$/MeOH (1:0-9:1) yielded Example B as an off-white solid (13.0 g, 58%).

$^1$H NMR (300 MHz, DMSO-$d_6$) $\delta_H$: 11.27 (br s, 1H), 8.62 (d, J=3.2 Hz, 2H), 8.18 (d, J=7.5 Hz, 1H), 7.44-7.59 (m, 3H), 7.23 (t, J=7.7 Hz, 1H), 4.13 (d, J=4.7 Hz, 4H), 3.84-3.93 (m, 4H), 3.83 (s, 2H), 2.84-3.03 (m, 4H), 2.64-2.83 (m, 4H).

MS (ES$^+$) 503.0 (100%, [M+H]$^+$).

The mesylate salt can be prepared using conventional chemistry known in the art, for example by treating compound B with methanesulfonic acid.

Example C

{[4-(1H-Indol-4-yl)-6-(morpholin-4-yl)-8-oxa-3,5, 10-triazatricyclo[7.4.0.0$^{2,7}$]trideca-1(13),2(7),3,5,9, 11-hexaen-12-yl]methyl}(2-methanesulfonylethyl) methylamine

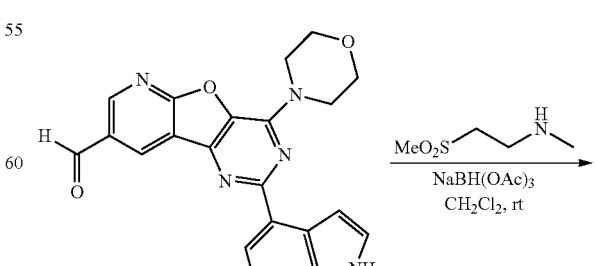

Intermediate 7

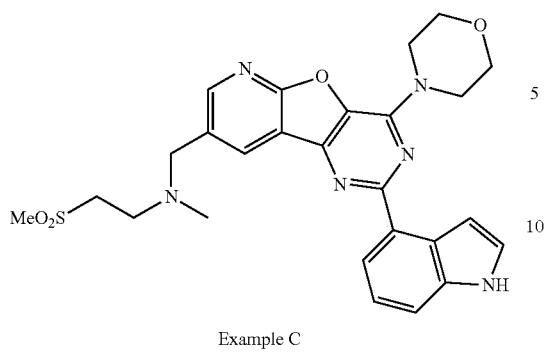

Example C

MP-TMT Pd-scavenged Intermediate 7 (125 mg, 0.31 mmol) and 2-(methylamino)-1-(methylsulfonyl)ethane (116 uL, 0.93 mmol, 3 eq) were suspended in $CH_2Cl_2$ (16 mL) at rt. The mixture was stirred for 15 mins then $NaBH(OAc)_3$ (131 mg, 0.62 mmol, 2 eq) was added. The resulting suspension was stirred at rt overnight. The reaction mixture was then partitioned with 0.5 N NaOH (8 mL) and extracted with $CH_2Cl_2$ (2×10 mL). The combined organics were washed with 50% brine (5 mL) then dried over $MgSO_4$ and the solvent was removed in vacuo. The residue was dissolved in DMSO (2 mL) and purified by basic preparative LCMS to yield Example C as a white solid (67.3 mg, 41%).

$^1$H NMR (300 MHz, DMSO-$d_6$) $\delta_H$: 11.29 (br s, 1H), 8.60-8.62 (m, 1H), 8.59 (d, J=1.8 Hz, 1H), 8.18 (d, J=7.6 Hz, 1H), 7.52-7.57 (m, 2H), 7.48-7.51 (m, 1H), 7.23 (t, J=7.8 Hz, 1H), 4.08-4.17 (m, 4H), 3.86 (m, 4H), 3.77 (s, 2H), 3.42 (t, J=6.9 Hz, 2H), 3.04 (s, 3H), 2.87 (t, J=6.9 Hz, 2H), 2.22 (s, 3H).

MS (ES$^+$) 521.1 (100%, [M+H]$^+$).

Example D

4-{([4-(6-Fluoro-1H-indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}-1λ$^4$-thiomorpholin-1-one

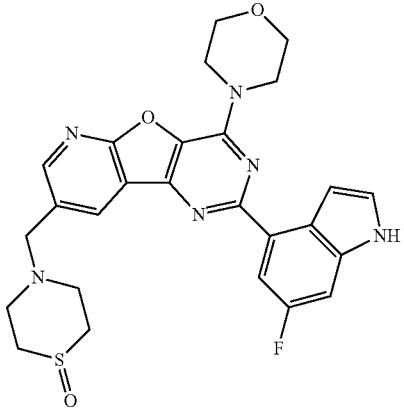

Example D

To Intermediate 8 (65 mg, 0.15 mmol, 1 eq) was added 6-fluoro-4-(tetramethyl-1,3,2-dioxaborolan-2-yl)-1H-indole (80 mg, 0.31 mmol, 2 eq), $PdCl_2(PPh_3)_2$ (22 mg, 0.031 mmol, 0.2 eq) and sodium carbonate (33 mg, 0.31 mmol, 2 eq) in dioxane (1.3 mL)/water (0.4 mL). The reaction mixture was heated at 95° C. for 2 h until completion. It was then cooled down to rt, partitioned with brine (20 mL), and extracted with $CH_2Cl_2$ (3×15 mL). The combined organics were dried over $MgSO_4$, filtered and the solvent was removed in vacuo. The residue was dissolved in $CH_2Cl_2$/MeOH (4:1, 10 mL) and swirled with MP-TMT resin (~140 mg, 1.1 mmol/g, 5 eq) overnight. Upon filtration, the solvent was removed in vacuo. Purification by silica gel column chromatography with EtOAc/MeOH (1:0-4:1) yielded the Example D as a pale yellow solid (26 mg, 33%).

$^1$H NMR (300 MHz, DMSO-$d_6$) $\delta_H$: 11.35 (br s, 1H), 8.65 (d, J=1.9 Hz, 1H), 8.62 (d, J=2.1 Hz, 1H), 7.97 (dd, J=11.6, 2.4 Hz, 1H), 7.46-7.57 (m, 2H), 7.34 (dd, J=9.3, 1.8 Hz, 1H), 4.05-4.21 (m, 4H), 3.77-3.92 (m, 6H), 2.84-3.05 (m, 4H), 2.66-2.84 (m, 4H).

MS (ES$^+$) 521.0 (100%, [M+H]$^+$).

Example E

4-{([4-(5-Fluoro-1H-indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}-1λ$^4$-thiomorpholin-1-one

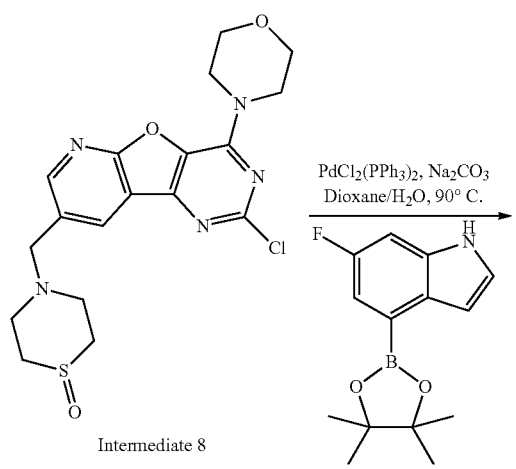

Intermediate 8

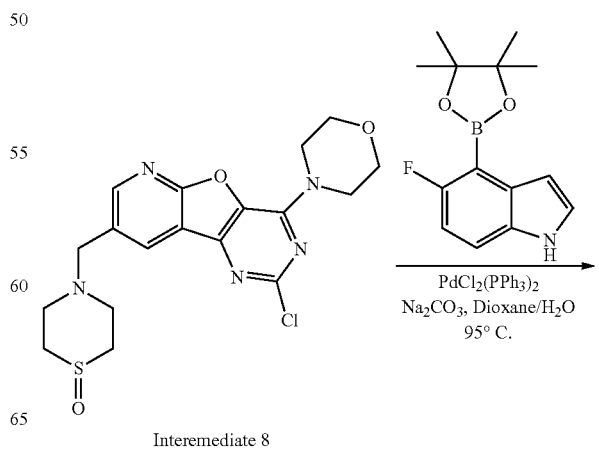

Interemediate 8

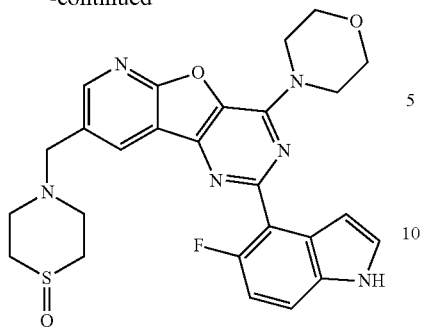

Example E

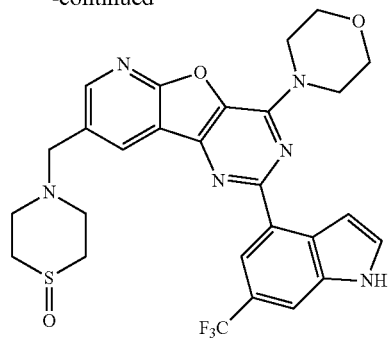

Example F

To Intermediate 8 (73 mg, 0.173 mmol, 1 eq) was added 5-fluoro-4-(tetramethyl-1,3,2-dioxaborolan-2-yl)-1H-indole (136 mg, 0.52 mmol, 3 eq), PdCl$_2$(PPh$_3$)$_2$ (24 mg, 0.035 mmol, 0.2 eq) and sodium carbonate (37 mg, 0.35 mmol, 2 eq) in dioxane (8 mL)/water (2 mL). The reaction mixture was heated at 95° C. overnight. The mixture was then-recharged with 5-fluoro-4-(tetramethyl-1,3,2-dioxaborolan-2-yl)-1H-indole (136 mg, 0.52 mmol, 3 eq), PdCl$_2$(PPh$_3$)$_2$ (24 mg, 0.035 mmol, 0.2 eq) and sodium carbonate (37 mg, 0.35 mmol, 2 eq), then re-heated to 90° C. overnight. It was then cooled down to rt, partitioned with water (15 mL) and extracted with EtOAc (3×15 mL). The combined organics were dried over MgSO$_4$, filtered and the solvent was removed in vacuo. The residue was dissolved in CH$_2$Cl$_2$/MeOH (1:1, 10 mL) and swirled with MP-TMT resin (~350 mg, 1.1 mmol/g, 5 eq) overnight. Upon filtration, the solvent was removed in vacuo. Purification by silica gel column chromatography with EtOAc/MeOH (1:0-4:1) yielded Example E as a white solid (32.7 mg, 67%).

$^1$H NMR (300 MHz, DMSO-d$_6$) δ$_H$: 11.29 (br. s., 1H), 8.62 (d, J=1.9 Hz, 1H), 8.56 (d, J=1.9 Hz, 1H), 7.43-7.52 (m, 2H), 6.97-7.09 (m, 1H), 6.75 (m, 1H), 4.02-4.14 (m, 4H), 3.76-3.88 (m, 6H), 2.83-3.01 (m, 4H), 2.65-2.82 (m, 4H).

MS (ES$^+$) 521.2 (100%, [M+H]$^+$).

Example F

4-{([6-(Morpholin-4-yl)-4-[6-(trifluoromethyl)-1H-indol-4-yl]-8-oxa-3,5,10-triazatricyclo[7.4.0.0$^{2,7}$]trideca-1(13),2(7),3,5,9,11-hexaen-12-yl]methyl}-1λ$^4$-thiomorpholin-1-one To Intermediate 8 (75 mg, 0.178 mmol, 1 eq) was added 4-(tetramethyl-1,3,2-dioxaborolan-2-yl)-6-(trifluoromethyl)-1H-indole (111 mg, 0.36 mmol, 2 eq), PdCl$_2$(PPh$_3$)$_2$ (25 mg, 0.036 mmol, 0.2 eq) and sodium carbonate (57 mg, 0.53 mmol, 3 eq) in dioxane (3 mL)/water (0.7 mL). The reaction mixture was heated at 90° C. for 1 h until completion. It was then cooled down to rt, partitioned with water (15 mL) and extracted with EtOAc (3×15 mL). The combined organics were dried over MgSO$_4$, filtered and the solvent was removed in vacuo. The residue was dissolved in CH$_2$Cl$_2$/MeOH (1:1, 10 mL) and swirled with MP-TMT resin (~250 mg, 1.1 mmol/g, 5 eq) overnight. Upon filtration, the solvent was removed in vacuo. Purification by silica gel column chromatography with EtOAc/MeOH (1:0-4:1) yielded the Example F as a white solid (73.6 mg, 72%).

$^1$H NMR (300 MHz, DMSO-d$_6$) δ$_H$: 11.74 (br s, 1H), 8.68 (d, J=2.1 Hz, 1H), 8.63 (d, J=2.1 Hz, 1H), 8.43 (d, J=1.3 Hz, 1H), 7.85-7.91 (m, 1H), 7.76 (t, J=2.6 Hz, 1H), 7.57-7.64 (m, 1H), 4.08-4.20 (m, 4H), 3.85-3.93 (m, 4H), 3.84 (s, 2H), 2.84-3.03 (m, 4H), 2.67-2.81 (m, 4H).

MS (ES$^+$) 570.9 (100%, [M]$^+$).

Example G

1-Imino-4-{([4-(1H-indol-4-yl)-6-(morpholin-4-yl)-8-oxa-3,5,10-triazatricyclo[7.4.0.0$^{2,7}$]trideca-1(13),2,4,6,9,11-hexaen-12-yl]methyl}-1λ$^6$-thiomorpholin-1-one

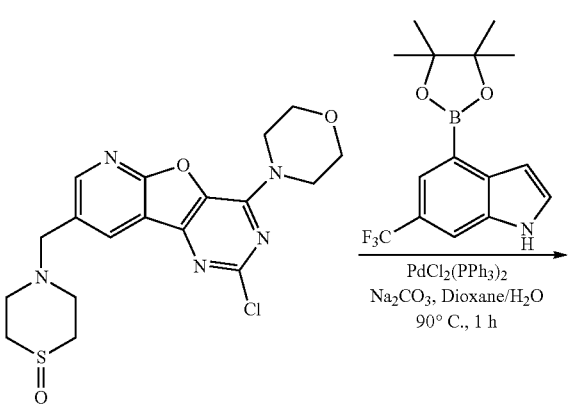

Interemediate 8

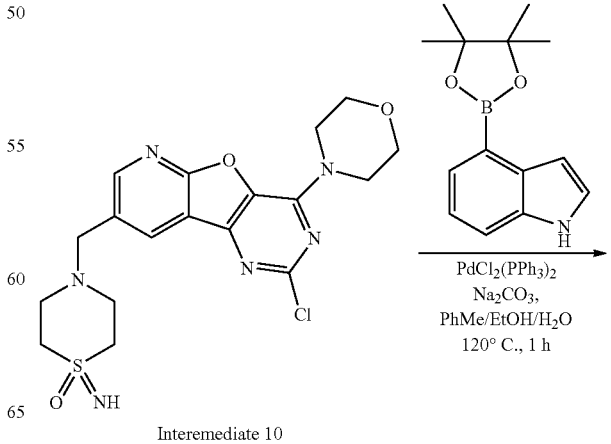

Interemediate 10

75

-continued

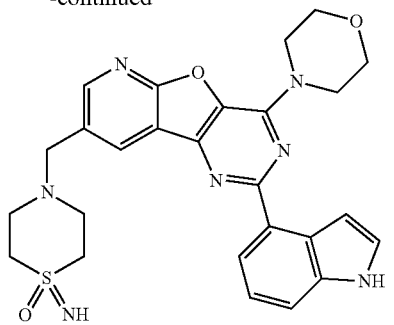

Example G

Intermediate 10 (0.044 g, 0.1 mmol), 4-(tetramethyl-1,3,2-dioxaborolan-2-yl)-1H-indole (0.029 g, 0.12 mmol), PdCl$_2$(PPh$_3$)$_2$ (0.007 g, 0.01 mmol) and sodium carbonate (0.032 g, 0.3 mmol) were placed in a microwave vial. Ethanol (1 mL), toluene (1.6 mL) and water (0.5 mL) were added and the reaction mixture was degassed, placed under an argon atmosphere and heated in a microwave to 120° C. for 1 h. Upon cooling to rt the reaction mixture was poured into water (20 ml) and extracted twice with CH$_2$Cl$_2$ (20 mL). The combined organic fractions were dried over MgSO$_4$, filtered and the solvent removed by evaporation in vacuo. Purification by flash silica column chromatography, 5% MeOH/CH$_2$Cl$_2$ elution, gave Example G in 54% yield (0.028 g).

$^1$H NMR (300 MHz, DMSO-d$_6$) $\delta_H$: 11.27 (br s, 1H), 8.64 (dd, J=8.29, 2.07 Hz, 2H), 8.19 (d, J=7.35 Hz, 2H), 7.47-7.48 (m, 3H), 7.23 (t, J=7.72 Hz, 1H), 4.02-4.20 (m, 4H), 3.92 (s, 2H), 3.81-3.96 (m, 4H), 3.62 (br s, 1H), 2.82-3.06 (m, 8H).

MS (ES$^+$) 518.2 (100%, [M+H]$^+$).

Example H

4-[(1R)-1-[4-(1H-Indol-4-yl)-6-(morpholin-4-yl)-8-oxa-3,5,10-triazatricyclo[7.4.0.0$^{2,7}$]trideca-1(13),2,4,6,9,11-hexaen-12-yl]ethyl]-1λ$^6$-thiomorpholine-1,1-dione

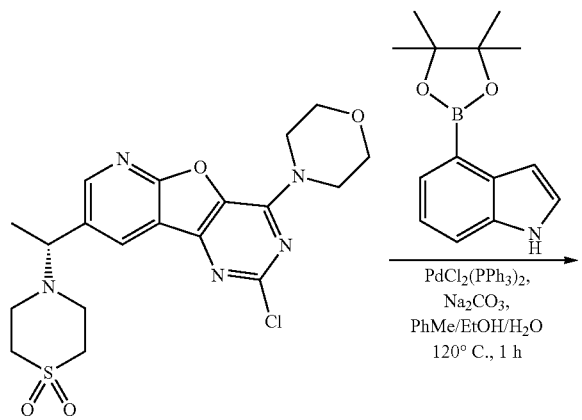

Interemediate 14

76

-continued

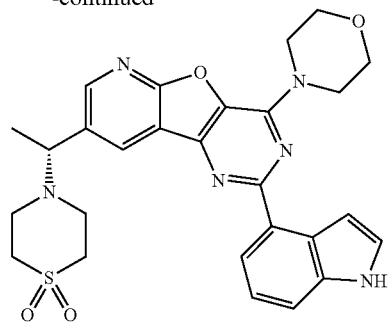

Example H

Intermediate 14 (0.065 g, 0.144 mmol), 4-(tetramethyl-1,3,2-dioxaborolan-2-yl)-1H-indole (0.042 g, 0.173 mmol), PdCl$_2$(PPh$_3$)$_2$ (0.01 g, 0.0144 mmol) and sodium carbonate (0.045 g, 0.432 mmol) were placed in a microwave vial. Ethanol (1 ml), toluene (1.6 ml) and water (0.5 ml) were added and the reaction mixture was degassed, placed under an argon atmosphere and heated in a microwave to 120° C. for 60 min. Upon cooling to rt the reaction mixture was poured into water (20 ml) and extracted twice with CH$_2$Cl$_2$ (20 mL). The combined organic fractions were dried over MgSO$_4$, filtered and the solvent removed by evaporation in vacuo. Purification by flash silica column chromatography with CH$_2$Cl$_2$/MeOH (1:0-19:1) followed by crystallisation from EtOAc gave Example H (0.032 g, 42%).

$^1$H NMR (300 MHz, DMSO-d$_6$) $\delta_H$: 11.28 (br s, 1H), 8.70 (d, J=2.1 Hz, 1H), 8.65 (d, J=1.9 Hz, 1H), 8.20 (d, J=7.5 Hz, 1H), 7.47-7.57 (m, 3H), 7.23 (t, J=7.7 Hz, 1H), 4.28 (q, J=6.8 Hz, 1H), 3.99-4.20 (m, 4H), 3.82-3.92 (m, 4H), 3.06-3.17 (m, 4H), 2.82-3.05 (m, 4H), 1.52 (d, J=6.8 Hz, 3H).

MS (ES$^+$) 533.2 (100%, [M+H]$^+$).

Example I

4-[(1S)-1-[4-(1H-Indol-4-yl)-6-(morpholin-4-yl)-8-oxa-3,5,10-triazatricyclo[7.4.0.0$^{2,7}$]trideca-1(13),2,4,6,9,11-hexaen-12-yl]ethyl]-1λ$^6$-thiomorpholine-1,1-dione

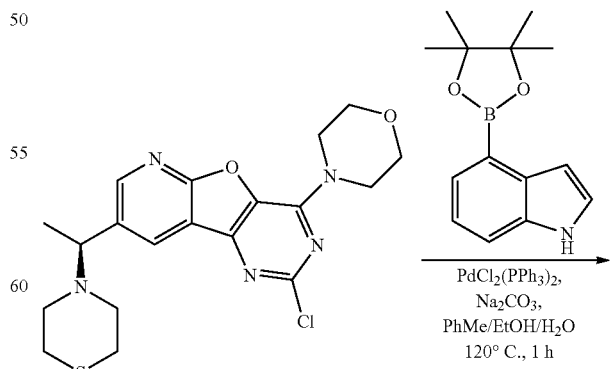

Interemediate 18

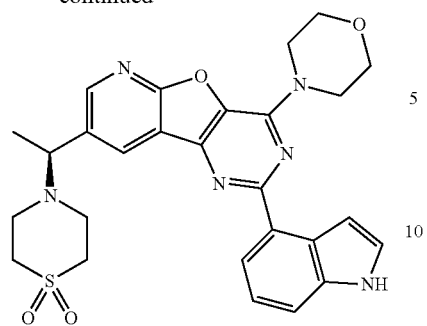

Example I

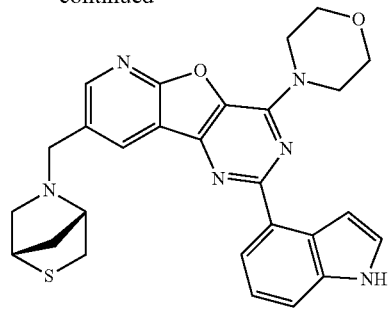

Example J

Intermediate 18 (0.048 g, 0.106 mmol), 4-(tetramethyl-1,3,2-dioxaborolan-2-yl)-1H-indole (0.049 g, 0.2 mmol), PdCl$_2$(PPh$_3$)$_2$ (0.007 g, 0.01 mmol) and sodium carbonate (0.032 g, 0.3 mmol) were placed in a microwave vial. Ethanol (1 ml), toluene (1.6 ml) and water (0.5 ml) were added and the reaction mixture was degassed, placed under an argon atmosphere and heated in a microwave to 120° C. for 1 h. Upon cooling to rt the reaction mixture was poured into water (20 ml) and extracted twice with CH$_2$Cl$_2$ (20 mL). The combined organic fractions were dried over MgSO$_4$, filtered and the solvent removed by evaporation in vacuo. Purification by flash silica column chromatography with CH$_2$Cl$_2$/MeOH (1:0-19:1) followed by crystallisation from EtOAc gave Example I (0.027 g, 48%).

$^1$H NMR (300 MHz, DMSO-d$_6$) δ$_H$: 11.27 (br s, 1H), 8.68-8.72 (m, 1H), 8.65 (br d, J=1.9 Hz, 1H), 8.20 (d, J=6.6 Hz, 1H), 7.46-7.57 (m, 3H), 7.23 (t, J=7.7 Hz, 1H), 4.27 (q, J=6.8 Hz, 1H), 4.09-4.18 (m, 4H), 3.82-3.92 (m, 4H), 3.07-3.16 (m, 4H), 2.82-3.05 (m, 4H), 1.53 (d, J=6.8 Hz, 3H).

MS (ES$^+$) 533.2 (100%, [M+H]$^+$).

Example J 4-(1H-Indol-4-yl)-6-(morpholin-4-yl)-12-[(1 S,4S)-2-thia-5-azabicyclo[2.2.1]heptan-5-ylmethyl]-8-oxa-3,5,10-triazatricyclo[7.4.0.0$^{2,7}$]trideca-1(13),2,4,6,9,11-hexaene Intermediate 23 (0.042 g, 0.1 mmol), 4-(tetramethyl-1,3,2-dioxaborolan-2-yl)-1H-indole (0.049 g, 0.2 mmol), PdCl$_2$(PPh$_3$)$_2$ (0.007 g, 0.01 mmol) and sodium carbonate (0.032 g, 0.3 mmol) were placed in a microwave vial. Ethanol (1 mL), toluene (1.6 mL) and water (0.5 mL) were added and the reaction mixture was degassed, placed under an argon atmosphere and heated in a microwave to 120° C. for 1 h. Upon cooling to rt, the reaction mixture was poured into water (20 mL) and extracted twice with CH$_2$Cl$_2$ (20 mL). The combined organic fractions were dried over MgSO$_4$, filtered and the solvent removed by evaporation in vacuo. Purification by flash silica column chromatography, EtOAc elution, followed by recrystallization form EtOH gave Example J (0.037 g, 74%).

$^1$H NMR (300 MHz, DMSO-d$_6$) δ$_H$: 11.27 (br s, 1H), 8.61 (s, 2H), 8.18 (d, J=7.4 Hz, 1H), 7.46-7.57 (m, 3H), 7.23 (t, J=7.7 Hz, 1H), 4.13 (br d, J=4.3 Hz, 4H), 3.97 (s, 2 H), 3.87 (br s, 4H), 3.78 (br s, 1H), 3.52 (br s, 1H), 3.13 (br d, J=9.4 Hz, 2H), 2.74-2.89 (m, 2H), 2.15-2.26 (m, 1H), 1.72 (br d, J=10.2 Hz, 1H).

MS (ES$^+$) 499.1 (100%, [M+H]$^+$).

Example K (1S,4S)-5-{[4-(1H-Indol-4-yl)-6-(morpholin-4-yl)-8-oxa-3,5,10-triazatricyclo[7.4.0.0$^{2,7}$]trideca-1(13),2,4,6,9,11-hexaen-12-yl]methyl}-2λ$^6$-thia-5-azabicyclo[2.2.1]heptane-2,2-dione

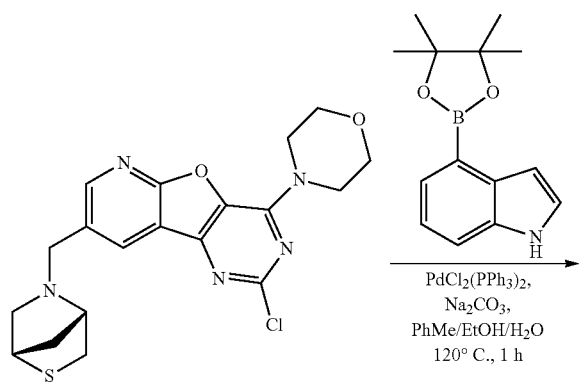

Interemediate 23

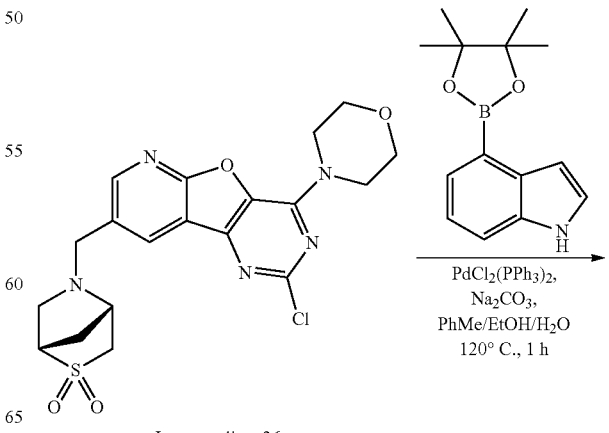

Interemediate 26

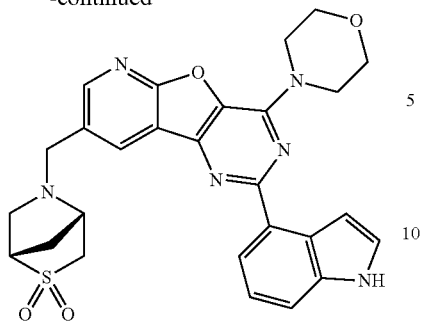

Example K

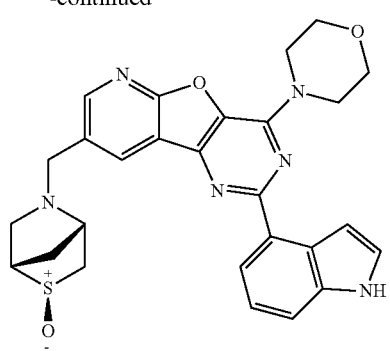

Example L

Intermediate 26 (0.045 g, 0.1 mmol), 4-(tetramethyl-1,3,2-dioxaborolan-2-yl)-1H-indole (0.049 g, 0.2 mmol), PdCl$_2$(PPh$_3$)$_2$ (0.007 g, 0.01 mmol) and sodium carbonate (0.032 g, 0.3 mmol) were placed in a microwave vial. Ethanol (1 mL), toluene (1.6 mL and water (0.5 mL) were added and the reaction mixture was degassed, placed under an argon atmosphere and heated in a microwave to 120° C. for 1 h. Upon cooling to rt, the reaction mixture was poured into water (20 mL) and extracted twice with CH$_2$Cl$_2$ (20 mL). The combined organic fractions were dried over MgSO$_4$, filtered and the solvent removed by evaporation in vacuo. Purification by flash silica column chromatography, 5% MeOH/CH$_2$Cl$_2$ elution, a further column, 10% MeOH/EtOAc elution followed by recrystallization form EtOAc gave Example K in 60% yield (0.032 g).

$^1$H NMR (300 MHz, DMSO-d$_6$) δ$_H$: 11.27 (br s, 1H), 8.64 (s, 2H), 8.19 (d, J=7.5 Hz, 1H), 7.52 (m, 3H), 7.23 (t, J=7.7 Hz, 1H), 4.13 (m, 4H), 4.03 (s, 2H), 3.87 (m, 4H), 3.78 (m, 2H), 3.39 (m, 1H), 3.17 (m,1H), 3.05 (m, 2H), 2.35 (m, 2H).

MS (ES$^+$) 530.2 (100%, [M+H]$^+$).

Example L (1S,2R,4S)-5-{([4-(1H-Indol-4-yl)-6-(morpholin-4-yl)-8-oxa-3,5,10-triazatricyclo[7.4.0.0$^{2,7}$]trideca-1(13),2,4,6,9,11-hexaen-12-yl]methyl}-2-thia-5-azabicyclo[2.2.1]heptan-2-ium-2-olate Intermediate 29 (0.043 g, 0.1 mmol), 4-(tetramethyl-1,3,2-dioxaborolan-2-yl)-1H-indole (0.049 g, 0.2 mmol), PdCl$_2$(PPh$_3$)$_2$ (0.007 g, 0.01 mmol) and sodium carbonate (0.032 g, 0.3 mmol) were placed in a microwave vial. Ethanol (1 mL), toluene (1.6 mL and water (0.5 mL) were added and the reaction mixture was degassed, placed under an argon atmosphere and heated in a microwave to 120° C. for 1 h. Upon cooling to rt the reaction mixture was poured into water (20 mL) and extracted twice with CH$_2$Cl$_2$ (20 mL). The combined organic fractions were dried over MgSO$_4$, filtered and the solvent removed by evaporation in vacuo. Purification by flash silica column chromatography, 5% MeOH/CH$_2$Cl$_2$ elution, a further column, 20% MeOH/EtOAc elution, followed by a further column, 10% MeOH/CH$_2$Cl$_2$ elution, gave Example L in 85% yield (0.044 g).

$^1$H NMR (300 MHz, DMSO-d$_6$) δ$_H$: 11.27 (br s, 1H), 8.58 (br s, 2H), 8.18 (d, J=7.5 Hz, 1H), 7.47-7.57 (m, 3H), 7.23 (t, J=7.4 Hz, 1H), 4.13 (br s, 4H), 3.60-3.90 (m, 9 H), 3.00 (br dd, J=11.9, 5.3 Hz, 1H), 2.26 (br s, 2H), 2.15 (br d, J=13.56 Hz, 1H), 1.75 (br d, J=11.87 Hz, 1H).

MS (ES$^+$) 515.1 (100%, [M+H]$^+$).

Example M

4-{[4-(1H-Indol-4-yl)-6-(morpholin-4-yl)-8-thia-3,5,10-triazatricyclo[7.4.0.0$^{2,7}$]trideca-1(13),2(7),3,5,9,11-hexaen-12-yl]methyl}-1λ$^6$-thiomorpholine-1,1-dione

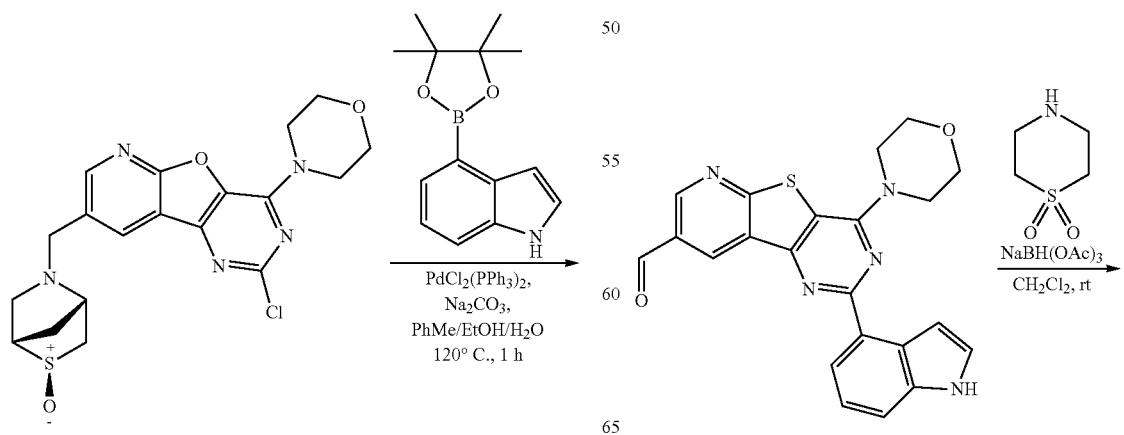

-continued

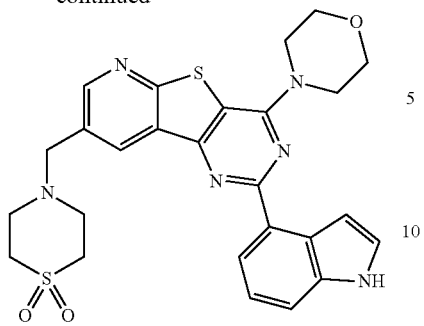

Example M

A suspension of Intermediate 36 (500 mg) and MP-TMT resin (1.77 g, 1.20 mmol) in CH$_2$Cl$_2$/MeOH (4:1, 300 mL) was swirled at rt overnight to remove palladium contaminants. The solution was then filtered, the resin washed with CH$_2$Cl$_2$/MeOH (4:1, 100 mL) and the filtrate concentrated in vacuo to afford 310 mg of Intermediate 36. To a portion of Intermediate 36 (100 mg, 0.242 mmol, 1.0 eq) in anhydrous CH$_2$Cl$_2$ (24 mL) was added thiomorpholine 1,1-dioxide (98.0 mg, 0.725 mmol, 3.0 eq) followed by NaBH(OAc)$_3$ (106 mg, 0.483 mmol, 2.0 eq). The reaction mixture was stirred at rt for 18 h then diltued with CH$_2$Cl$_2$ (10 mL) and quenched with 1 M aqueous NaOH (10 mL). The resulting mixture was extracted with CH$_2$Cl$_2$ (3×20 mL) and the combined organic extracts were dried over MgSO$_4$, filtered, and concentrated in vacuo. Purification by silica gel chromatography using CH$_2$Cl$_2$/MeOH (1:0-49:1) yielded Example M as a white solid (31.8 mg, 25%).

$^1$H NMR (300 MHz, CDCl$_3$) δ$_H$: 11.33 (br. s, 1H), 8.82-8.89 (m, 1H), 8.28 (d, J=7.5 Hz, 1H), 7.50-7.62 (m, 3H), 7.25 (t, J=7.8 Hz, 1H), 4.01-4.14 (m, 4H), 3.98 (s, 2H), 3.80-3.92 (m, 4H), 3.10-3.21 (m, 4H), 2.93-3.05 (m, 4H).

MS (ES$^+$) 535.0 (100%, [M+H]$^+$), 557.0 (15%, [M+Na]$^+$).

Example N

4-[6-(morpholin-4-yl)-12-[(1-oxo-1λ$^4$-thiomorpholin-4-yl)methyl]-8-oxa-3,5,10-triazatricyclo[7.4.0.0$^2$,$^7$]trideca-1(13),2(7),3,5,9,11-hexaen-4-yl]-2,3-dihydro-1H-indol-2-one

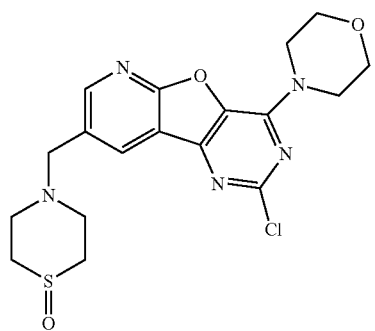

Interemediate 8

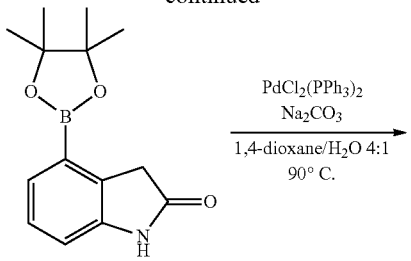

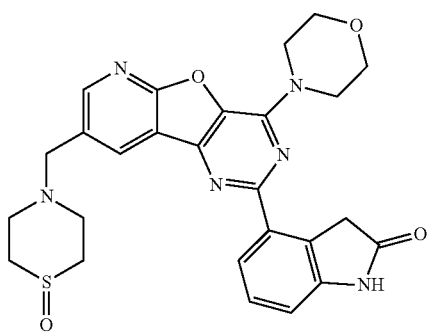

Example N

To a microwave vial containing Intermediate 8 (117 mg, 0.278 mmol, 1.0 eq), (2-oxoindolin-4-yl)boronic acid pinacol ester (152 mg, 0.556 mmol, 2.0 eq), sodium carbonate (58.9 mg, 0.556 mmol, 2.0 eq) and PdCl$_2$(PPh$_3$)$_2$ (39.0 mg, 0.0556 mmol, 20 mol %) was added 1,4-dioxane (1.1 mL) and H$_2$O (0.3 mL). The suspension was stirred at 90° C. for 1 h in a microwave reactor then cooled to rt. An additional portion of PdCl$_2$(PPh$_3$)$_2$ (19.5 mg, 0.0278 mmol, 10 mol %) was added and the reaction mixture was heated at 90° C. for a further 1 h in the microwave. Upon cooling, the mixture was diluted with CH$_2$Cl$_2$ (20 mL) and washed with H$_2$O (20 mL). The aqueous layer was concentrated in vacuo and purified by silica gel column chromatography with CH$_2$Cl$_2$/MeOH (1:0-9:1). The product was re-dissolved in CH$_2$Cl$_2$/MeOH (4:1, 15 mL) and swirled with prewashed MP-TMT resin (200 mg, 0.220 mmol, 3 eq wrt Pd) at rt for 17 h. The solution was filtered and the resin washed with CH$_2$Cl$_2$/MeOH (4:1, 100 mL) to yield Example N as an off-white solid (79.7 mg, 55%).

$^1$H NMR (300 MHz, DMSO-d$_6$) δ$_H$: 10.49 (s, 1H), 8.62 (br s, 2H), 8.02 (d, J=8.1 Hz, 1H), 7.34 (t, J=7.8 Hz, 1H), 6.95 (d, J=7.5 Hz, 1H), 4.04-4.18 (m, 4H), 3.99 (s, 2H), 3.73-3.93 (m, 6H), 2.85-3.06 (m, 4H), 2.66-2.84 (m, 4H).

MS (ES$^+$) 519.2 (100%, [M+H]$^+$), 541.2 (12%, [M+Na]$^+$).

Example O

4-{[4-(2,3-Dihydro-1H-indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}-1λ$^4$-thiomorpholin-1-one

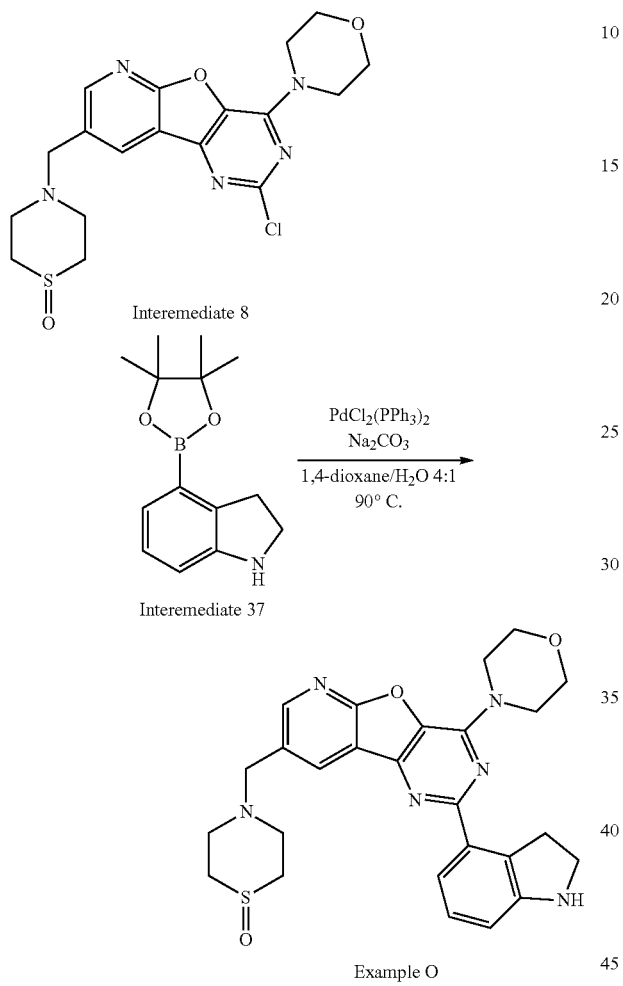

To a microwave vial containing Intermediate 8 (71.2 mg, 0.169 mmol, 1.0 eq), Intermediate 37 (82.9 mg, 0.338 mmol, 2.0 eq), sodium carbonate (35.8 mg, 0.338 mmol, 2.0 eq) and PdCl$_2$(PPh$_3$)$_2$ (23.7 mg, 0.0338 mmol, 20 mol %) was added 1,4-dioxane (0.7 mL) and H$_2$O (0.2 mL). The suspension was stirred at 90° C. for 2 h in a microwave reactor then at 90° C. for 18 h thermally. Upon cooling, the mixture was poured into H$_2$O (20 mL) and extracted with CH$_2$Cl$_2$ (3×20 mL). The combined organic extracts were dried over MgSO$_4$ and filtered before the addition of MeOH (20 mL) and MP-TMT resin (200 mg, 0.220 mmol, 6 eq wrt Pd) and the mixture was swirled at rt for 4 h. The solution was filtered and the resin washed with CH$_2$Cl$_2$/MeOH (4:1, 100 mL). The filtrate was concentrated in vacuo and purified by silica gel column chromatography with EtOAc/MeOH (1:0-6:1) to yield Example O as a yellow solid (53.5 mg, 63%).

$^1$H NMR (300 MHz, DMSO-d$_6$) δ$_H$: 8.60 (d, J=2.1 Hz, 1H), 8.55 (d, J=2.1 Hz, 1H), 7.56 (d, J=7.9 Hz, 1H), 7.05 (t, J=7.8 Hz, 1H), 6.60 (d, J=7.5 Hz, 1H), 5.62 (br s, 1H), 4.02-4.14 (m, 4H), 3.72-3.91 (m, 6H), 3.43-3.54 (m, 4H), 2.67-2.98 (m, 8H).

MS (ES$^+$) 253.2 (100%, [M+2H]$^{2+}$), 505.2 (45%, [M+H]$^+$), 527.2 (7%, [M+Na]$^+$).

Example P

4-{[4-(5-Methyl-1H-indol-4-yl)-6-(morpholin-4-yl)-8-oxa-3,5,10-triazatricyclo[7.4.0.0$^{2,7}$]trideca-1(9),2,4,6,10,12-hexaen-12-yl]methyl}-1λ$^4$-thiomorpholin-1-one

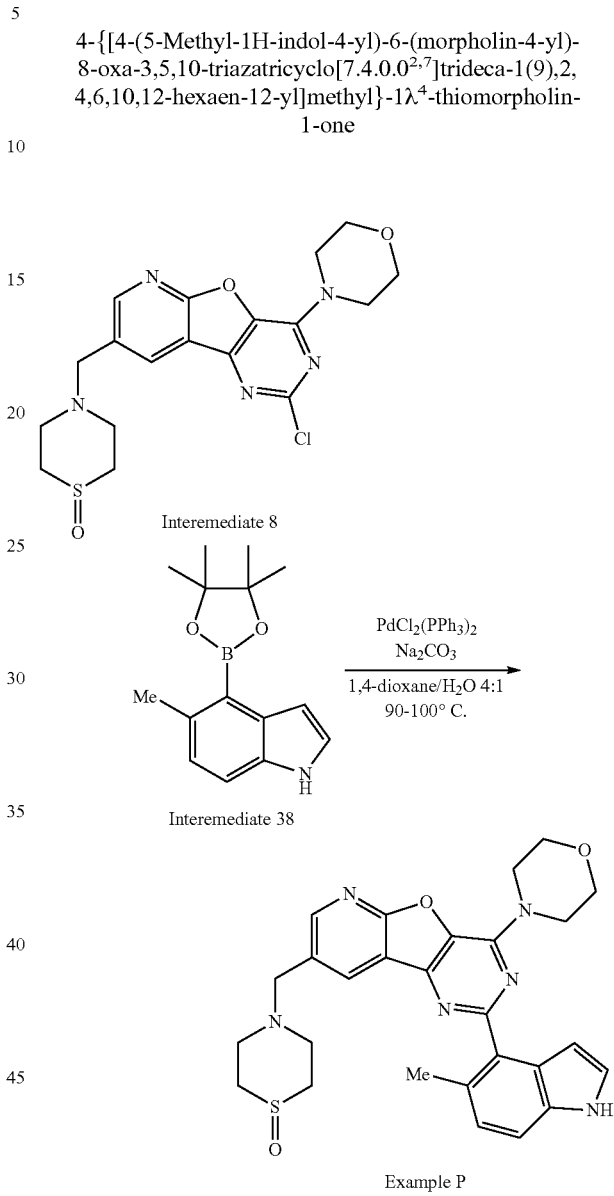

To a microwave vial containing Intermediate 8 (63.8 mg, 0.151 mmol, 1.0 eq), Intermediate 38 (77.8 mg, 0.302 mmol, 2.0 eq), sodium carbonate (32.0 mg, 0.302 mmol, 2.0 eq) and PdCl$_2$(PPh$_3$)$_2$ (21.2 mg, 0.0302 mmol, 20 mol %) was added 1,4-dioxane (0.6 mL) and H$_2$O (0.2 mL). The suspension was stirred at 90° C. for 21 h then cooled to rt. An additional portion of PdCl$_2$(PPh$_3$)$_2$ (10.6 mg, 0.0151 mmol, 10 mol %) was added and the reaction was stirred at 100° C. for 6 h. Upon cooling, the mixture was diluted with CH$_2$Cl$_2$ (10 mL), poured into H$_2$O (20 mL) and extracted with CH$_2$Cl$_2$ (2×20 mL). The combined organic extracts were dried over MgSO$_4$, filtered, concentrated in vacuo and purified by silica gel column chromatography with EtOAc/MeOH (1:0-7:1). The product was re-dissolved in CH$_2$Cl$_2$/MeOH (4:1, 10 mL) and swirled with prewashed MP-TMT resin (200 mg, 0.220 mmol, 5 eq wrt Pd) at rt for 16 h. The solution was filtered and the resin washed with CH$_2$Cl$_2$/MeOH (4:1, 100 mL) The filtrate was concentrated in vacuo and purified a second time by silica gel column chromatography with CH$_2$Cl$_2$/MeOH (1:0-16:1), yielding Example P as a white solid (24.1 mg, 31%).

$^1$H NMR (300 MHz, DMSO-d$_6$) δ$_H$: 11.02 (br s, 1H), 8.62 (d, J=2.1 Hz, 1H), 8.52 (d, J=2.1 Hz, 1H), 7.36 (d, J=8.1 Hz, 1H), 7.28 (t, J=2.7 Hz, 1H), 7.03 (d, J=8.3 Hz, 1H), 6.36-6.43 (m, 1H), 4.05 (d, J=4.5 Hz, 4H), 3.82 (br s, 6H), 2.82-3.00 (m, 4H), 2.65-2.81 (m, 4H), 2.44 (s, 3H).

MS (ES$^+$) 259.1 (100%, [M+2H]$^{2+}$), 517.0 (55%, [M+H]$^+$), 539.0 (7%, [M+Na]$^+$).

Example Q

4-{[4-(7-Fluoro-1H-indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}-1λ$^4$-thiomorpholin-1-one

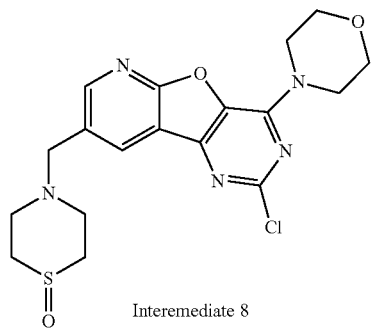

Interemediate 8

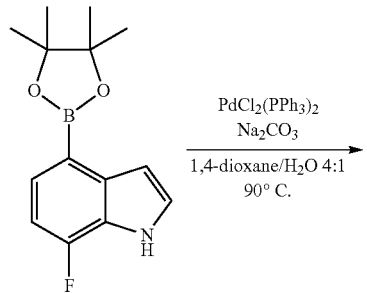

Interemediate 39

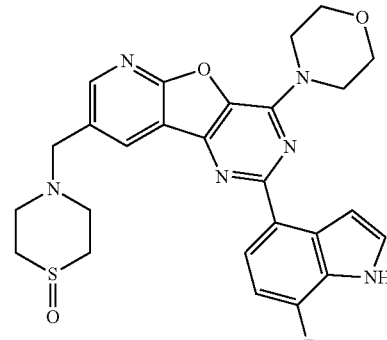

Example Q

To a microwave vial containing Intermediate 8 (69.6 mg, 0.165 mmol, 1.0 eq), Intermediate 39 (86.2 mg, 0.330 mmol, 2.0 eq), sodium carbonate (35.0 mg, 0.330 mmol, 2.0 eq) and PdCl$_2$(PPh$_3$)$_2$ (23.2 mg, 0.0330 mmol, 20 mol %) were added 1,4-dioxane (0.7 mL) and H$_2$O (0.2 mL). The suspension was stirred at 90° C. for 18 h then cooled to rt and concentrated in vacuo. The residue was re-dissolved in CH$_2$Cl$_2$/MeOH (4:1, 30 mL) and swirled with MP-TMT resin (400 mg, 0.440 mmol, 13 eq wrt Pd) at rt for 22 h. The solution was filtered and the resin washed with CH$_2$Cl$_2$/MeOH (4:1, 100 mL). The filtrate was concentrated in vacuo and purified twice by silica gel column chromatography with CH$_2$Cl$_2$/MeOH (1:0-12:1) then CH$_2$Cl$_2$/EtOAc/MeOH (1:0-4:5:1) to yield Example Q as a cream solid (66.0 mg, 77%).

$^1$H NMR (300 MHz, DMSO-d$_6$) δ$_H$: 11.78 (br. s., 1H), 8.56-8.67 (m, 2H), 8.17 (dd, J=8.4, 5.0 Hz, 1H), 7.58-7.65 (m, 1H), 7.55 (t, J=2.6 Hz, 1H), 7.06 (dd, J=10.8, 8.4 Hz, 1H), 4.07-4.20 (m, 4H), 3.76-3.94 (m, 6H), 2.84-3.04 (m, 4H), 2.67-2.83 (m, 4H).

$^{19}$F NMR (282 MHz, DMSO-d$_6$) δ$_F$: −131.07−−130.99 (m, 1F).

MS (ES$^+$) 520.9 (100%, [M+H]$^+$), 542.9 (10%, [M+Na]$^+$).

Example R

4-[6-(morpholin-4-yl)-12-[(1-oxo-1λ$^4$-thiomorpholin-4-yl)methyl]-8-oxa-3,5,10-triazatricyclo[7.4.0.0$^{2,7}$]trideca-1(13),2(7),3,5,9,11-hexaen-4-yl]-1H-indole-6-carbonitrile

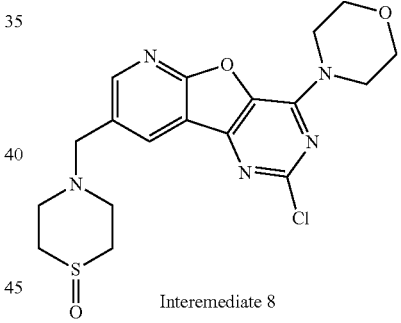

Interemediate 8

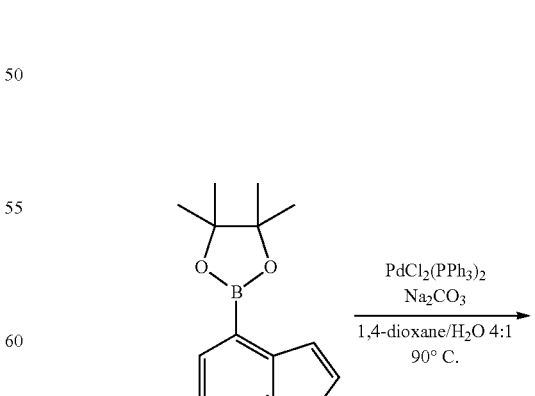

Interemediate 40

Example R

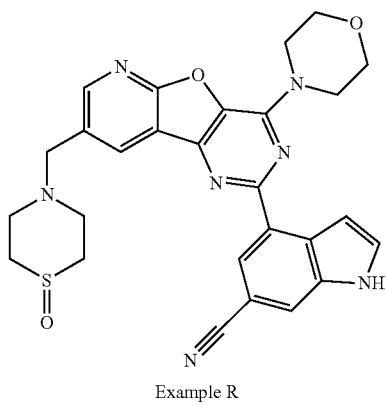

Example R

To a microwave vial containing Intermediate 8 (67.8 mg, 0.161 mmol, 1.0 eq), Intermediate 40 (86.1 mg, 0.321 mmol, 2.0 eq), sodium carbonate (34.0 mg, 0.321 mmol, 2.0 eq) and PdCl$_2$(PPh$_3$)$_2$ (22.5 mg, 0.0321 mmol, 20 mol %) was added 1,4-dioxane (0.6 mL) and H$_2$O (0.2 mL). The suspension was stirred at 90° C. for 16 h then cooled to rt, concentrated in vacuo and purified by silica gel chromatography using CH$_2$Cl$_2$/MeOH (1:0-4:1). The product was redissolved in CH$_2$Cl$_2$/MeOH (4:1, 10 mL) and swirled with MP-TMT resin (200 mg, 0.220 mmol, 7 eq wrt Pd) at rt overnight. The solution was filtered and the resin washed with CH$_2$Cl$_2$/MeOH (4:1, 50 mL). The filtrate was concentrated in vacuo and purified a second time by silica gel chromatography using CH$_2$Cl$_2$/MeOH (1:0-13:1) to yield Example R as a white solid (7.15 mg, 8%).

$^1$H NMR (300 MHz, DMSO-d$_6$) $\delta_H$: 11.88 (br. s., 1H), 8.69 (s, 1H), 8.64 (s, 1H), 8.42 (d, J=1.3 Hz, 1H), 8.03 (s, 1H), 7.79-7.85 (m, 1H), 7.58-7.71 (m, 1H), 4.07-4.23 (m, 4H), 3.78-3.97 (m, 6H), 2.86-3.03 (m, 4H), 2.67-2.82 (m, 4H).

MS (ES$^+$) 264.5 (100%, [M+2H]$^{2+}$), 528.0 (80%, [M+H]$^+$).

Example S

4-{[6-(Morpholin-4-yl)-4-[2-(trifluoromethyl)-1H-indol-4-yl]-8-oxa-3,5,10-triazatricyclo[7.4.0.0$^{2,7}$]trideca-1(9),2,4,6,10,12-hexaen-12-yl]methyl}-1λ$^4$-thiomorpholin-1-one

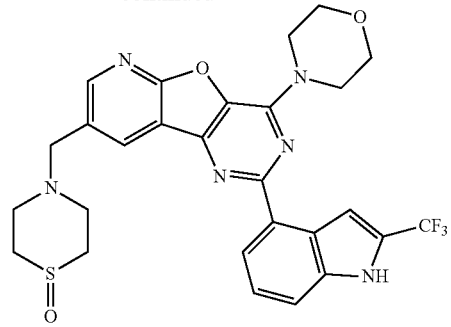

Example S

To a suspension of Intermediate 41 (68.4 mg, 0.146 mmol, 1.0 eq) in anhydrous CH$_2$Cl$_2$ (3 mL) was added 1-oxide thiomorpholine hydrochloride (45.6 mg, 0.293 mmol, 2.0 eq) and sodium acetate (24.0 mg, 0.293 mmol, 2.0 eq) and the resulting suspension was stirred at 42° C. for 6 h. After cooling to rt, NaBH(OAc)$_3$ (62.1 mg, 0.293 mmol, 2.0 eq) was added and the reaction mixture was stirred at rt for 16 h. Additional portions of sodium acetate (12.0 mg, 0.147 mmol, 1.0 eq), 1-oxide thiomorpholine hydrochloride (22.8 mg, 0.147 mmol, 1.0 eq) and NaBH(OAc)$_3$ (31.1 mg, 0.147 mmol, 1.0 eq) were added and the reaction was stirred at 40° C. for 18 h. Upon cooling to rt, the reaction was quenched with 1 M aqueous NaOH (5 mL) then poured into H$_2$O (15 mL) and extracted with CH$_2$Cl$_2$ (3×15 mL). The combined organic extracts were concentrated in vacuo and purified by silica gel chromatography using EtOAc/MeOH (1:0-13:1). The product was re-dissolved in CH$_2$Cl$_2$/MeOH (4:1, 10 mL) and swirled with MP-TMT resin (157 mg, 0.173 mmol) at rt overnight. The solution was filtered and the resin washed with CH$_2$Cl$_2$/MeOH (4:1, 100 mL). The filtrate was concentrated in vacuo and purified a second time by silica gel column chromatography with CH$_2$Cl$_2$/MeOH (1:0-12:1) to yield Example S as a white solid (37.6 mg, 45%).

$^1$H NMR (300 MHz, DMSO-d$_6$) $\delta_H$: 12.47 (s, 1H), 8.54-8.67 (m, 2H), 8.28 (dd, J=7.4, 0.8 Hz, 1H), 7.98 (s, 1H), 7.64 (d, J=8.1 Hz, 1H), 7.40-7.52 (m, 1H), 4.08-4.19 (m, 4H), 3.81-3.92 (m, 6H), 2.86-3.02 (m, 4H), 2.68-2.80 (m, 4H).

$^{19}$F NMR (282 MHz, DMSO-d$_6$) $\delta_F$: -58.8 (s, 3F).

MS (ES$^+$) 571.0 (100%, [M+H]$^+$).

Example T

4-{[4-(5-Chloro-1H-indol-4-yl)-6-(morpholin-4-yl)-8-oxa-3,5,10-triazatricyclo[7.4.0.0$^{2,7}$]trideca-1(9),2,4,6,10,12-hexaen-12-yl]methyl}-1λ$^4$-thiomorpholin-1-one

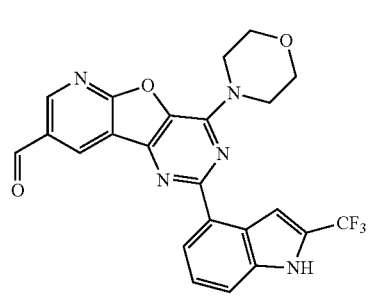

Intermediate 36

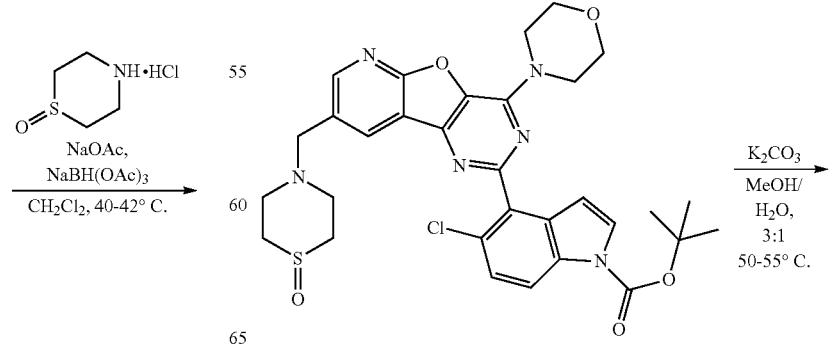

Intermediate 45

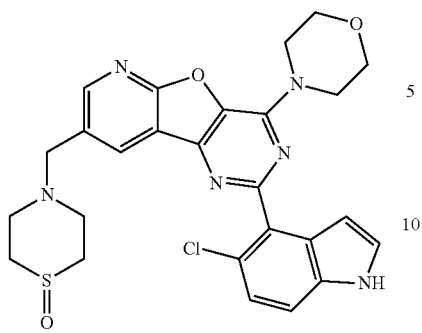

Example T

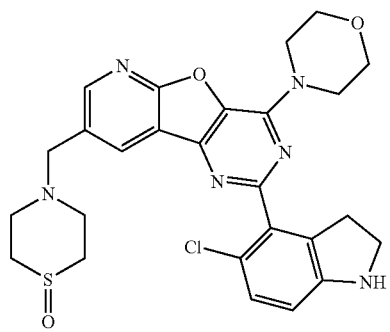

Example U

A suspension of Intermediate 45 (172 mg, 0.270 mmol, 1.0 eq) and potassium carbonate (112 mg, 0.810 mmol, 3.0 eq) in a mixture of MeOH (2.4 mL) and H$_2$O (0.8 mL) was stirred at 50° C. for 4 h. After cooling to rt, additional MeOH (1 mL), and potassium carbonate (37.3 mg, 0.270 mmol, 1.0 eq) were added and the reaction was stirred at 55° C. for 1 h. The mixture was concentrated in vacuo and purified by silica gel chromatography using CH$_2$Cl$_2$/MeOH (1:0-19:1) yielding Example T as a white solid (87.8 mg, 61%).

$^1$H NMR (300 MHz, DMSO-d$_6$) δ$_H$: 11.36 (br. s., 1H), 8.63 (d, J=1.9 Hz, 1H), 8.53 (d, J=2.1 Hz, 1H), 7.48 (d, J=8.7 Hz, 1H), 7.41 (t, J=2.6 Hz, 1H), 7.21 (d, J=8.5 Hz, 1H), 6.32 (br s, 1H), 3.97-4.14 (m, 4H), 3.74-3.89 (m, 6H), 2.83-3.00 (m, 4H), 2.64-2.80 (m, 4H).

MS (ES$^+$) 269.1 (100%, [M+2H]$^{2+}$), 537.2 (100%, [M+H]$^+$).

To a microwave vial containing a solution of Example T (29.8 mg, 0.0555 mmol, 1.0 eq) in trifluoroacetic acid (1 mL) was added triethylsilane (35.5 µL, 0.222 mmol, 4.0 eq) and the reaction was stirred at 50° C. for 30 min. Upon cooling to rt the mixture was diluted with H$_2$O (1 mL), poured into 1 M aqueous NaOH (20 mL) and extracted with CH$_2$Cl$_2$ (3×15 mL). The combined organic extracts were dried over MgSO$_4$, filtered and concentrated in vacuo. Purification twice by silica gel chromatography using CH$_2$Cl$_2$/MeOH (1:0-19:1) then EtOAc/CH$_2$Cl$_2$/MeOH (1:0:0-5:4:1) yielded Example U as an off-white solid (16.0 mg, 53%).

$^1$H NMR (300 MHz, DMSO-d$_6$) δ$_H$: 8.62 (d, J=2.1 Hz, 1H), 8.53 (d, J=2.1 Hz, 1H), 7.05 (d, J=8.3 Hz, 1H), 6.53 (d, J=8.3 Hz, 1H), 5.75 (s, 1H), 3.97-4.11 (m, 4H), 3.81 (d, J=4.1 Hz, 6H), 3.43 (t, J=8.4 Hz, 2H), 2.81-2.99 (m, 6H), 2.64-2.79 (m, 4H).

MS (ES$^+$) 270.2 (100%, [M+2H]$^{2+}$), 539.2 (30%, [M+H]$^+$), 561.2 (10%, [M+Na]$^+$).

Example U

4-{[4-(5-Chloro-2,3-dihydro-1H-indol-4-yl)-6-(morpholin-4-yl)-8-oxa-3,5,10-triazatricyclo[7.4.0.0$^{2,7}$]trideca-1(9),2,4,6,10,12-hexaen-12-yl]methyl}-1λ$^4$-thiomorpholin-1-one Example V 4-{[4-(5-Methyl-2,3-dihydro-1H-indol-4-yl)-6-(morpholin-4-yl)-8-oxa-3,5,10-triazatricyclo[7.4.0.0$^{2,7}$]trideca-1(9),2,4,6,10,12-hexaen-12-yl]methyl}-1λ$^4$-thiomorpholin-1-one

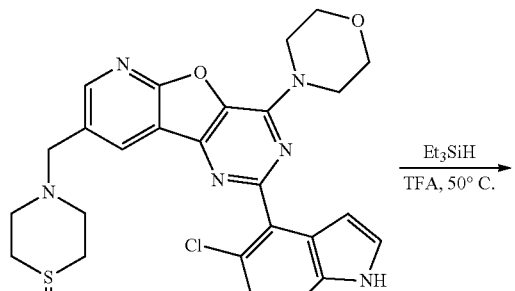

Example T

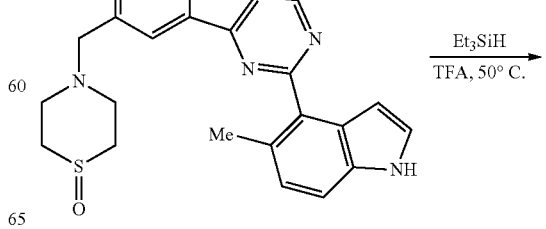

Example P

-continued

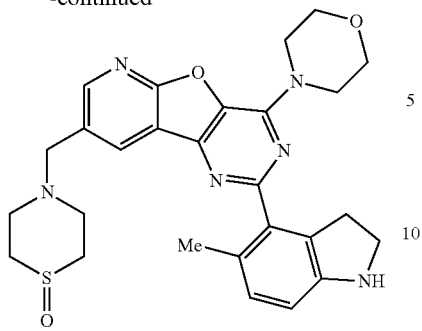

Example V

To a microwave vial containing a solution of Example P (32.5 mg, 0.0629 mmol, 1.0 eq) in trifluoroacetic acid (1 mL) was added triethylsilane (40.2 μL, 0.252 mmol, 4.0 eq) and the reaction was stirred at 50° C. for 2 h. Upon cooling to rt, 1 M aqueous NaOH (2 mL) was added before the mixture was poured into additional 1 M aqueous NaOH (20 mL) and extracted with CH$_2$Cl$_2$ (3×20 mL). The combined organic extracts were dried over MgSO$_4$, filtered and concentrated in vacuo. Purification by silica gel chromatography using EtOAc/CH$_2$Cl$_2$/MeOH (1:0:0-6:4:1) yielded Example V as an off-white solid (24.1 mg, 74%).

$^1$H NMR (300 MHz, DMSO-d$_6$) δ$_H$: 8.61 (d, J=2.1 Hz, 1H), 8.51 (d, J=2.1 Hz, 1H), 6.84 (d, J=8.1 Hz, 1H), 6.48 (d, J=7.9 Hz, 1H), 5.37 (br s, 1H), 4.02 (d, J=4.5 Hz, 4H), 3.81 (d, J=3.8 Hz, 6H), 3.33-3.43 (m, 2H), 2.79-3.01 (m, 6H), 2.61-2.79 (m, 4H), 2.17 (s, 3H).

MS (ES$^+$) 260.2 (50%, [M+2H]$^{2+}$), 519.2 (100%, [M+H]$^+$).

Example W

4-[6-(morpholin-4-yl)-12-[(1-oxo-1λ$^4$-thiomorpholin-4-yl)methyl]-8-oxa-3,5,10-triazatricyclo[7.4.0.0$^2$,$^7$]trideca-1(9),2,4,6,10,12-hexaen-4-yl]-1H-indole-5-carbonitrile -continued

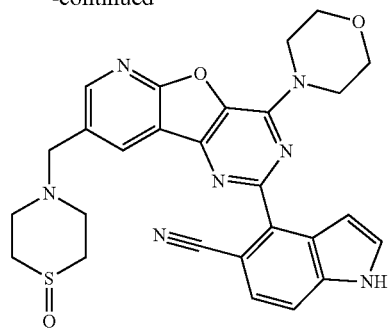

Example W

To a microwave vial containing Intermediate 8 (71.8 mg, 0.170 mmol, 1.0 eq), Intermediate 48 (98.1 mg, 0.340 mmol, 2.0 eq), sodium carbonate (36.0 mg, 0.340 mmol, 2.0 eq) and PdCl$_2$(PPh$_3$)$_2$ (23.9 mg, 0.0340 mmol, 20 mol %) was added 1,4-dioxane (0.7 mL) and H$_2$O (0.2 mL). The suspension was stirred at 90° C. for 16 h then cooled to rt and concentrated in vacuo. The product was re-dissolved in CH$_2$Cl$_2$/MeOH (1:1, 20 mL) and swirled with MP-TMT resin (200 mg, 0.220 mmol, 6 eq wrt Pd) at rt for 4 h, before the solution was filtered and the resin washed with CH$_2$Cl$_2$/MeOH (4:1, 50 mL). The filtrate was concentrated in vacuo and purified once by silica gel column chromatography using EtOAc/MeOH (1:0-4:1) then CH$_2$Cl$_2$/MeOH (1:0-9:1). The product was swirled a second time with MP-TMT resin (120 mg, 0.132 mmol, 4 eq wrt Pd) in CH$_2$Cl$_2$/MeOH (4:1, 15 mL) at rt overnight. The solution was filtered, the resin washed with CH$_2$Cl$_2$/MeOH (4:1, 50 mL) and the filtrate concentrated in vacuo to yield Example W as an off-white solid (62.2 mg, 69%).

$^1$H NMR (300 MHz, DMSO-d$_6$) δ$_H$: 11.78 (br. s., 1H), 8.50-8.78 (m, 2H), 7.61-7.71 (m, 2H), 7.55-7.60 (m, 1H), 7.14-7.22 (m, 1H), 4.12-4.22 (m, 4H), 3.77-4.06 (m, 6H), 2.63-3.08 (m, 8H).

MS (ES$^+$) 264.7 (60%, [M+2H]$^{2+}$), 528.2 (100%, [M+H]$^+$).

Example X

4-[6-(morpholin-4-yl)-12-[(1-oxo-1λ$^4$-thiomorpholin-4-yl)methyl]-8-oxa-3,5,10-triazatricyclo[7.4.0.0$^2$,$^7$]trideca-1(13),2(7),3,5,9,11-hexaen-4-yl]-1H-indole-5-carboxylic acid

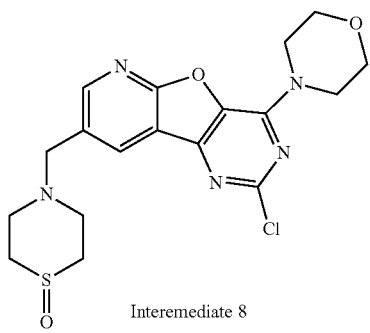

Interemediate 8

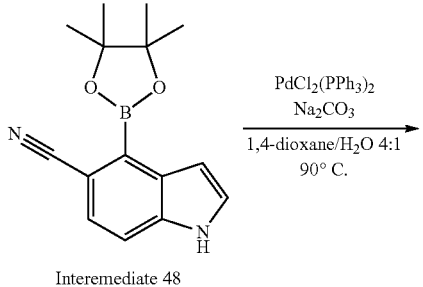

Interemediate 48

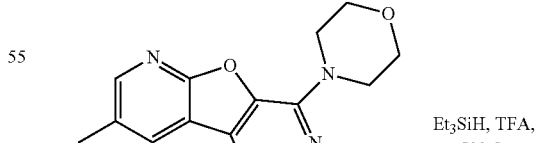
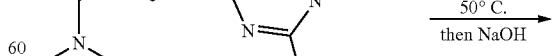
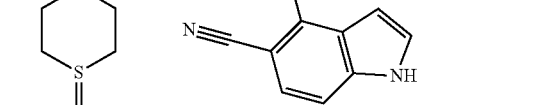

Example W

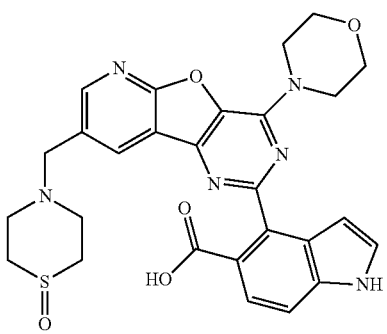

Example X

To a microwave vial containing a solution of Example W (29.7 mg, 0.0563 mmol, 1.0 eq) in trifluoroacetic acid (1 mL) was added triethylsilane (18.0 µL, 0.113 mmol, 2.0 eq) and the reaction was stirred at 50° C. for 1.5 h. Upon cooling to rt, additional triethylsilane (18.0 µL, 0.113 mmol, 2.0 eq) was added and the reaction mixture was stirred at 50° C. for 16 h. After cooling slightly to 40° C., 1 M aqueous NaOH (3 mL) was added before the mixture was poured into additional 1 M aqueous NaOH (20 mL) and extracted with $CH_2Cl_2$ (3×20 mL). The combined organic extracts were dried over $MgSO_4$, filtered and concentrated in vacuo. LCMS analysis indicated the presence of Example X in the aqueous phase, which was then concentrated in vacuo and recombined with the organic extracts. Purification by reverse phase silica gel chromatography using $H_2O$/MeCN (1:0-4:1) yielded Example X as an off-white solid (6.52 mg, 21%).

$^1$H NMR (300 MHz, $D_2O$) $\delta_H$: 8.32 (d, J=1.9 Hz, 1H), 8.17 (d, J=1.9 Hz, 1H), 7.56-7.69 (m, 2H), 7.29-7.46 (m, 2H), 4.03-4.14 (m, 4H), 3.89-3.98 (m, 4H), 2.99 (s, 2H), 2.55-2.76 (m, 6H), 2.30-2.48 (m, 2H).

MS (ES$^+$) 274.2 (60%, [M+2H]$^{2+}$), 547.1 (100%, [M+H]$^+$).

Example Y

4-{[6-(Morpholin-4-yl)-4-[5-(propan-2-yloxy)-1H-indol-4-yl]-8-oxa-3,5,10-triazatricyclo[7.4.0.0$^{2,7}$]trideca-1(9),2,4,6,10,12-hexaen-12-yl]methyl}-1λ$^4$-thiomorpholin-1-one

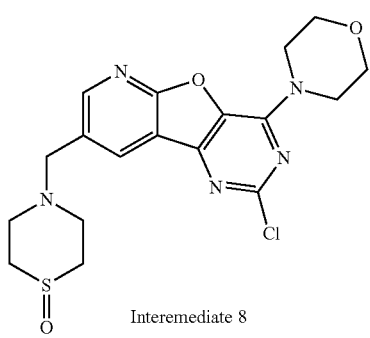

Interemediate 8

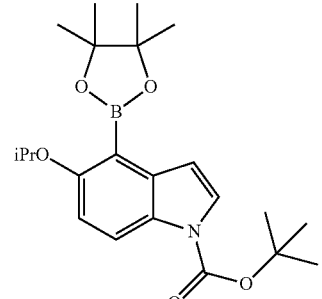

Interemediate 52

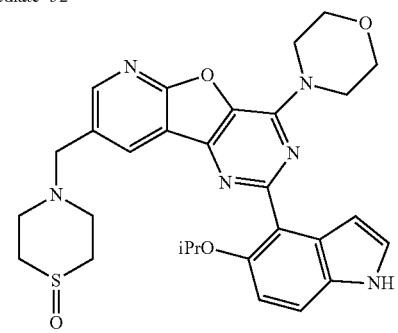

Example Y

To a microwave vial containing Intermediate 8 (52.7 mg, 0.125 mmol, 1.0 eq), Intermediate 52 (50 mg, 0.125 mmol, 1.0 eq), sodium carbonate (13.2 mg, 0.125 mmol, 1.0 eq) and $PdCl_2(PPh_3)_2$ (17.5 mg, 0.0249 mmol, 20 mol %) was added 1,4-dioxane (0.5 mL) and $H_2O$ (0.1 mL). The suspension was stirred at 90° C. for 16 h then cooled to rt and recharged with Intermediate 52 (50 mg, 0.125 mmol, 1.0 eq), sodium carbonate (13.2 mg, 0.125 mmol, 1.0 eq) and $PdCl_2(PPh_3)_2$ (8.7 mg, 0.0125 mmol, 10 mol %). After stirring at 90° C. for a further 6.5 h, the reaction mixture was cooled to rt, $H_2O$ (5 mL) was added and the resulting mixture was extracted with $CH_2Cl_2$ (3×5 mL), dried over $MgSO_4$, filtered, concentrated in vacuo and purified by silica gel chromatography using $CH_2Cl_2$/MeOH (1:0-24:1). The product was then dissolved in MeOH (15 mL) and $H_2O$ (5 mL). Potassium carbonate (51.8 mg, 0.375 mmol, 3.0 eq) was added and the reaction mixture was stirred at 50° C. for 16 h then cooled to rt and concentrated in vacuo. The residue was re-dissolved in $CH_2Cl_2$ (15 mL), $H_2O$ (10 mL) was added and the mixture was extracted with $CH_2Cl_2$ (2×15 mL). The combined organic extracts were washed with brine (30 mL), concentrated in vacuo to a volume of 15 mL and swirled with MP-TMT resin (200 mg, 0.220 mmol, 9 eq wrt Pd) at rt for 3 h. The solution was filtered, the resin washed with $CH_2Cl_2$/MeOH (4:1, 50 mL) and the filtrate concentrated in vacuo. Purification by silica gel column chromatography using $CH_2Cl_2$/MeOH (1:0-24:1) yielded Example Y as a yellow solid (28.6 mg, 41%).

$^1$H NMR (300 MHz, DMSO-d$_6$) $\delta_H$: 11.02 (br s, 1H), 8.61 (d, J=1.9 Hz, 1H), 8.50 (d, J=1.9 Hz, 1H), 7.39 (d, J=8.7 Hz, 1H), 7.30 (t, J=2.6 Hz, 1H), 6.93 (d, J=8.7 Hz, 1H), 6.24-6.39 (m, 1H), 4.31 (spt, J=6.1 Hz, 1H), 3.96-4.13 (m, 4H), 3.67-3.91 (m, 6H), 2.81-3.02 (m, 4H), 2.61-2.79 (m, 4H), 1.13 (d, J=6.2 Hz, 6H).

MS (ES$^+$) 281.2 (100%, [M+2H]$^{2+}$), 561.2 (80%, [M+H]$^+$).

Example Z

4-{[6-(Morpholin-4-yl)-4-[5-(trifluoromethoxy)-1H-indol-4-yl]-8-oxa-3,5,10-triazatricyclo[7.4.0.0$^{2,7}$]trideca-1(9),2,4,6,10,12-hexaen-12-yl]methyl}-1$\lambda^4$-thiomorpholin-1-one

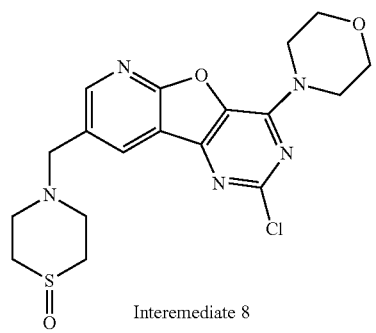

Interemediate 8

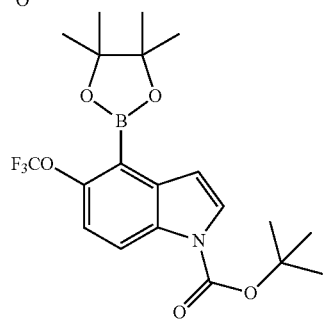

Interemediate 54

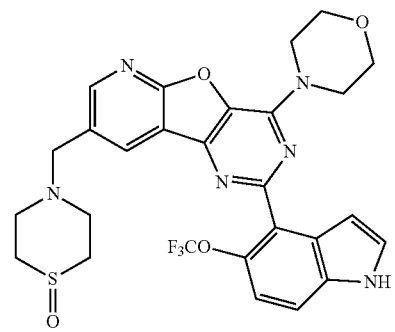

Example Z

To a microwave vial containing Intermediate 8 (29.6 mg, 0.0702 mmol, 1.0 eq), sodium carbonate (7.4 mg, 0.0702 mmol, 1.0 eq) and PdCl$_2$(PPh$_3$)$_2$ (9.8 mg, 0.0140 mmol, 20 mol %) was added a solution of Intermediate 54 (30.0 mg, 0.0702 mmol, 1.0 eq) in 1,4-dioxane (0.4 mL), followed by H$_2$O (0.1 mL). The suspension was stirred at 90° C. for 2.5 h then cooled to rt, concentrated in vacuo and purified by silica gel chromatography using EtOAc/MeOH (1:0-6:1). The product was dissolved in CH$_2$Cl$_2$/MeOH (10mL) and swirled with MP-TMT resin (100 mg, 0.110 mmol, 8 eq wrt Pd) at rt for 18 h. The solution was filtered, the resin washed with CH$_2$Cl$_2$/MeOH (4:1, 50 mL) and the filtrate concentrated in vacuo. The product (24.7 mg, 0.0359 mmol, 1.0 eq) was dissolved in MeOH (4.5 mL) and H$_2$O (1.5 mL) then potassium carbonate (15.0 mg, 0.108 mmol, 3.0 eq) was added and the reaction mixture was stirred at 55° C. for 2 h. After cooling to rt, the solution was concentrated in vacuo and redissolved in CH$_2$Cl$_2$ (10 mL). H$_2$O (10 mL) was added and the mixture was extracted with CH$_2$Cl$_2$ (2×15 mL). The combined organic extracts were dried over MgSO$_4$, filtered and concentrated in vacuo. Purification by silica gel column chromatography using CH$_2$Cl$_2$/MeOH (1:0-13:1) yielded Example Z as a white solid (16.1 mg, 39%).

$^1$H NMR (300 MHz, DMSO-d$_6$) $\delta_H$: 11.46 (br s, 1H), 8.63 (d, J=2.1 Hz, 1H), 8.52 (d, J=2.1 Hz, 1H), 7.57 (dd, J=8.8, 0.7 Hz, 1H), 7.51 (t, J=2.7 Hz, 1H), 7.17 (dd, J=8.8, 1.0 Hz, 1H), 6.64 (t, J=2.0 Hz, 1H), 3.96-4.16 (m, 4H), 3.72-3.87 (m, 6H), 2.82-3.00 (m, 4H), 2.64-2.79 (m, 4H). $^{19}$F NMR (282 MHz, DMSO-d$_6$) $\delta_F$: −55.56 (s, 3F)

MS (ES$^+$) 294.2 (100%, [M+2H]$^{2+}$), 587.1 (70%, [M+H]$^+$).

Example AA

4-{[4-(1H-indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}-1$\lambda^6$,4-thiazepane-1,1-dione

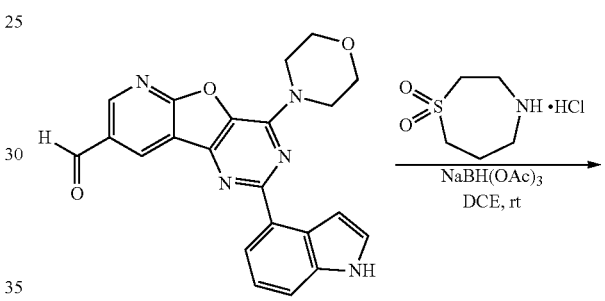

Intermediate 7

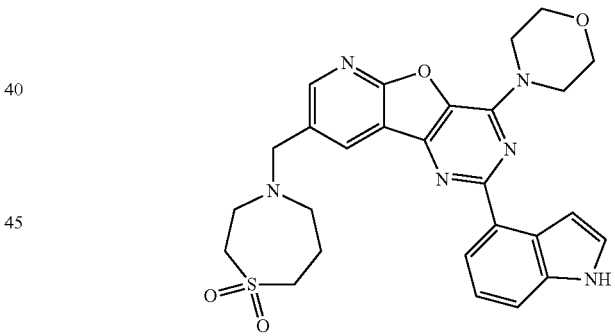

Example AA

To Intermediate 7 (25 mg, 0.06 mmol) in anhydrous DCE (4 mL) were added 1$\lambda$☐,4-thiazepane-1,1-dione hydrochloride (46 mg, 0.25 mmol, 4 eq) and NaOAc (20.5 mg, 0.25 mmol, 4 eq) under Ar(g). The reaction mixture was stirred at rt overnight, then NaBH(OAc)$_3$ (25 mg, 0.12 mmol, 2 eq) was added and the reaction mixture was further stirred for 7 h at rt. It was then quenched with saturated Na$_2$CO$_3$ solution (1 mL) and stirred at rt overnight. The layers were separated using a phase separator and the organics were Pd-scavenged with MP-TMT in CH$_2$Cl$_2$/MeOH (1:1, 10 mL) for 2 h. After filtration, the solvent was removed in vacuo and the residue was purified by preparative LCMS to yield Example AA as a white solid (1.58 mg, 5%).

$^1$H NMR (400 MHz, DMSO-d$_6$) $\delta_H$: 11.28 (br s, 1H), 8.66 (s, 2H), 8.18 (d, J=7.3 Hz, 1H), 7.46-7.58 (m, 3H), 7.23 (t, J=7.8 Hz, 1H), 4.10-4.18 (m, 4H), 3.98 (s, 2H), 3.83-3.90 (m, 4H), 3.23-3.31 (m, 4H), 2.94-3.01 (m, 2H), 2.89 (t, J=6.2 Hz, 2H), 1.91-1.99 (m, 2H).

MS (ES+) 533.5 (100%, [M+H]+).

Example AB

6-{[4-(1H-Indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}-2λ$^6$-thia-6-azaspiro[3.3]heptane-2,2-dione

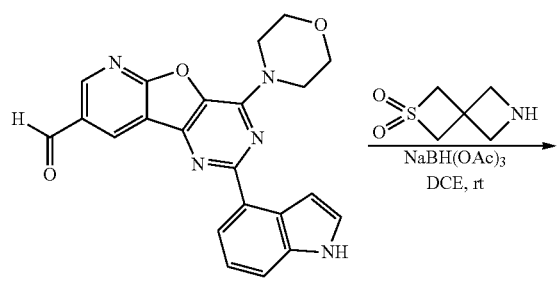

Intermediate 7

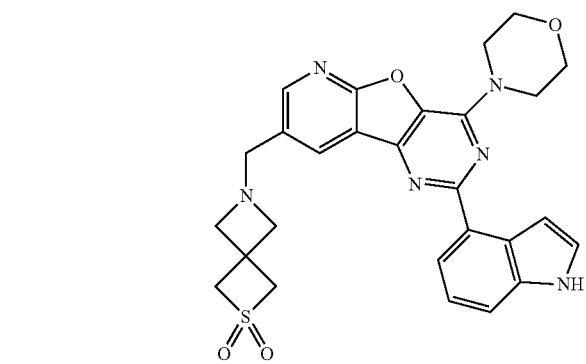

Example AB

To Intermediate 7 (25 mg, 0.06 mmol) in anhydrous DCE (4 mL) was added 2λ□-thia-6-azaspiro[3.3]heptane-2,2-dione (19 mg, 0.12 mmol, 2 eq) under Ar(g). The reaction mixture was stirred at rt overnight, then NaBH(OAc)$_3$ (25 mg, 0.12 mmol, 2 eq) was added and the reaction mixture was further stirred for 7 h at rt. It was then quenched with saturated Na$_2$CO$_3$ solution (1 mL) and stirred at rt overnight. The layers were separated using a phase separator and the organics were Pd-scavenged with MP-TMT in CH$_2$Cl$_2$/MeOH (1:1, 10 mL) for 2 h. After filtration, the solvent was removed in vacuo and the residue was purified by preparative LCMS to yield Example AB as a white solid (1.49 mg, 5%).

$^1$H NMR (400 MHz, DMSO-d$_6$) δ$_H$: 11.28 (br s, 1H), 8.52-8.60 (m, 2H), 8.18 (d, J=7.3 Hz, 1H), 7.47-7.57 (m, 3H), 7.23 (t, J=7.8 Hz, 1H), 4.36 (m, 4H), 4.10-4.17 (m, 4H), 3.78-3.91 (m, 6H), 3.44 (m, 4H).

MS (ES+) 531.5 (100%, [M+H]+).

Example AC 4-(1H-Indol-4-yl)-6-(morpholin-4-yl)-12-[(1,3-thiazolidin-3-yl)methyl]-8-oxa-3,5,10-triazatricyclo[7.4.0.0$^{2,7}$]trideca-1(13),2(7),3,5,9,11-hexaene

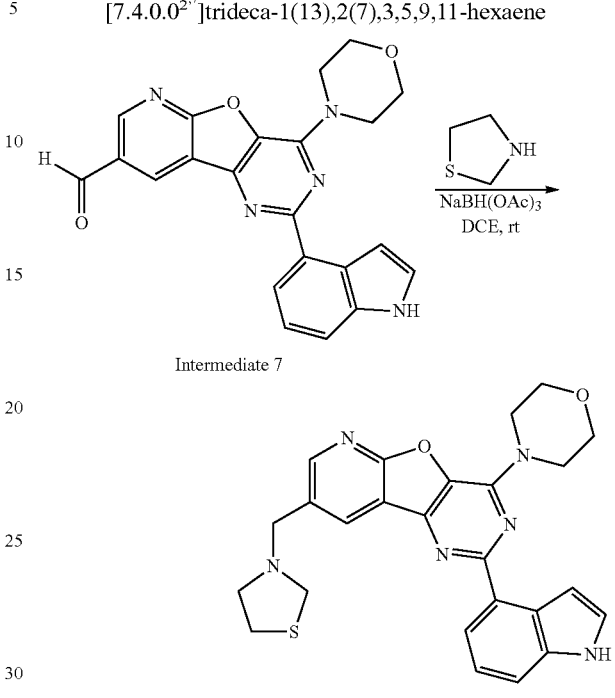

To Intermediate 7 (25 mg, 0.06 mmol) in anhydrous DCE (4 mL) was added 1,3-thiazolidine (22 mg, 0.24 mmol, 4 eq) under Ar(g). The reaction mixture was stirred at rt overnight, then NaBH(OAc)$_3$ (25 mg, 0.12 mmol, 2 eq) was added and the reaction mixture was further stirred for 7 h at rt. It was then quenched with saturated Na$_2$CO$_3$ solution (1 mL) and stirred at rt overnight. The layers were separated using a phase separator and the organics were Pd-scavenged with MP-TMT in CH$_2$Cl$_2$/MeOH (1:1, 10 mL) for 2h. After filtration, the solvent was removed in vacuo and the residue was purified by preparative LCMS to yield Example AC as a white solid (4.69 mg, 17%).

MS (ES+) 473.2 (100%, [M+H]+).

Example AD

{[4-(1H-Indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}(2-methanesulfonylethyl)amine

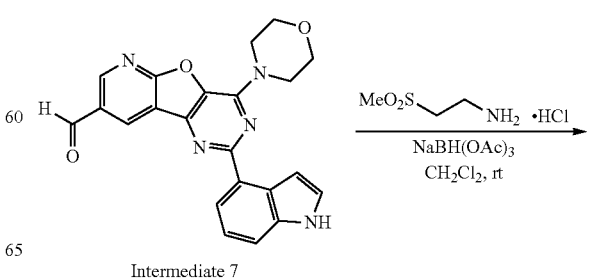

Intermediate 7

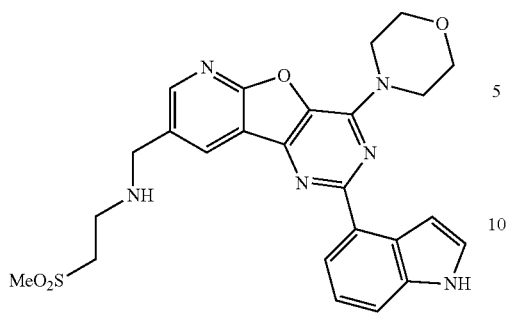

Example AD

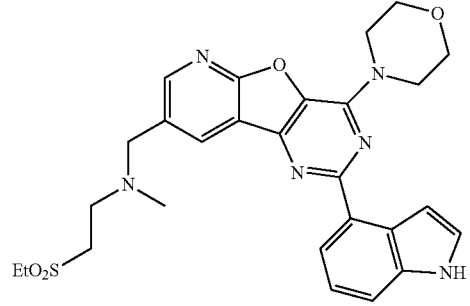

Example AE

To a suspension of MP-TMT Pd-scavenged Intermediate 7 (30 mg, 0.075 mmol) in CH$_2$Cl$_2$ (4 mL) at rt were added [2-(ethanesulfonyl)ethyl](methyl)amine (32 uL, 0.23 mmol, 3 eq) and NaBH(OAc)$_3$ (49 mg, 0.23 mmol, 3 eq) under Ar(g). The mixture was stirred at rt overnight. The mixture was then washed with 0.5N NaOH (2 mL). The layers were separated using a phase separator, the aqueous layer was extracted CH$_2$Cl$_2$ (2×5 mL) and the organics were concentrated in vacuo. The residue was purified by preparative LCMS to give Example AE as a white solid (21.5 mg, 54%).

$^1$H NMR (400 MHz, DMSO-d$_6$) δ$_H$: 11.29 (br s, 1H), 8.49-8.70 (m, 2H), 8.18 (d, J=7.3 Hz, 1H), 7.43-7.61 (m, 3H), 7.22 (t, J=7.7 Hz, 1H), 4.13 (m, 4H), 3.81-3.95 (m, 4H), 3.78 (s, 2H), 3.39 (t, J=6.8 Hz, 2H), 3.17 (q, J=7.5 Hz, 2H), 2.87 (t, J=6.8 Hz, 2H), 2.23 (s, 3H), 1.25 (t, J=7.5 Hz, 3H).

MS (ES$^+$) 534.9 (100%, [M+H]$^+$).

To a suspension of MP-TMT Pd-scavenged Intermediate 7 (30 mg, 0.075 mmol) in CH$_2$Cl$_2$ (2 mL) and MeOH (2 mL) at rt were added 2-methanesulfonylethan-1-amine (23 uL, 0.23 mmol, 3 eq), Et$_3$N (35 uL, 0.25 mmol, 3.3 eq) and Ti(OiPr)$_4$ (44 uL, 0.15 mmol, 2 eq) under Ar(g). The reaction mixture was heated up at 50° C. overnight. Once cooled to 0° C., NaBH(OAc)$_3$ (32 mg, 0.15 mmol, 2 eq) was added and the reaction mixture was allowed to warm to rt. It was then washed with 1N NaOH (3 mL). The layers were separated using a phase separator, the aqueous layer was extracted CH$_2$Cl$_2$ (2×5 mL) and the organics were concentrated in vacuo. The residue was purified by preparative LCMS to give Example AD as a white solid (9 mg, 24%).

$^1$H NMR (400 MHz, DMSO-d$_6$) δ$_H$: 11.29 (br s, 1H), 8.57-8.74 (m, 2H), 8.18 (d, J=7.3 Hz, 1H), 7.43-7.62 (m, 3H), 7.23 (t, J=7.7 Hz, 1H), 4.06-4.22 (m, 5H), 3.97 (br s, 2H), 3.80-3.90 (m, 4H), 3.25-3.31 (m, 1H), 3.16 (d, J=5.3 Hz, 1H), 3.04 (s, 3H), 2.95 (t, J=6.6 Hz, 2H).

MS (ES$^+$) 507.1 (100%, [M+H]$^+$).

Example AE

[2-(ethanesulfonypethyl]({[4-(1H-indol-4-yl)-6-(morpholin-4-yl)-8-oxa-3,5,10-triazatricyclo [7.4.0.0$^{2,7}$]trideca-1(13),2(7),3,5,9,11-hexaen-12-yl]methyl})methylamine Example AF 4-(1H-indol-4-yl)-6-(morpholin-4-yl)-12-[(thiomorpholin-4-yl)methyl]-8-oxa-3,5,10-triazatricyclo [7.4.0.0$^{2,7}$]trideca-1(13),2(7),3,5,9,11-hexaene

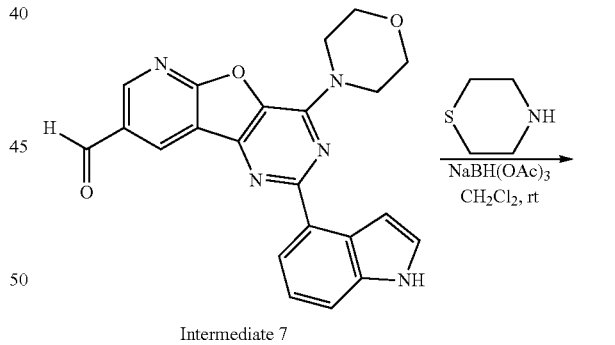

Intermediate 7

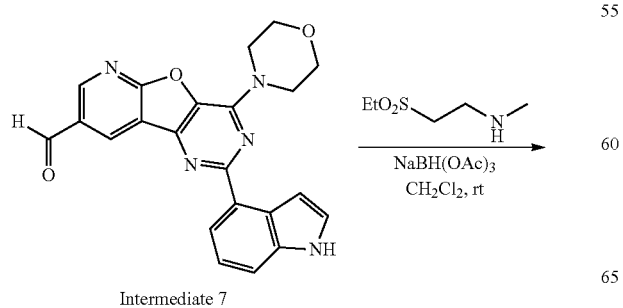

Intermediate 7

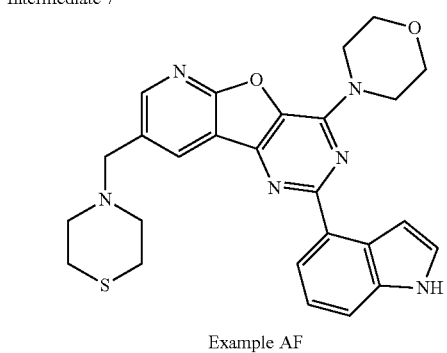

Example AF

To a suspension of MP-TMT Pd-scavenged Intermediate 7 (30 mg, 0.075 mmol) in CH$_2$Cl$_2$ (4 mL) at rt was added thiomorpholine (23 uL, 0.23 mmol, 3 eq) under Ar(g) and NaBH(OAc)$_3$ (49 mg, 0.23 mmol, 3 eq). The mixture was stirred at rt overnight. The mixture was then washed with 0.5N NaOH (2 mL). The layers were separated using a phase separator, the aqueous layer was extracted CH$_2$Cl$_2$ (2×5 mL) and the organics were concentrated in vacuo. The residue was purified by preparative LCMS to give Example AF as a white solid (5.1 mg, 14%).

$^1$H NMR (400 MHz, DMSO-d$_6$) δ$_H$: 11.30 (br s, 1H), 8.53-8.64 (m, 2H), 8.18 (d, J=7.6 Hz, 1H), 7.46-7.60 (m, 3H), 7.23 (t, J=7.8 Hz, 1H), 4.07-4.20 (m, 4H), 3.82-3.92 (m, 4H), 3.77 (s, 2H), 2.59-2.77 (m, 8H).

MS (ES$^+$) 486.9 (100%, [M+H]$^+$).

Example AG

4-{[4-(2-methyl-1H-indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}-1λ$^4$-thiomorpholin-1-one

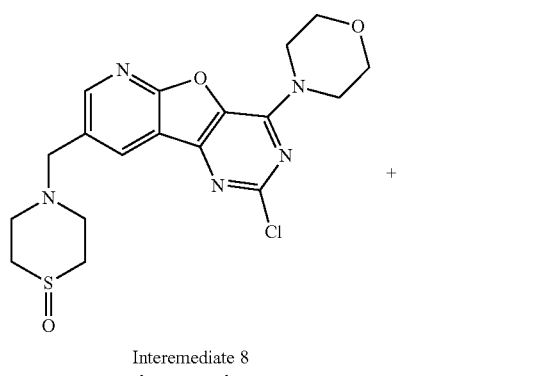

Example AG

To Intermediate 8 (77 mg, 0.18 mmol, 1 eq) was added Intermediate 55 (94 mg, 0.36 mmol, 2 eq), PdCl$_2$(PPh$_3$)$_2$ (26 mg, 0.037 mmol, 0.2 eq) and sodium carbonate (58 mg, 0.55 mmol, 3 eq) in dioxane (4 mL)/water (1 mL). The reaction mixture was heated in the microwave at 90° C. for 2 h until completion. It was then cooled down to rt, partitioned with water (15 mL) and extracted with EtOAc (3×15 mL). The combined organics were dried over MgSO$_4$, filtered and the solvent was removed in vacuo. The residue was dissolved in CH$_2$Cl$_2$/MeOH (1:1, 10 mL) and swirled with MP-TMT resin (~250 mg, 1.1 mmol/g, 5 eq) overnight. Upon filtration, the solvent was removed in vacuo. Purification by silica gel column chromatography with EtOAc/MeOH (1:0-4:1) yielded Example AG as a pale yellow solid (72 mg, 76%).

$^1$H NMR (300 MHz, DMSO-d$_6$) δ$_H$: 11.08 (s, 1H), 8.57-8.66 (m, 2H), 8.11 (dd, J=7.5, 0.8 Hz, 1H), 7.40 (d, J=7.9 Hz, 1H), 7.21 (s, 1H), 7.12 (t, J=7.7 Hz, 1H), 4.07-4.19 (m, 4H), 3.80-3.92 (m, 6H), 2.85-3.04 (m, 4H), 2.66-2.83 (m, 4H), 2.47-2.48 (m, 3H).

MS (ES$^+$) 517.2 (100%, [M+H]$^+$).

Example AH

4-{[4-(1H-indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}-1λ$^4$-thiomorpholin-1-one

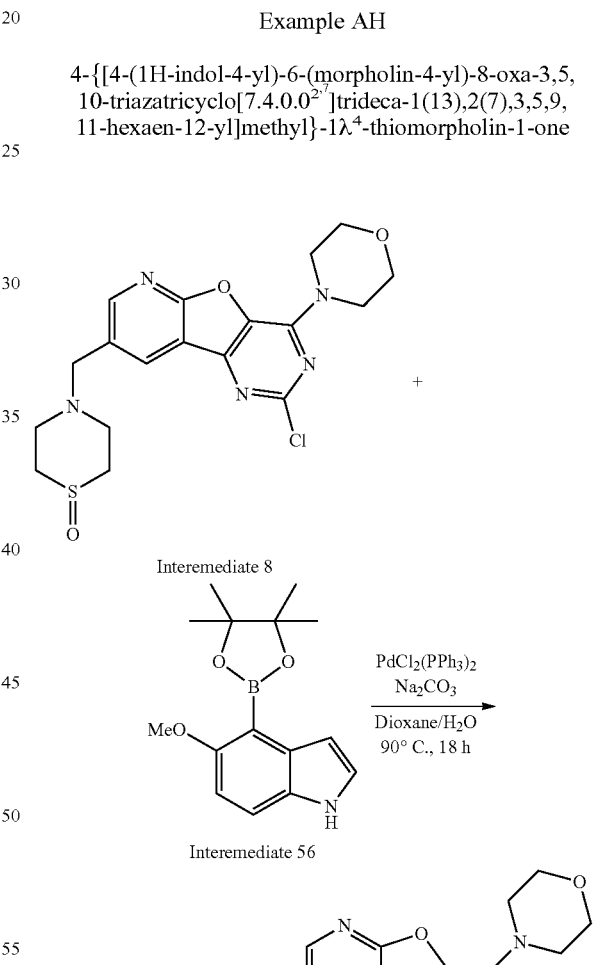

Example AH

To Intermediate 8 (75 mg, 0.18 mmol, 1 eq) was added Intermediate 56 (97 mg, 0.36 mmol, 2 eq), PdCl$_2$(PPh$_3$)$_2$ (25 mg, 0.036 mmol, 0.2 eq) and sodium carbonate (57 mg, 0.53 mmol, 3 eq) in dioxane (3 mL)/water (0.7 mL). The reaction mixture was heated at 90° C. for 18 h until completion. It was then cooled down to rt, partitioned with water (15 mL) and extracted with EtOAc (3×15 mL). The combined organics were dried over MgSO$_4$, filtered and the solvent was removed in vacuo. The residue was dissolved in CH$_2$Cl$_2$/MeOH (1:1, 10 mL) and swirled with MP-TMT resin (-250 mg, 1.1 mmol/g, 5 eq) overnight. Upon filtration, the solvent was removed in vacuo. Purification by silica gel column chromatography with EtOAc/MeOH (1:0-4:1) yielded Product AH as a pale brown solid (72 mg, 76%).

$^1$H NMR (300 MHz, DMSO-d$_6$) δ$_H$: 11.00 (br s, 1H), 8.61 (d, J=2.1 Hz, 1H), 8.51 (d, J=1.9 Hz, 1H), 7.42 (d, J=8.7 Hz, 1H), 7.30 (t, J=2.6 Hz, 1H), 7.00 (d, J=8.7 Hz, 1H), 6.23-6.29 (m, 1H), 3.98-4.09 (m, 4H), 3.78-3.85 (m, 6H), 3.77 (s, 3H), 2.81-3.01 (m, 4H), 2.62-2.80 (m, 4H).

MS (ES$^+$) 533.2 (100%, [M+H]$^+$).

Example AI

4-{[4-(5-Methoxy-2,3-dihydro-1H-indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}-1λ$^4$-thiomorpholin-1-one

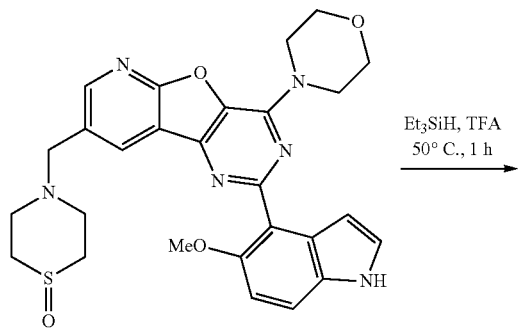

Example AH

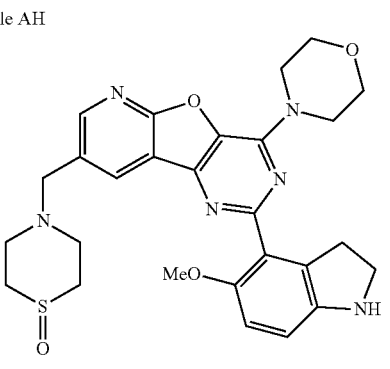

Example AI

To a solution of Example AH (20.3 mg, 0.038 mmol, 1 eq) in TFA (1 mL) was added Et$_3$SiH (24 uL, 0.15 mmol, 4 eq) at 0° C. under Ar(g). The reaction mixture was then heated up to 50° C. for 1 h. Once cooled down, it was quenched with 1N NaOH (5 mL) then partitioned between H$_2$O (5 mL) and EtOAc (3×5 mL). The combined organics were dried over MgSO$_4$, filtered and the solvent was removed in vacuo.

Purification by silica gel column chromatography with EtOAc/MeOH (1:0-4:1) then CH$_2$Cl$_2$/MeOH (1:0-4:1 +NH$_3$ in MeOH) yielded Example AI as a pale yellow solid (13.5 mg, 66%).

$^1$H NMR (300 MHz, DMSO-d$_6$) δ$_H$: 8.60 (d, J=2.1 Hz, 1H), 8.52 (d, J=2.1 Hz, 1H), 6.70 (d, J=8.5 Hz, 1H), 6.52 (d, J=8.5 Hz, 1H), 5.23 (br s, 1H), 3.95-4.07 (m, 4H), 3.73-3.85 (m, 6H), 3.61 (s, 3H), 3.33-3.40 (m, 2H), 2.82-3.01 (m, 4H), 2.64-2.82 (m, 6H).

MS (ES$^+$) 535.2 (100%, [M+H]$^+$).

Example AJ

4-{[4-(3-fluoro-1H-indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}-1λ$^4$-thiomorpholin-1-one

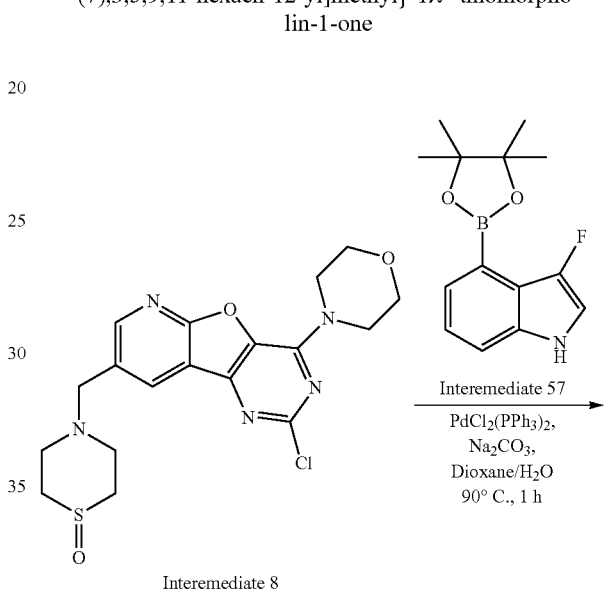

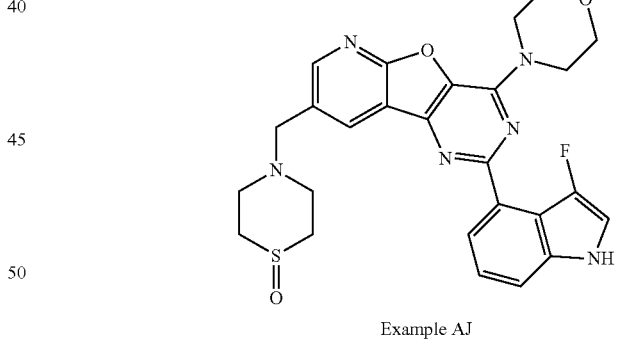

Example AJ

To Intermediate 8 (73 mg, 0.17 mmol, 1 eq) was added Intermediate 57 (90 mg, 0.35 mmol, 2 eq), PdCl$_2$(PPh$_3$)$_2$ (24 mg, 35 μmol, 0.2 eq) and sodium carbonate (37 mg, 0.35 mmol, 2 eq), followed by 1,4-dioxane-water (4:1, 1.7 mL). The reaction mixture was heated to 95° C. for 2 hr. It was then cooled to rt and partitioned between CH$_2$Cl$_2$ (20 mL) and aqueous sodium chloride solution (12.5% w/w, 20 mL). The aqueous phase was re-extracted with CH$_2$Cl$_2$ (3×5 mL) and the combined organics were dried over MgSO$_4$. The drying agent was removed by filtration and the filtrate was Pd-scavenged with MP-TMT resin (~156 mg, 1.1 mmol/g, 1 eq) overnight. The resin was removed by filtration and the filtrate was concentrated in vacuo. The residue was purified by silica gel column chromatography with EtOAc/MeOH (1:0-5:1) to afford Example AJ as a pale yellow-grey solid (50 mg, 56%).

$^1$H NMR (300 MHz, DMSO-d$_6$) $\delta_H$: 11.07 (br s, 1H), 8.61 (d, J=2.1 Hz, 1H), 8.56 (d, J=2.1 Hz, 1H), 7.68 (dd, J=7.3, 0.8 Hz, 1H), 7.49 (dd, J=8.1, 1.7 Hz, 1H), 7.42 (t, J=2.6 Hz, 1H), 7.25 (t, J=7.8 Hz, 1H), 4.05-4.17 (m, 4H), 3.83 (br. s., 6H), 2.66-3.01 (m, 8H). $^{19}$F NMR (282 MHz, DMSO-d$_6$) $\delta_F$: −163.3 (m, 1H).

MS (ES$^+$) 521.0 (100%, [M+H]$^+$).

Example AK

4-{[4-(1H-Indol-4-yl)-6-(morpholin-4-yl)-8-thia-3,5,10-triazatricyclo[7.4.0.0$^{2,7}$]trideca-1(9),2,4,6,10,12-hexaen-12-yl]methyl}-1$\lambda^4$-thiomorpholin-1-one

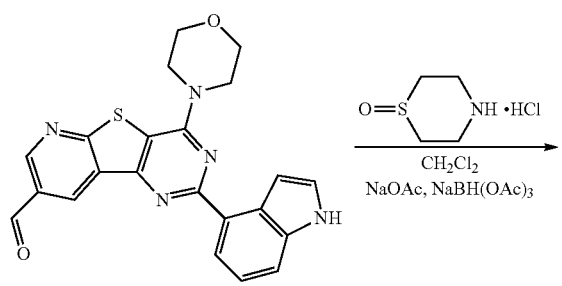

Intermediate 36

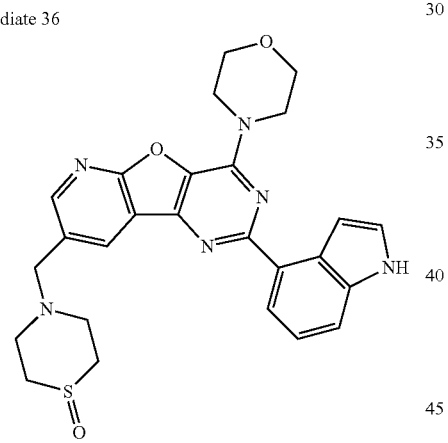

Example AK

To a suspension of Intermediate 36 (100 mg, 0.24 mmol, 1.0 eq) in CH$_2$Cl$_2$ (10 mL) was added thiomorpholine-1-oxide hydrochloride (112 mg, 0.72 mmol, 3.0 eq) and sodium acetate (59 mg, 0.72 mmol, 3.0 eq). The reaction mixture was heated to reflux for 2 h, cooled to rt and sodium triacetoxyborohydride (102 mg, 0.72 mmol, 2.0 eq) added in one portion. After 16 h at rt, the reaction mixture was partitioned between water (10 mL) and CH$_2$Cl$_2$ (15 mL). The aqueous phase was re-extracted with CH$_2$Cl$_2$ (2×15 mL) and the combined organics were dried over magnesium sulfate, filtered, and concentrated in vacuo. The residue (157 mg) was purified by flash chromatography with EtOAc/MeOH (1:0-4:1) to afford Example AK as pale yellow solids (91 mg, 73%)

$^1$H NMR (DMSO-d$_6$) $\delta_H$: 11.32 (br s, 1H), 8.83 (d, J=1.9 Hz, 1H), 8.71 (d, J=1.9 Hz, 1H), 8.28 (d, J=7.5 Hz, 1H), 7.43-7.66 (m, 3H), 7.26 (t, J=7.7 Hz, 1H), 3.97-4.13 (m, 4H), 3.79-3.93 (m, 6H), 2.94 (quin, J=10.3 Hz, 4H), 2.66-2.83 (m, 4H).

MS (ES$^+$) 519.0 [M+H]$^+$.

Example AL

4-{[4-(3-Methyl-1H-indol-4-yl)-6-(morpholin-4-yl)-8-oxa-3,5,10-triazatricyclo[7.4.0.0$^{2,7}$]trideca-1(13),2(7),3,5,9,11-hexaen-12-yl]methyl}-1$\lambda^4$-thiomorpholin-1-one

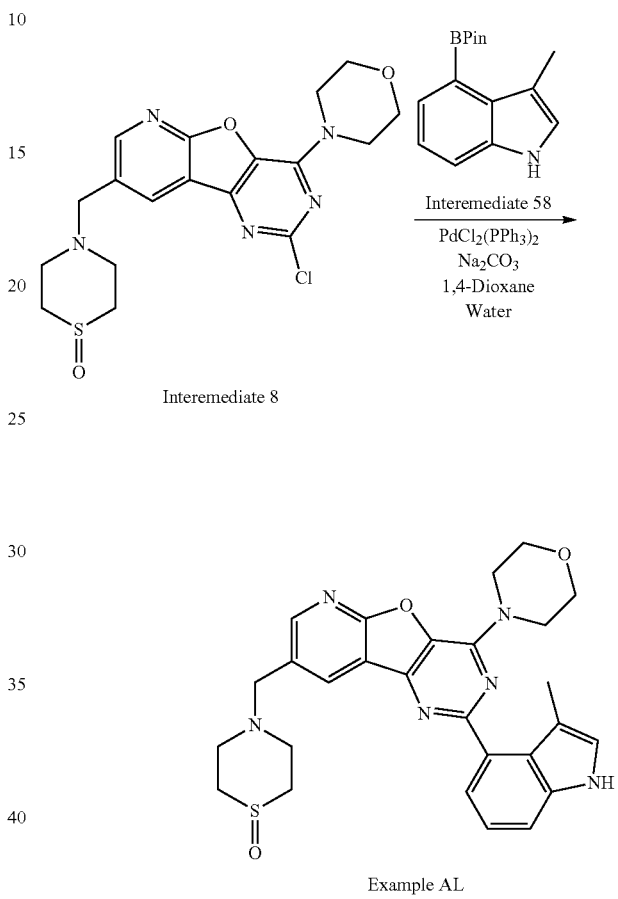

Example AL

To Intermediate 8 (66 mg, 0.16 mmol, 1.0 eq) was added Intermediate 58 (80 mg, 0.31 mmol, 2 eq), PdCl$_2$(PPh$_3$)$_2$ (22 mg, 31 μmol, 0.2 eq) and sodium carbonate (33 mg, 0.31 mmol, 2 eq), followed by 1,4-dioxane-water (4:1, 1.6 mL). The reaction mixture was heated to 95° C. for 4 h. It was then cooled to rt and partitioned between CH$_2$Cl$_2$ (20 mL) and aqueous sodium chloride solution (12.5% w/w, 20 mL). The aqueous phase was re-extracted with CH$_2$Cl$_2$ (3×5 mL) and the combined organics were dried over MgSO$_4$. The drying agent was removed by filtration and the filtrate was Pd-scavenged with MP-TMT resin (~141 mg, 1.1 mmol/g, 1 eq) for 5 h. The resin was removed by filtration and the filtrate was concentrated under reduced pressure. The residue was purified by silica gel column chromatography with EtOAc/MeOH (1:0-4:1) to afford Example AL as an off-white solid (53 mg, 66%).

$^1$H NMR (DMSO-d$_6$) $\delta_H$: 10.94 (br s, 1H), 8.62 (d, J=2.1 Hz, 1H), 8.54 (d, J=2.1 Hz, 1H), 7.44 (dd, J=8.0, 1.0 Hz, 1H), 7.28 (dd, J=7.2, 0.9 Hz, 1H), 7.08-7.20 (m, 2H), 4.00-4.12 (m, 4H), 3.72-3.90 (m, 6H), 2.83-3.02 (m, 4H), 2.61-2.82 (m, 4H), 2.02 (d, J=0.9 Hz, 3H).

MS (ES$^+$) 517.0 [M+H]$^+$.

Example AM

4-{[4-(6-Chloro-1H-indol-4-yl)-6-(morpholin-4-yl)-8-oxa-3,5,10-triazatricyclo[7.4.0.0²,⁷]trideca-1(13),2(7),3,5,9,11-hexaen-12-yl]methyl}-1λ⁴-thiomorpholin-1-one

Example AN

4-[6-(morpholin-4-yl)-12-[(1-oxo-1λ⁴-thiomorpholin-4-yl)methyl]-8-oxa-3,5,10-triazatricyclo[7.4.0.0²,⁷]trideca-1(13),2(7),3,5,9,11-hexaen-4-yl]-1H-indole-3-carbonitrile

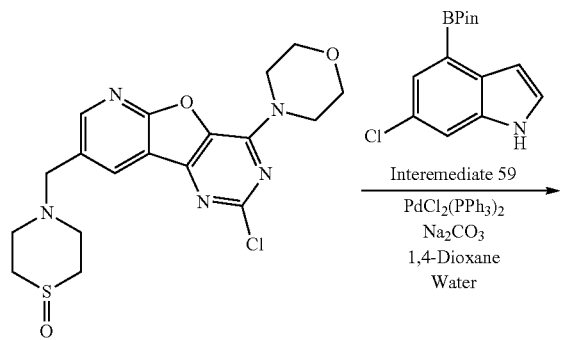

Interemediate 8

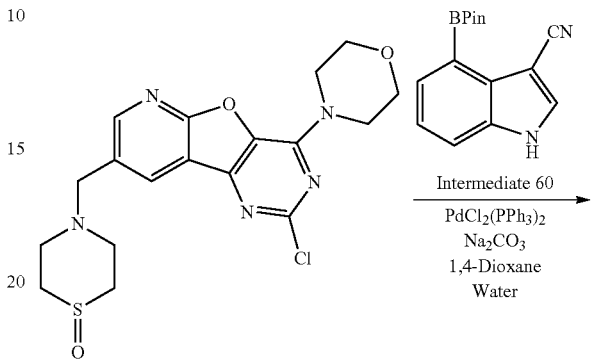

Interemediate 8

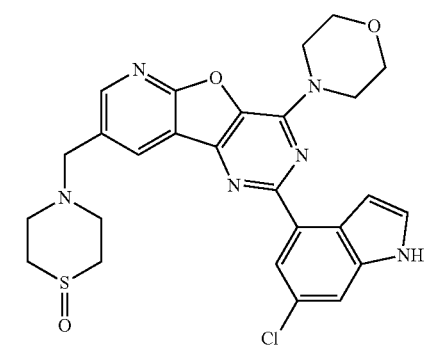

Example AM

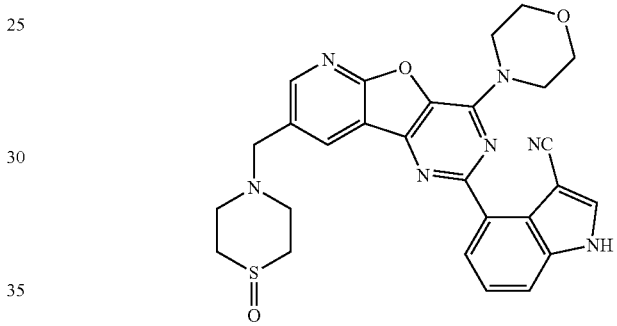

Example AN

To Intermediate 8 (53 mg, 0.13 mmol, 1.0 eq) was added Intermediate 59 (70 mg, 0.25 mmol, 2 eq), PdCl₂(PPh₃)₂ (18 mg, 25 µmol, 0.2 eq) and sodium carbonate (27 mg, 0.25 mmol, 2 eq), followed by 1,4-dioxane-water (4:1, 1.25 mL). The reaction mixture was heated to 95° C. for 4.6 h. It was then cooled to rt and partitioned between CH₂Cl₂ (20 mL) and aqueous sodium chloride solution (12.5% w/w, 20 mL). The aqueous phase was re-extracted with CH₂Cl₂ (3×5 mL) and the combined organics were dried over MgSO₄. The drying agent was removed by filtration and the filtrate was Pd-scavenged with MP-TMT resin (~115 mg, 1.1 mmol/g, 1 eq) overnight. The resin was removed by filtration and the filtrate was concentrated under reduced pressure. The residue was purified by silica gel column chromatography with EtOAc/MeOH (1:0-4:1) to afford Example AM as a light tan solid (5 mg, 8%).

¹H NMR (DMSO-d₆) δ$_H$: 11.42 (br s, 1H), 8.66 (d, J=2.1 Hz, 1H), 8.62 (d, J=2.1 Hz, 1H), 8.14 (d, J=1.9 Hz, 1H), 7.47-7.61 (m, 3H), 4.08-4.20 (m, 4H), 3.85-3.94 (m, 4H), 3.84 (s, 2H), 2.84-3.02 (m, 4H), 2.65-2.84 (m, 4H).

MS (ES⁺) 536.9 [M+H]⁺.

To Intermediate 8 (79 mg, 0.19 mmol, 1.0 eq) was added Intermediate 60 (100 mg, 0.37 mmol, 2 eq), PdCl₂(PPh₃)₂ (26 mg, 37 µmol, 0.2 eq) and sodium carbonate (40 mg, 0.37 mmol, 2 eq), followed by 1,4-dioxane-water (4:1, 1.9 mL). The reaction mixture was heated to 95° C. for 2.5 h. It was then cooled to rt and partitioned between CH₂Cl₂ (20 mL) and aqueous sodium chloride solution (12.5% w/w, 20 mL). The aqueous phase was re-extracted with CH₂Cl₂ (3×5 mL) and the combined organics were dried over Na₂SO₄. The drying agent was removed by filtration and the filtrate was Pd-scavenged with MP-TMT resin (~170 mg, 1.1 mmol/g, 1 eq) overnight. The resin was removed by filtration and the filtrate was concentrated under reduced pressure. The residue was purified by silica gel column chromatography with EtOAc/MeOH (1:0-4:1) to afford Example AN as a light brown solid (10 mg, 10%).

¹H NMR (DMSO-d₆) δ$_H$: 12.39 (br s, 1H), 8.68 (d, J=2.1 Hz, 1H), 8.61 (d, J=2.3 Hz, 1H), 8.38 (d, J=2.8 Hz, 1H), 7.94 (dd, J=7.3, 0.9 Hz, 1H), 7.67 (dd, J=8.1, 0.9 Hz, 1H), 7.41 (t, J=7.8 Hz, 1H), 4.05-4.20 (m, 4H), 3.75-3.93 (m, 6H), 2.65-3.03 (m, 8H).

MS (ES⁺) 528.0 [M+H]⁺.

Biological Data

Biochemical activity against class I PI3K isoforms was confirmed by either K$_i$ determination using the non-radiometric ADP-Glo™ assay (Promega, Madison, Wis., USA) at Proqinase GmbH, or IC$_{50}$ determination using the HTRF biochemical assay at Reaction Biology Corp.

| Compound | K_i PI3K (nM) | | | |
|---|---|---|---|---|
| | p110α | p110β | p110δ | p110γ |
| A | *** | * | * | **** |
| B | ** | * | * | *** |
| C | * | * | * | *** |
| D | **** | * | * | **** |
| E | *** | * | * | *** |
| F | **** | **** | **** | **** |
| G | ** | * | * | *** |
| H | ** | * | * | *** |
| I | * | * | * | **** |
| J | *** | * | * | **** |
| K | *** | * | * | **** |
| L | ** | * | * | *** |
| M | NT | NT | NT | NT |
| N | **** | **** | **** | **** |
| O | **** | * | * | **** |
| P | *** | * | * | *** |
| Q | **** | *** | * | **** |
| R | **** | **** | **** | **** |
| S | NT | NT | NT | NT |
| T | *** | * | * | **** |
| U | **** | *** | * | **** |
| V | **** | *** | * | **** |
| W | * | * | * | **** |
| X | **** | **** | **** | **** |
| Y | ** | * | * | *** |
| Z | * | * | * | ** |
| AG | ** | * | * | *** |
| AH | *** | * | * | **** |
| AI | **** | *** | * | **** |
| AJ | **** | *** | * | **** |
| AK | **** | *** | *** | **** |
| AL | **** | **** | *** | **** |
| AM | **** | **** | *** | **** |
| AN | **** | **** | **** | **** |

Key:
**** >10 uM
*** ≤10 uM > 1 uM
** ≤1 uM > 500 nM
* ≤500 nM
NT: not tested

| EXAMPLE | PI3K IC50 (nM) | | | |
|---|---|---|---|---|
| | p110α | p110β | p110δ | p110γ |
| AA | * | * | * | ** |
| AB | * | * | * | ** |
| AC | * | * | * | * |
| AD | * | * | * | * |
| AE | * | * | * | * |
| AF | * | * | * | ** |

Key:
**** >10 uM
*** ≤10 uM > 1 uM
** ≤1 uM > 500 nM
* ≤500 nM

Rodent Pharmacokinetic Comparative Data

It has been shown that compounds of the invention have improved pharmacokinetic parameters, such as increased bioavailability and/or reduced clearance (data below for mice).

Example B

The following protocol was used to determine oral bioavailability and clearance and the results are shown below.
Species=male mouse;
Strain=Balb/c;
18 male mice were divided into two groups Group 1 (3 mg/kg; i.v.), Group 2 (10 mg/kg; p.o.) with each group comprising of nine mice;
Blood samples (approximately 60 μL) were collected from retro orbital plexus under light isoflurane anesthesia such that the samples were obtained at pre-dose, 0.08, 0.25, 0.5, 1, 2, 4, 8 and 24 hr (i.v.) and pre-dose, 0.25, 0.5, 1, 2, 4, 6, 8 and 24 hr (p.o.);
The blood samples were collected from set of three mice at each time point in labeled micro centrifuge tube containing K2EDTA as anticoagulant;
Plasma samples were separated by centrifugation of whole blood and stored below −70° C. until bioanalysis;
All samples were processed for analysis by protein precipitation using acetonitrile (ACN) and analyzed with fit for purpose LC/MS/MS method (LLOQ: 2.02 ng/mL);
Pharmacokinetic parameters were calculated using the non-compartmental analysis tool of Phoenix WinNonlin (Version 6.3)
Formulation:
Animals in Group 1 were administered intravenously with Example B solution formulation in 5% NMP, 5% Solutol HS and 90% of 20% HPβCD via tail vein at a dose of 3 mg/kg.
Animals in Group 2 were administered with oral solution formulation of Example B in 5% NMP, 5% Solutol HS and 90% of 20% HPβCD at a dose of 10 mg/kg.
Dosing: 10 mg/kg P.O. and 3 mg/kg I.V.
Plasma PK Summary:

| Parameters-IV, 3 mg/kg | Value-Mesylate Salt |
|---|---|
| $t_{1/2}$ (hr) | 3.44 |
| $C_{max}$ (ng/mL) | 5324.39 |
| $AUC_{last}$ (hr*ng · mL) | 2802.91 |
| $AUC_{inf}$ (hr*ng/mL) | 2942.15 |
| Clearance (mL/hr/Kg) | 1019.4 |
| Vss (L/Kg) | 1.44 |

| Parameters-PO, 10 mg/kg | Value-Mesylate Salt |
|---|---|
| $T_{max}$ (hr) | 0.5 |
| $C_{max}$ (ng/mL) | 3825.72 |
| $AUC_{last}$ (hr*ng/mL) | 7691.30 |
| $AUC_{inf}$ (hr* ng/mL) | 7697.29 |
| Bioavailability | 82% |

The Plasma PK of Example B was compared side by Side to compound without a sulfur moiety:

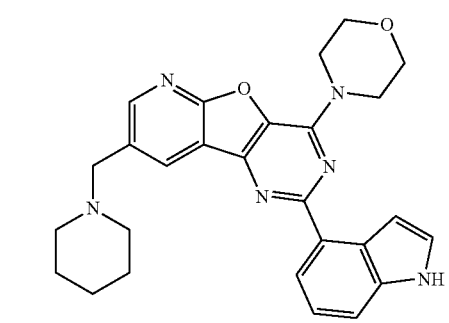 [SMILES: c1cc(-c2nc(N3CCOCC3)c3oc4ncc(CN5CCCCC5)cc4c3n2)c2cc[nH]c2c1]

The following protocol, substantially similar to that of Example B was used to determine oral bioavailability and clearance, and the results are shown below:
Species=male mouse;
Strain=CD1;
n=3 male mice per time point per route;
Terminal blood sampling at 8 time points (5 min, 10 min, 0.5 hr, 1 hr, 3 hr, 6 hr, 8 hr and, 24 hr);
Collection of plasma, bio-analysis and report of pharmacokinetic parameters.
Formulation: 10% DMSO, 90% Saline
Dosing: 10 mg/kg P.O. and 5 mg/kg I.V.
Plasma PK Summary:

| Parameters-IV, 5 mg/kg | Value-Mesylate Salt |
|---|---|
| $t_{1/2}$ (hr) | 1.6 |
| $T_{max}$ (hr) | 0.08 |
| $C_{max}$ (ng/mL) | 1618 |
| $AUC_{last}$ (hr*ng · mL) | 1245 |
| $AUC_{all}$ (hr*ng/mL) | 1245 |
| $AUC_{inf}$ (hr*ng/mL) | 1261 |
| Clearance (mL/hr/Kg) | 3966 |
| Vd (mL/Kg) | 4601 |

| Parameters-PO, 10 mg/kg | Value-Mesylate Salt |
|---|---|
| $t_{1/2}$ (hr) | 1.9 |
| $T_{max}$ (hr) | 1.0 |
| $C_{max}$ (ng/mL) | 212 |
| $AUC_{last}$ (hr*ng/mL) | 657 |
| $AUC_{all}$ (hr*ng/mL) | 657 |
| $AUC_{inf}$ (hr*ng/mL) | 700 |
| Bioavailability | 27.8% |

The plasma PK of Example B was also compared side by side to a compound in which the terminal sulfur atom was replaced by an oxygen (compound K in WO 2011/021038).

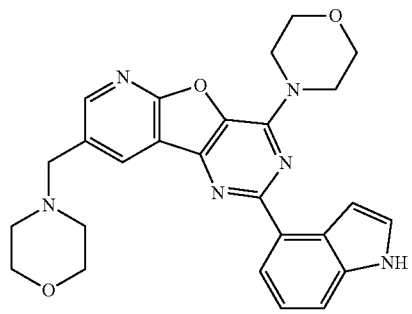 [SMILES: c1cc(-c2nc(N3CCOCC3)c3oc4ncc(CN5CCOCC5)cc4c3n2)c2cc[nH]c2c1]

The following protocol was used to determine oral bioavailability and clearance, and the results are shown below:
Species=male mouse;
Strain=Balb/c;
18 male mice were divided into two groups Group 1 (3 mg/kg; I.V.), Group 2 (10 mg/kg; P.O.) with each group comprising of nine mice;
Blood samples (approximately 60 μL) were collected from retro orbital plexus under light isoflurane anesthesia such that the samples were obtained at pre-dose, 0.08, 0.25, 0.5, 1, 2, 4, 8 and 24 hr (I.V.) and pre-dose, 0.25, 0.5, 1, 2, 4, 6, 8 and 24 hr (P.O.);
The blood samples were collected from a set of three mice at each time point in labelled micro centrifuge tube containing K2EDTA as anticoagulant;
Plasma samples were separated by centrifugation of whole blood and stored below −70° C. until bioanalysis;
All samples were processed for analysis by protein precipitation using acetonitrile (ACN) and analysed with fit for purpose LC/MS/MS method (LLOQ: 2.02 ng/mL);
Pharmacokinetic parameters were calculated using the non-compartmental analysis tool of Phoenix WinNonlin (Version 6.3).
Formulation:
Animals in Group 1 were administered intravenously with compound K solution formulation in 5% NMP, 5% solutol HS-15 and 90% normal saline via tail vein at a dose of 3 mg/kg.
Animals in Group 2 were administered with oral solution formulation of compound K in 5% NMP, 5% solutol HS-15 and 90% normal saline at a dose of 10 mg/kg;
Dosing: 10 mg/kg P.O. and 3 mg/kg I.V.
Plasma PK Summary:

| Parameters-IV, 3 mg/kg | Value |
|---|---|
| $t_{1/2}$ (hr) | 1.33 |
| $C_{max}$ (ng/mL) | 2984.57 |
| $AUC_{last}$ (hr*ng · mL) | 2654.15 |
| $AUC_{inf}$ (hr*ng/mL) | 2685.87 |
| Clearance (mL/hr/Kg) | 1117.2 |
| Vss (L/Kg) | 1.81 |

| Parameters-PO, 10 mg/kg | Value |
|---|---|
| $T_{max}$ (hr) | 0.25 |
| $C_{max}$ (ng/mL) | 1719.95 |
| $AUC_{last}$ (hr*ng/mL) | 4891.95 |
| $AUC_{inf}$ (hr* ng/mL) | 5139.78 |
| F | 55% |

Summary

| Compound | Oral Bioavailability (F) | Clearance (mL/hr/kg) |
|---|---|---|
| Example B | 82% | 1019.4 |
| Example B without sulphur (comparative) | 28% | 3966 |
| Example K from WO2011/021038 (comparative) | 50% | 1117.2 |

The invention claimed is:
1. A compound of formula I:

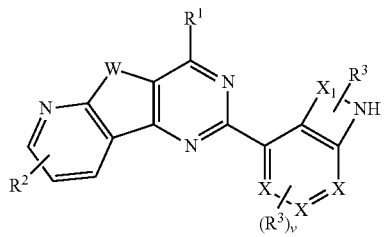

or a pharmaceutically acceptable salt thereof and/or stereoisomers thereof, wherein:
W is selected from the group consisting of O, N—H, N—($C_1$-$C_{10}$ alkyl), and S(O)$_{ww}$, wherein ww is 0, 1 or 2;
each X is independently selected from CH or N;

$X_1$ is selected from the group consisting of —$CH_2$—$CH_2$—, —CH=CH—, and —$CH_2$—C(O)— wherein C(O) is attached to NH;

v is selected from 0, 1, 2 and 3;

$R^1$ is a 5 to 7-membered heterocycle containing at least 1 heteroatom selected from N or O;

$R^2$ is -L-Y;

L is selected from the group consisting of a direct bond, $C_1$-$C_{10}$ alkylene, $C_2$-$C_{10}$ alkenylene, and $C_2$-$C_{10}$ alkynylene;

Y is a 4- to 8-membered heterocycle containing at least one nitrogen atom and at least one sulfur atom, or —N($R^5$)-A-S($O_q$)$R^6$;

$R^5$ is independently selected from the group consisting of H, $C_1$-$C_{10}$ alkyl, $C_2$-$C_{10}$ alkenyl, and $C_3$-$C_{10}$ alkynyl;

$R^6$ is independently selected from the group consisting of $C_1$-$C_{10}$ alkyl, $C_2$-$C_{10}$ alkenyl, $C_3$-$C_{10}$ alkynyl, fluoro $C_1$-$C_{10}$ alkyl, —O—$C_1$—$C_{10}$ alkyl, —NH—$C_1$-$C_{10}$ alkyl, —O—fluoro $C_1$-$C_{10}$ alkyl, —NH-acyl, —NH—C(O)—NH—$C_1$-$C_{10}$ alkyl, —C(O)—NH—$C_1$-$C_{10}$ alkyl, aryl, and heteroaryl;

A is selected from the group consisting of $C_1$-$C_{10}$ alkylene, $C_2$-$C_{10}$ alkenylene, and $C_3$-$C_{10}$ alkynylene;

q is selected from 0, 1, and 2;

each $R^3$ is independently selected from the group consisting of H, $C_1$-$C_{10}$ alkyl, halogen, —CN, —$CO_2$H, fluoro $C_1$-$C_{10}$ alkyl, —O-$C_1$-$C_{10}$ alkyl, —NH-$C_1$-$C_{10}$ alkyl, —$NH_2$, —S-$C_1$-$C_{10}$ alkyl, —O-fluoro $C_1$-$C_{10}$ alkyl, —NH-acyl, —NH-C(O)-NH-$C_1$-$C_{10}$ alkyl, —C(O)-NH-$C_1$-$C_{10}$ alkyl, aryl and heteroaryl; and each alkyl, alkenyl, alkylene, alkenylene, alkynylene, acyl, heterocycle or heteroaryl is optionally substituted by $C_1$-$C_6$ alkyl, hydroxy, $C_1$-$C_3$ hydroxyalkyl, $C_1$-$C_3$ alkoxy, $C_1$-$C_3$ haloalkoxy, fluoro $C_1$-$C_3$ alkyl, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, acyl, halo, nitro, cyano, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl or bis $C_1$-$C_3$-alkyl aminosulfonyl.

2. The compound according to claim 1, wherein $R^2$ is -L-Y; wherein
L is selected from the group consisting of a direct bond, $C_1$-$C_{10}$ alkylene, $C_2$-$C_{10}$ alkenylene or $C_2$-$C_{10}$ alkynylene; and
Y is a 4- to 7-membered heterocycle containing at least one nitrogen atom and at least one sulfur atom, or —N($R^5$)-A-S($O_q$)$R^6$, wherein $R^5$, $R^6$, A and q are as defined in claim 1.

3. The compound according to claim 1, wherein $X_1$ is —CH=CH—.

4. The compound according to claim 1, wherein $R^3$ is independently selected from the group consisting of H, $C_1$-$C_{10}$ alkyl, halogen, and fluoro $C_1$-$C_{10}$ alkyl.

5. The compound according to claim 1, wherein $R^1$ is represented by any of the following structures:

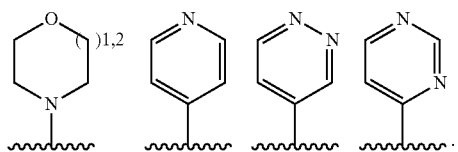

6. The compound according to claim 1, wherein $R^1$ is morpholine.

7. The compound according to claim 1, wherein W is O or S; and/or X is CH.

8. The compound according to claim 1, wherein L is $C_1$-$C_{10}$ alkylene.

9. The compound according to claim 1, wherein q is 2; and/or $R^5$ is $C_1$-$C_{10}$ alkyl.

10. The compound according to claim 1, wherein A is $C_1$-$C_{10}$ alkylene; and/or $R^6$ is independently selected from the group consisting of $C_1$-$C_{10}$ alkyl, fluoro $C_1$-$C_{10}$ alkyl, —O—$C_1$-$C_{10}$ alkyl, —NH—$C_1$-$C_{10}$ alkyl, aryl, and heteroaryl.

11. The compound according to claim 1, wherein Y is selected from Formula (III) or Formula (IV):

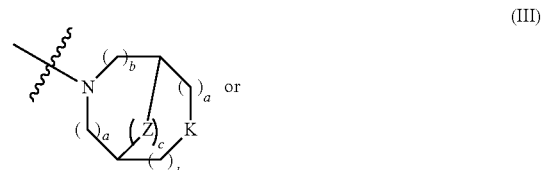

(III)

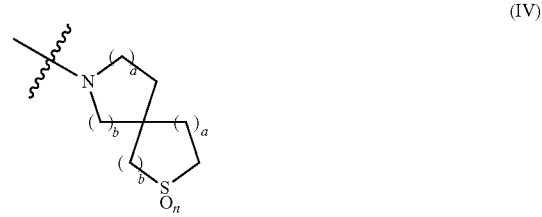

(IV)

wherein:

Z is selected from the group consisting of O, S, and $CH_2$;

K is selected from the group consisting of —S-, —S=O, —$SO_2$, and

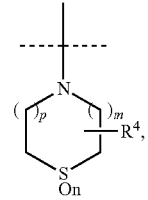

each a is independently selected from 1, 2, and 3;
each b is independently selected from 0, 1, and 2;
n is 0, 1, or 2; and
c is 0 or 1.

12. The compound according to claim 1, wherein Y is a heterocycloalkyl represented by:

wherein
m is selected from 0, 1 and 2,
n is selected from 0, 1 and 2,
p is selected from 0 and 1,
$R^4$ is independently selected from the group consisting of H, $C_1$-$C_{10}$ alkyl, halogen, fluoro $C_1$-$C_{10}$ alkyl, —O—

C₁-C₁₀ alkyl, —NH—C₁-C₁₀ alkyl, —NH₂, —S—C₁-C₁₀ alkyl, —O-flouro C₁-C₁₀ alkyl, —NH-acyl, —NH—C(O)—NH—C₁-C₁₀ alkyl, —C(O)—NH—C₁-C₁₀ alkyl, aryl and heteroaryl.
13. The compound according to claim 12 selected from the group consisting of:
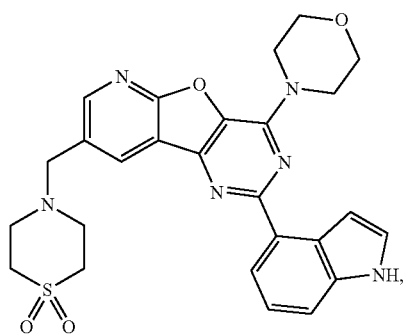
A
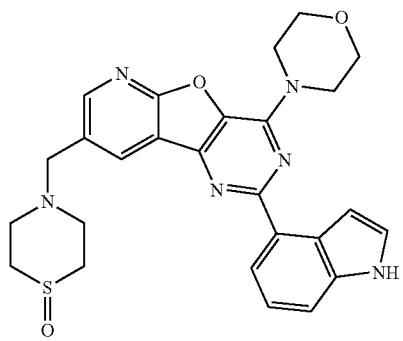
B
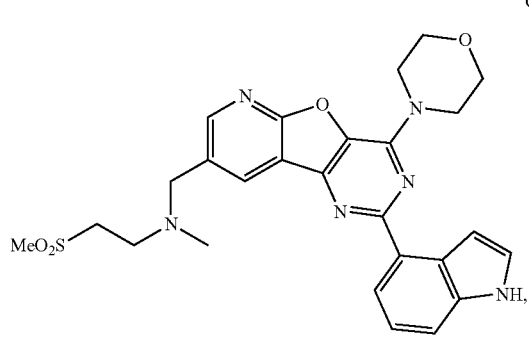
C
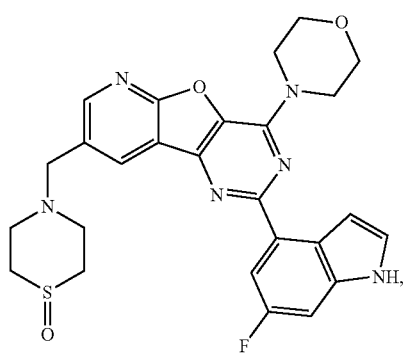
F
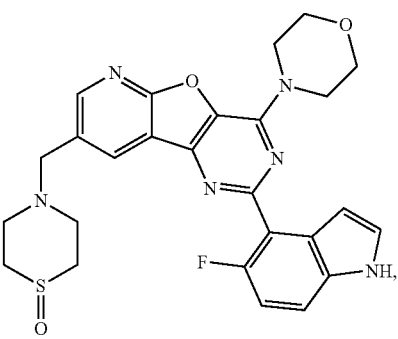
M
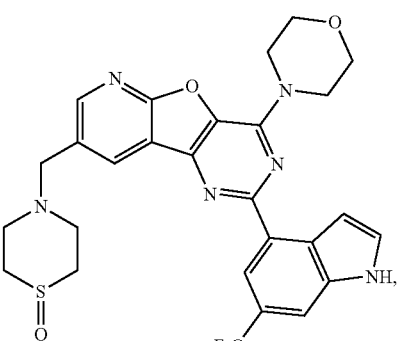
P
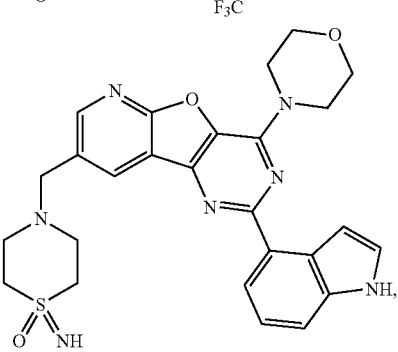
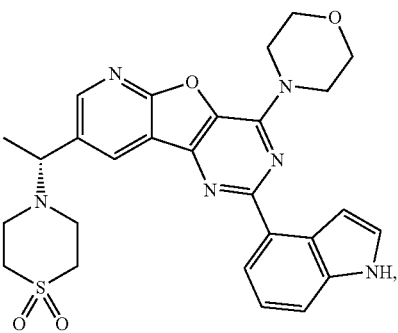
K
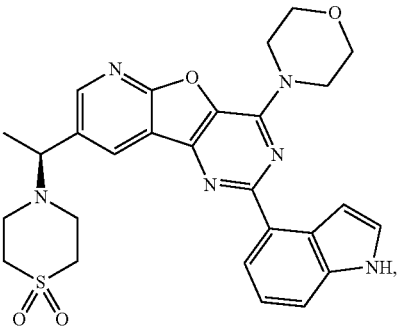

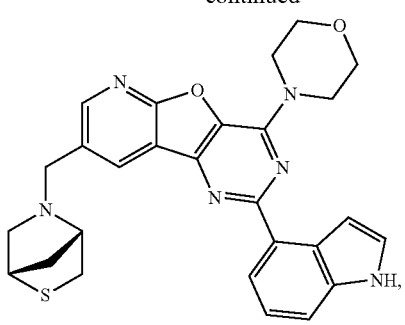
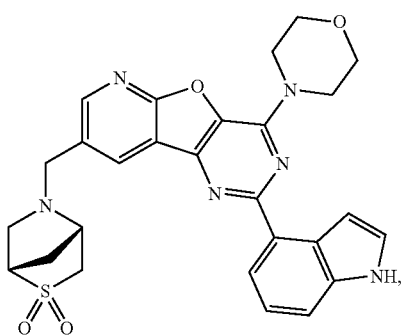
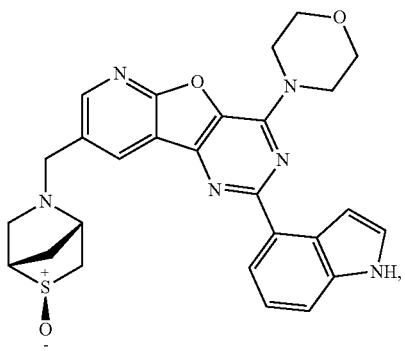
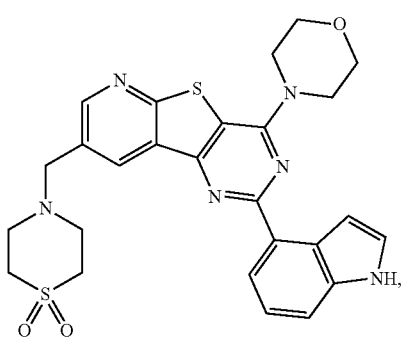
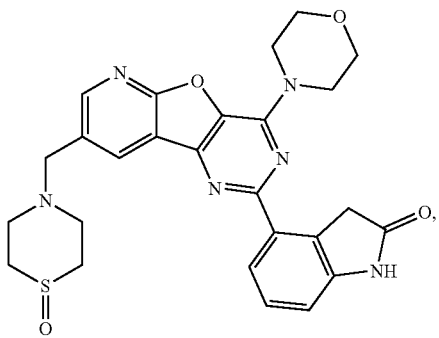
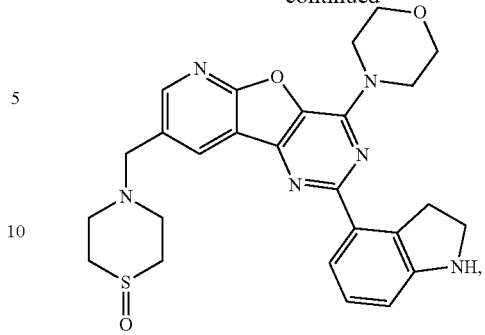
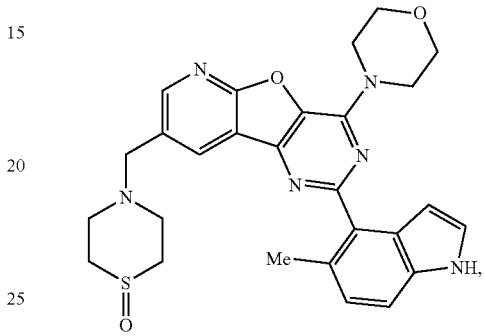
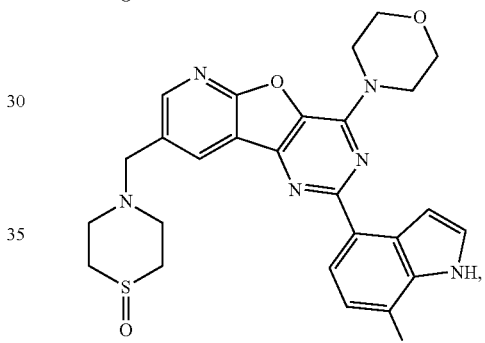
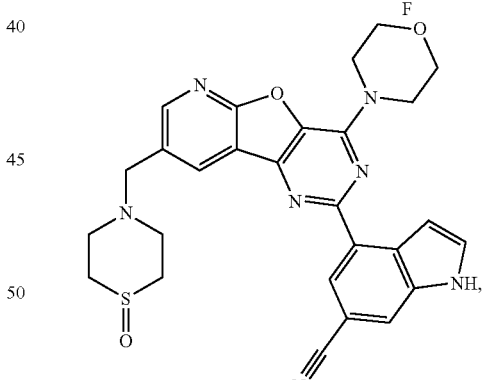
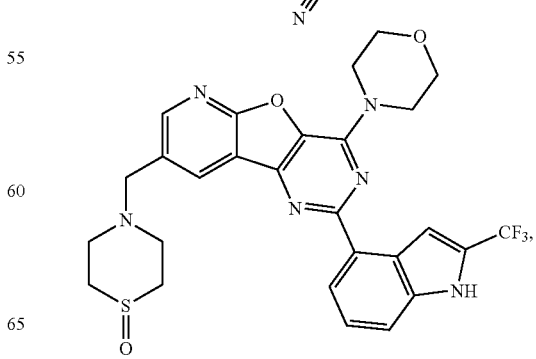

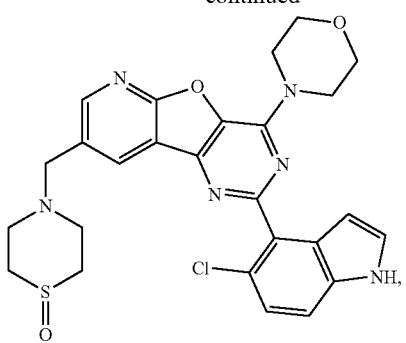
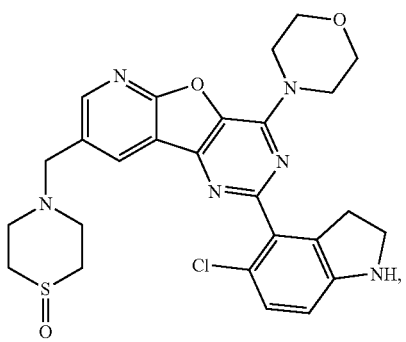
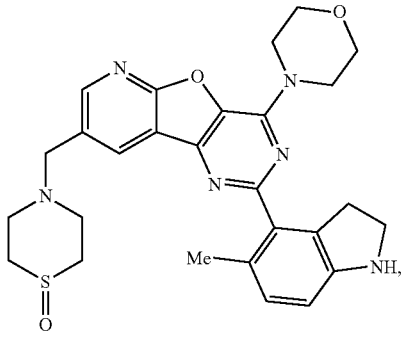
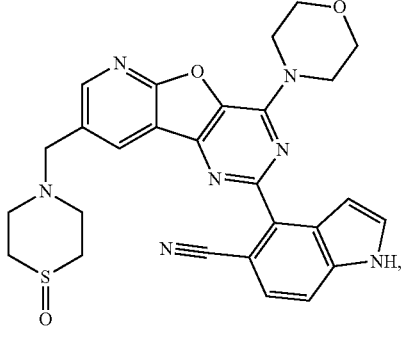
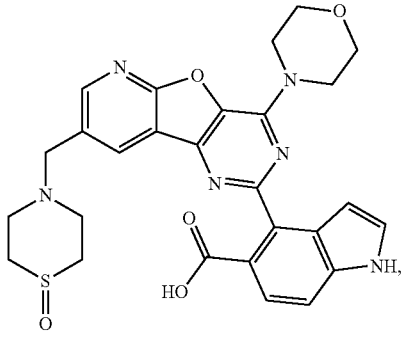
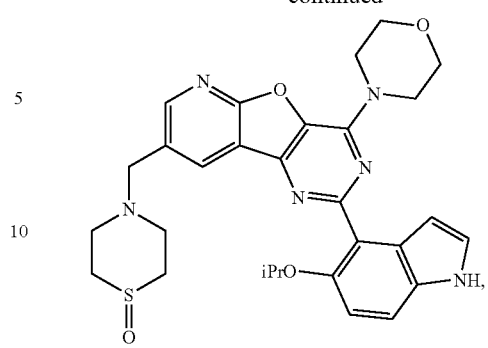
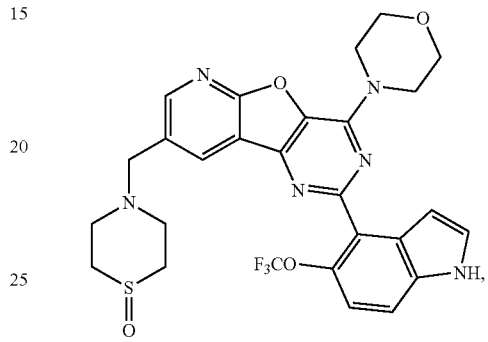
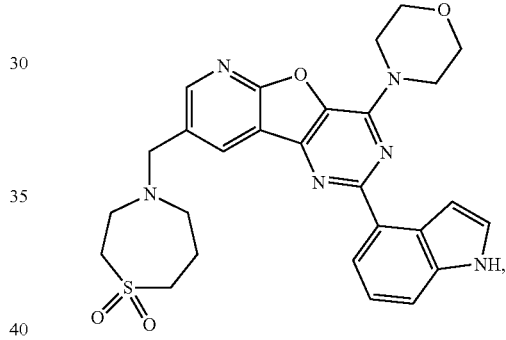
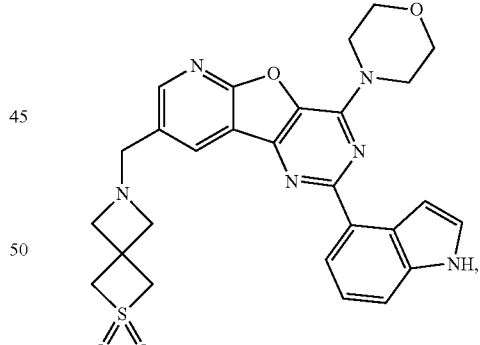
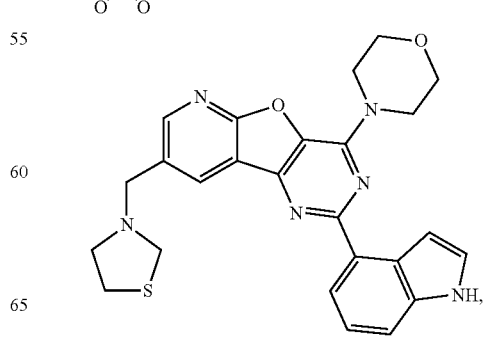

121
-continued
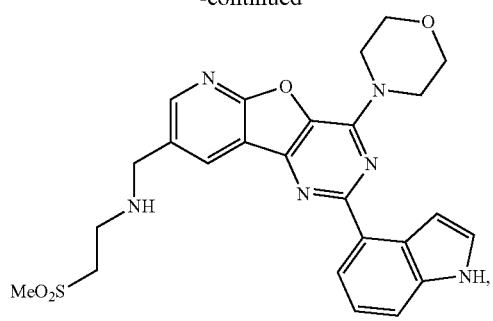
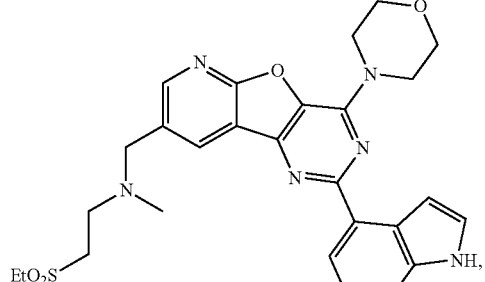
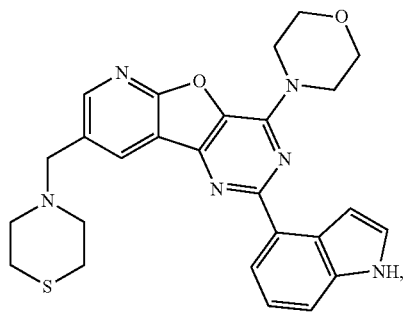
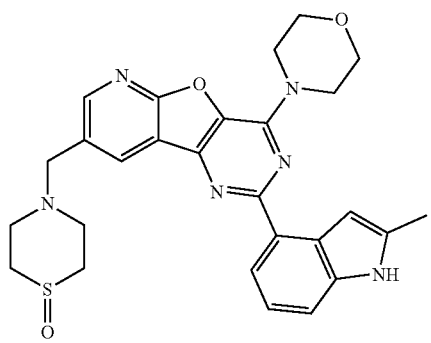
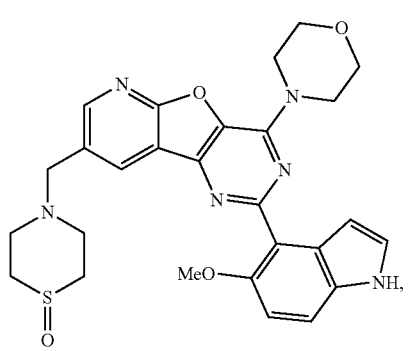
122
-continued
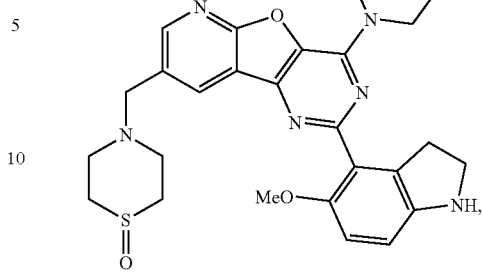
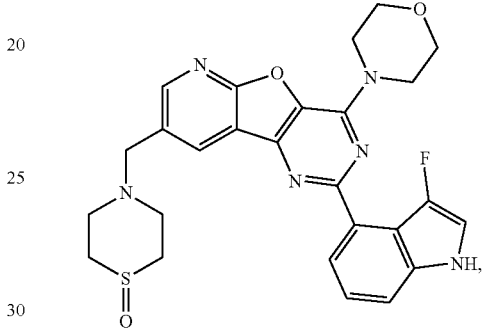
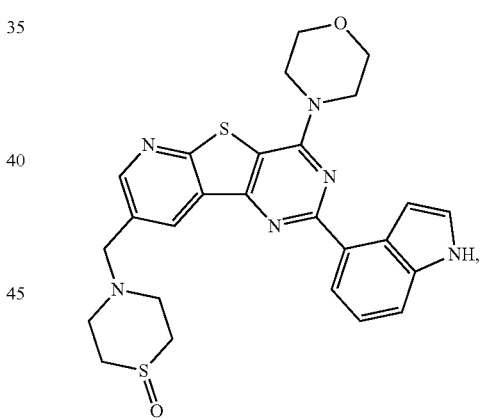
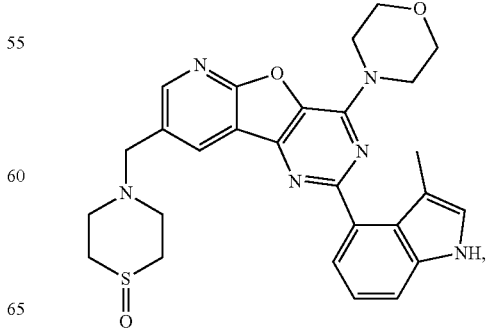

or a pharmaceutically acceptable salt thereof.

14. A pharmaceutical composition comprising the compound according to claim 1, and a pharmaceutically acceptable excipient.

15. A compound of formula II:

(II)

or a pharmaceutically acceptable salt thereof, wherein:
W is selected from the group consisting of O, N—H, N—($C_1$-$C_{10}$ alkyl) and S;
each X is independently selected from CH or N;
v is selected from 0, 1, 2 and 3;
$R^1$ is a 5 to 7-membered heterocycle containing at least 1 heteroatom selected from N or O;
$R^2$ is -L-Y;
L is selected from the group consisting of a direct bond, $C_1$-$C_{10}$ alkylene, $C_2$-$C_{10}$ alkenylene or $C_2$-$C_{10}$ alkynylene;
Y is a 4- to 7-membered heterocycle containing at least one nitrogen atom and at least one sulfur atom, or —N($R^5$)-A-S($O_q$)$R^6$;
$R^5$ is independently selected from the group consisting of H, $C_1$-$C_{10}$ alkyl, $C_2$-$C_{10}$ alkenyl, and $C_3$-$C_{10}$ alkynyl;

$R^6$ is independently selected from the group consisting of $C_1$-$C_{10}$ alkyl, $C_2$-$C_{10}$ alkenyl, $C_3$-$C_{10}$ alkynyl, fluoro $C_1$-$C_{10}$ alkyl, —O—$C_1$-$C_{10}$ alkyl, —NH—$C_1$-$C_{10}$ alkyl, —O-flouro $C_1$-$C_{10}$ alkyl, —NH-acyl, —NH—C(O)—NH—$C_1$-$C_{10}$ alkyl, —C(O)—NH—$C_1$-$C_{10}$ alkyl, aryl and heteroaryl;
A is selected from the group consisting of $C_1$-$C_{10}$ alkylene, $C_2$-$C_{10}$ alkenylene and $C_3$-$C_{10}$ alkynylene;
q is selected from 0, 1 and 2; and
each $R^3$ is independently selected from the group consisting of H, $C_1$-$C_{10}$ alkyl, halogen, fluoro $C_1$-$C_{10}$ alkyl, —O—$C_1$-$C_{10}$ alkyl, —NH—$C_1$-$C_{10}$ alkyl, —NH$_2$, —S—$C_1$-$C_{10}$ alkyl, —O-flouro $C_1$-$C_{10}$ alkyl, —NH-acyl, —NH—C(O)—NH—$C_1$-$C_{10}$ alkyl, —C(O)—NH—$C_1$-$C_{10}$ alkyl, aryl or heteroaryl; and
each alkyl, alkenyl, alkylene, alkenylene, alkynylene, acyl, heterocycle or heteroaryl is optionally substituted by $C_1$-$C_6$ alkyl, hydroxy, $C_1$-$C_3$ hydroxyalkyl, $C_1$-$C_3$ alkoxy, $C_1$-$C_3$ haloalkoxy, fluoro $C_1$-$C_3$ alkyl, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, acyl, halo, nitro, cyano, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —SO$_3$H, $C_1$-$C_3$ alkylsulfonyl, aminosulfonyl, mono $C_1$-$C_3$ alkyl aminosulfonyl or bis $C_1$-$C_3$-alkyl aminosulfonyl.

16. The compound according to claim 15, wherein $R^1$ is morpholine.

17. The compound according to claim 15, wherein W is O or S; and/or X is CH.

18. The compound according to claim 15, wherein $R^3$ is independently selected from H, $C_1$-$C_{10}$ alkyl, halogen, and fluoro $C_1$-$C_{10}$ alkyl.

19. The compound according to claim 15, wherein L is $C_1$-$C_{10}$ alkylene.

20. The compound according to claim 15, wherein Y is a heterocycloalkyl represented by:

wherein
m is selected from 0, 1 and 2,
n is selected from 0, 1 and 2,
p is selected from 0 and 1,
$R^4$ is independently selected from the group consisting of H, $C_1$-$C_{10}$ alkyl, halogen, fluoro $C_1$-$C_{10}$ alkyl, —O—$C_1$-$C_{10}$ alkyl, —NH—$C_1$-$C_{10}$ alkyl, —NH$_2$, —S—$C_1$-$C_{10}$ alkyl, —O-flouro $C_1$-$C_{10}$ alkyl, —NH-acyl, —NH—C(O)—NH—$C_1$-$C_{10}$ alkyl, —C(O)—NH—$C_1$-$C_{10}$ alkyl, aryl and heteroaryl.

* * * * *